（12） United States Patent
Lahm et al.

(10) Patent No.: US 9,049,862 B2
(45) Date of Patent: *Jun. 9, 2015

(54) ARTHROPODICIDAL ANTHRANILAMIDES

(71) Applicant: E I DU PONT DE NEMOURS AND COMPANY, Wilmington, DE (US)

(72) Inventors: George Philip Lahm, Wilmington, DE (US); Thomas Paul Selby, Hockessin, DE (US); Thomas Martin Stevenson, Newark, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/790,297

(22) Filed: Mar. 8, 2013

(65) Prior Publication Data

US 2013/0190313 A1  Jul. 25, 2013

Related U.S. Application Data

(60) Continuation of application No. 13/412,659, filed on Mar. 6, 2012, now Pat. No. 8,921,400, which is a continuation of application No. 13/017,322, filed on Jan. 31, 2011, now Pat. No. 8,148,521, which is a division of application No. 11/787,770, filed on Apr. 18, 2007, now Pat. No. 7,902,231, which is a division of application No. 10/483,168, filed as application No. PCT/US02/25615 on Aug. 13, 2002, now Pat. No. 7,232,836.

(60) Provisional application No. 60/311,919, filed on Aug. 13, 2001, provisional application No. 60/324,128, filed on Sep. 21, 2001, provisional application No. 60/369,661, filed on Apr. 2, 2002.

(51) Int. Cl.

| A01N 43/16 | (2006.01) |
| A01N 43/56 | (2006.01) |
| C07C 251/76 | (2006.01) |
| C07D 213/77 | (2006.01) |
| C07D 231/06 | (2006.01) |
| C07D 231/08 | (2006.01) |
| C07D 231/14 | (2006.01) |
| C07D 231/16 | (2006.01) |
| C07D 401/04 | (2006.01) |
| C07D 413/04 | (2006.01) |
| C07D 413/14 | (2006.01) |
| A01N 43/707 | (2006.01) |
| A01N 37/38 | (2006.01) |

(52) U.S. Cl.

CPC ............... *A01N 43/16* (2013.01); *A01N 43/56* (2013.01); *C07C 251/76* (2013.01); *C07D 213/77* (2013.01); *C07D 231/06* (2013.01); *C07D 231/08* (2013.01); *C07D 231/14* (2013.01); *C07D 231/16* (2013.01); *C07D 401/04* (2013.01); *C07D 413/04* (2013.01); *C07D 413/14* (2013.01); *A01N 43/707* (2013.01); *A01N 37/38* (2013.01)

(58) Field of Classification Search
USPC ................. 424/93.41, 93.5, 630, 637; 544/92
See application file for complete search history.

(56) References Cited

U.S. PATENT DOCUMENTS

| 4,321,371 | A |  | 3/1982 | Parg et al. |
| 4,931,439 | A |  | 6/1990 | Kristinsson |
| 5,153,200 | A | * | 10/1992 | Hubele .......................... 514/275 |
| 5,602,126 | A |  | 2/1997 | Barnette et al. |
| 5,728,693 | A |  | 3/1998 | Stevenson |
| 5,998,424 | A |  | 12/1999 | Galemmo, Jr. et al. |
| 6,020,357 | A |  | 2/2000 | Pinto et al. |
| 6,403,620 | B1 |  | 6/2002 | Galemmo, Jr. et al. |
| 6,548,512 | B1 |  | 4/2003 | Pinto et al. |
| 6,602,895 | B2 |  | 8/2003 | Galemmo, Jr. et al. |
| 6,747,047 | B2 | * | 6/2004 | Lahm et al. .................... 514/341 |

(Continued)

FOREIGN PATENT DOCUMENTS

| AU | 2004294711 B2 | 5/2011 |
| AU | 2004294259 B2 | 6/2011 |

(Continued)

OTHER PUBLICATIONS

Federal register: May 20, 1998 (vol. 63, No. 97, pp. 1-9).*

(Continued)

*Primary Examiner* — Sabiha N Qazi

(57) ABSTRACT

This invention provides a composition comprising a a compound selected from Formula 1, an N-oxide and an agriculturally suitable salt thereof; and pymetrozine, wherein $R^1$, $R^2$, $R^3$, $R^{4a}$, $R^{4b}$ and $R^5$ are as defined in the disclosure.

8 Claims, No Drawings

(56) References Cited

U.S. PATENT DOCUMENTS

| | | |
|---|---|---|
| 6,875,768 B1 | 4/2005 | Machiya et al. |
| 6,995,178 B2 | 2/2006 | Lahm et al. |
| 7,199,138 B2 | 4/2007 | Finkelstein et al. |
| 7,232,836 B2 | 6/2007 | Lahm et al. |
| 7,247,647 B2 | 7/2007 | Hughes et al. |
| 7,339,057 B2 | 3/2008 | Taylor |
| 7,696,232 B2 | 4/2010 | Berger et al. |
| 7,696,233 B2 | 4/2010 | Lahm et al. |
| 7,875,634 B2 | 1/2011 | Hughes et al. |
| 7,902,231 B2 | 3/2011 | Lahm et al. |
| 8,022,067 B2 | 9/2011 | Annan et al. |
| 8,268,750 B2 | 9/2012 | Funke et al. |
| 8,268,751 B2 | 9/2012 | Funke et al. |
| 8,299,036 B2 | 10/2012 | Funke et al. |
| 2004/0102324 A1 | 5/2004 | Annis et al. |
| 2004/0110777 A1 | 6/2004 | Annis et al. |
| 2004/0138450 A1 | 7/2004 | Clark |
| 2004/0142984 A1 | 7/2004 | Lahm et al. |
| 2004/0171649 A1 | 9/2004 | Annis et al. |
| 2004/0192731 A1 | 9/2004 | Finkelstein et al. |
| 2004/0198984 A1 | 10/2004 | Lahm et al. |
| 2004/0198987 A1 | 10/2004 | Freudenberger et al. |
| 2004/0209923 A1 | 10/2004 | Berger et al. |
| 2004/0259913 A1 | 12/2004 | Clark |
| 2005/0075372 A1 | 4/2005 | Lahm et al. |
| 2005/0124600 A1 | 6/2005 | Clark et al. |
| 2005/0147633 A1 | 7/2005 | Stevenson |
| 2005/0274059 A1 | 12/2005 | Angst et al. |
| 2007/0142327 A1 | 6/2007 | Funke et al. |
| 2007/0244073 A1 | 10/2007 | Angst et al. |
| 2007/0259787 A1 | 11/2007 | Ohkawara |
| 2007/0270416 A1 | 11/2007 | Funke et al. |
| 2008/0027046 A1 | 1/2008 | Annan et al. |
| 2008/0305093 A1 | 12/2008 | Gutsche et al. |
| 2010/0055084 A1 | 3/2010 | Gutsche et al. |
| 2010/0137374 A1 | 6/2010 | Annan et al. |
| 2010/0152194 A1 | 6/2010 | Berger et al. |
| 2010/0160307 A1 | 6/2010 | Lahm et al. |
| 2010/0168042 A1 | 7/2010 | Funke et al. |
| 2010/0227893 A1 | 9/2010 | Ohkawara |
| 2010/0249070 A1 | 9/2010 | Funke et al. |
| 2010/0292226 A1 | 11/2010 | Funke et al. |
| 2011/0015076 A1 | 1/2011 | Angst et al. |
| 2011/0059846 A1 | 3/2011 | Gutsche et al. |
| 2011/0293533 A1 | 12/2011 | Annan et al. |
| 2012/0083491 A1 | 4/2012 | Funke et al. |
| 2012/0171183 A1 | 7/2012 | Lahm et al. |
| 2013/0123247 A1 | 5/2013 | Lahm et al. |
| 2013/0190259 A1 | 7/2013 | Lahm et al. |
| 2013/0190362 A1 | 7/2013 | Lahm et al. |
| 2014/0030243 A1 | 1/2014 | Lahm et al. |

FOREIGN PATENT DOCUMENTS

| | | |
|---|---|---|
| AU | 2004294710 B2 | 6/2011 |
| AU | 2004290501 B2 | 7/2011 |
| AU | 20042900502 B2 | 7/2011 |
| AU | 2004290500 B2 | 8/2011 |
| AU | 2011244872 A1 | 11/2011 |
| AU | 2011244912 A1 | 11/2011 |
| DE | 4428380 A | 8/1994 |
| DE | 19840322 A1 | 9/1998 |
| EP | 0919542 A2 | 6/1999 |
| EP | 1193254 A1 | 1/2001 |
| EP | 0991625 B1 | 6/2005 |
| EP | 1982594 A1 | 10/2008 |
| EP | 1686857 B1 | 12/2008 |
| EP | 1686858 B1 | 3/2009 |
| EP | 1691608 B1 | 2/2011 |
| EP | 1699290 B1 | 2/2011 |
| EP | 1686859 B1 | 8/2012 |
| NL | 0202078 A | 11/1992 |
| WO | 96/38419 | 12/1996 |
| WO | 98/28269 | 7/1998 |
| WO | 98/57937 | 12/1998 |
| WO | 99/35910 * | 7/1999 |
| WO | 01/02354 A1 | 1/2001 |
| WO | 01/32628 A1 | 5/2001 |
| WO | 01/70671 A2 | 9/2001 |
| WO | 02/48115 A2 | 6/2002 |
| WO | 02/070483 A1 | 9/2002 |
| WO | 03/015518 A1 | 2/2003 |
| WO | 03/015519 A1 | 2/2003 |
| WO | 03/016284 | 2/2003 |
| WO | 03/024222 A1 | 3/2003 |
| WO | 03/106427 | 12/2003 |
| WO | 2004/011447 | 2/2004 |
| WO | 2004/011453 | 2/2004 |
| WO | 2004/033468 | 4/2004 |
| WO | 2004/046129 | 6/2004 |
| WO | 2004/067528 A1 | 8/2004 |
| WO | 2005/048711 A1 | 6/2005 |
| WO | 2005/048712 A1 | 6/2005 |
| WO | 2005/048713 A1 | 6/2005 |
| WO | 2005/053393 A1 | 6/2005 |
| WO | 2005/053405 A1 | 6/2005 |
| WO | 2005/053406 A1 | 6/2005 |
| WO | 2005/079575 A1 | 9/2005 |
| WO | 2005/107468 A1 | 11/2005 |
| WO | 2006/007595 A1 | 1/2006 |
| WO | 2006/068669 A1 | 6/2006 |

OTHER PUBLICATIONS

Pymetrozine-Registration of Fulfill and Endeavor Insecticides (Jan. 1, 2001, New York Dept. of Environmental Protection, pp. 1-6).*
Christopher Thomas Ball (abstract of WO 1999025188 A3, publidhed Aug. 26, 1999).*
Opposition Grounds EP2263460, dated Jul. 22, 2013.
Opposition Grounds EP2258191, dated Jul. 22, 2013.
Opposition Grounds EP2263458, dated Jul. 22, 2013.
Opposition Grounds EP2263459, dated Jul. 22, 2013.
Opposition Grounds EP2263461, dated Sep. 12, 2013.
Opposition Grounds EP2274981, dated Sep. 26, 2013.
Opposition Grounds EP2266402, dated Mar. 27, 2013.
Opposition Grounds EP2281458, dated Mar. 27, 2013.
XP002177117 Suto, Mark J. et al., Tetrahedron Letters, vol. 36 No. 40, 1995, p. 7213-7216, Elsevier Science Publishers, Amsterdam, NL.
Klaubert et al., J. Med Chem., vol. 24, No. 6 p. 748-752, 1981.
EP2060179 Opposition Grounds, dated Nov. 15, 2012.
EP2060180 Opposition Grounds, dated Nov. 22, 2012.
EP2060182 Opposition Grounds, dated Nov. 22, 2012.
EP2060181 Opposition Grounds, dated Feb. 15, 2013.
The Pesticide Manual, C D S Tomlin,k Twelve Edition, © 2000 BCPC, pp. 790-791.

* cited by examiner

ARTHROPODICIDAL ANTHRANILAMIDES

This application is a continuation of application Ser. No. 13/412,659, filed Mar. 6, 2012, which is a continuation of Ser. No. 13/017,322, filed Jan. 31, 2011, now U.S. Pat. No. 8,148,521, which is a division of Ser. No. 11/787,770 filed Apr. 18, 2007, now U.S. Pat. No. 7,902,231, which is a division of Ser. No. 10/483,168, filed Jan. 7, 2004, now U.S. Pat. No. 7,232,836, which is a national stage entry of PCT/US02/25615, filed Aug. 13, 2002. PCT/US02/25615 claims priority benefit from Provisional Application 60/311,919, filed Aug. 13, 2001; PCT/US02/25615 claims priority benefit from Provisional Application 60/324,128, filed on Sep. 21, 2001; and PCT/US02/25615 claims priority benefit from Provisional Application 60/369,661, filed Apr. 2, 2002.

BACKGROUND OF THE INVENTION

This invention relates to certain anthranilamides, their N-oxides, agriculturally suitable salts and compositions, and methods of their use for control of invertebrate pests such as arthropods in both agronomic and nonagronomic environments.

The control of invertebrate pests such as arthropods is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals, nursery crops, stored food and fiber products, livestock, household, and public and animal health is also important. Many products are commercially available for these purposes, but the need continues for new compounds which are more effective, less costly, less toxic, environmentally safer or have different modes of action.

NL 9202078 discloses N-acyl anthranilic acid derivatives of Formula i as insecticides

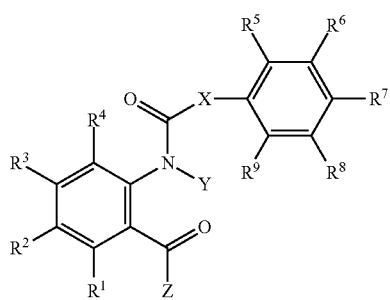

wherein, inter alia,
X is a direct bond;
Y is H or $C_1$-$C_6$ alkyl;
Z is $NH_2$, $NH(C_1$-$C_3$ alkyl) or $N(C_1$-$C_3$ alkyl)$_2$; and
$R^1$ through $R^9$ are independently H, halogen, $C_1$-$C_6$ alkyl, phenyl, hydroxy, $C_1$-$C_6$ alkoxy or $C_1$-$C_7$ acyloxy.

SUMMARY OF THE INVENTION

This invention pertains to a compound of Formula 1, its N-oxide or an agriculturally suitable salt of the compound

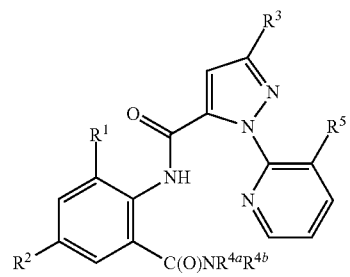

wherein
$R^1$ is $CH_3$, F, Cl or Br;
$R^2$ is F, Cl, Br, I or $CF_3$;
$R^3$ is $CF_3$, Cl, Br or $OCH_2CF_3$;
$R^{4a}$ is $C_1$-$C_4$ alkyl;
$R^{4b}$ is H or $CH_3$; and
$R^5$ is Cl or Br.

This invention also pertains to a composition for controlling an invertebrate pest comprising a biologically effective amount of a compound of Formula 1 and at least one additional component selected from the group consisting of surfactants, solid diluents and liquid diluents. This invention also pertains to a composition comprising a biologically effective amount of a compound of Formula 1 and an effective amount of at least one additional biologically active compound or agent.

This invention also pertains to a method for controlling an invertebrate pest comprising contacting the invertebrate pest or its environment with a biologically effective amount of a compound of Formula 1 (e.g., as a composition described herein). This invention also relates to such method wherein the invertebrate pest or its environment is contacted with a biologically effective amount of a compound of Formula 1 or a composition comprising a compound of Formula 1 and a biologically effective amount of at least one additional compound or agent for controlling invertebrate pests.

This invention further relates to a benzoxazinone compound of Formula 2

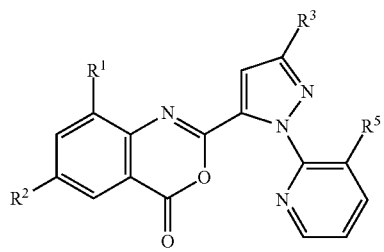

wherein
$R^1$ is $CH_3$, F, Cl or Br;
$R^2$ is F, Cl, Br, I or $CF_3$;
$R^3$ is $CF_3$, Cl, Br or $OCH_2CF_3$; and
$R^5$ is Cl or Br;
which is useful as a synthetic intermediate for preparing a compound of Formula 1.

This invention also relates to a pyrazolecarboxylic acid compound of Formula 4

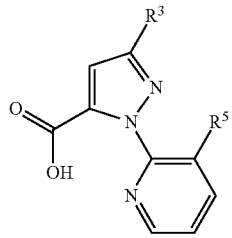

wherein
$R^3$ is $CF_3$, Cl, Br or $OCH_2CF_3$; and
$R^5$ is Cl or Br;
which is useful as a synthetic intermediate for preparing a compound of Formula 1.

DETAILS OF THE INVENTION

In the above recitations, the term "alkyl", used either alone or in compound words such as "alkylthio" or "haloalkyl" includes straight-chain or branched alkyl, such as, methyl, ethyl, n-propyl, i-propyl, or the different butyl isomers. One skilled in the art will appreciate that not all nitrogen containing heterocycles can form N-oxides since the nitrogen requires an available lone pair for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethydioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in Advances in *Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in Advances in *Heterocyclic Chemistry*, vol. 22, pp 390-392, A. R. Katritzky and A. J. Boulton, Eds., Academic Press.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula 1, N-oxides and agriculturally suitable salts thereof. The compounds of the invention may be present as a mixture of stereoisomers, individual stereoisomers, or as an optically active form.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

Preferred compounds for reasons of cost, ease of synthesis and/or biological efficacy are:
Preferred 1 Compounds of Formula 1 wherein $R^{4a}$ is $C_1$-$C_4$ alkyl and $R^{4b}$ is H; or $R^{4a}$ is $CH_3$ and $R^{4b}$ is $CH_3$.
Preferred 2 Compounds of Preferred 1 wherein $R^5$ is Cl.
Preferred 3 Compounds of Preferred 2 wherein $R^{4a}$ is $CH_3$, $CH_2CH_3$, $CH(CH_3)_2$ or $C(CH_3)_3$.
Preferred 4 Compounds of Preferred 3 wherein $R^2$ is Cl or Br.
Preferred 5 Compounds of Preferred 4 wherein $R^1$ is $CH_3$.
Preferred 6 Compounds of Preferred 4 wherein $R^1$ is Cl.
Preferred 7 Compounds of Formula 1 wherein $R^1$ is $CH_3$, Cl or Br; $R^2$ is F, Cl, Br, I or $CF_3$; $R^3$ is $CF_3$, Cl or Br; $R^{4a}$ is $C_1$-$C_4$ alkyl; $R^{4b}$ is H; and $R^5$ is Cl or Br.

Specifically preferred is a compound of Formula 1 selected from the group consisting of:
the compound of Formula 1 wherein $R^1$ is $CH_3$, $R^2$ is Br, $R^3$ is $CF_3$, $R^{4a}$ is $CH(CH_3)_2$, $R^{4b}$ is H, and $R^5$ is Cl;
the compound of Formula 1 wherein $R^1$ is $CH_3$, $R^2$ is Br, $R^3$ is $CF_3$, $R^{4a}$ is $CH_3$, $R^{4b}$ is H, and $R^5$ is Cl;
the compound of Formula 1 wherein $R^1$ is $CH_3$, $R^2$ is Br, $R^3$ is Br, $R^{4a}$ is $CH(CH_3)_2$, $R^{4b}$ is H, and $R^5$ is Cl;
the compound of Formula 1 wherein $R^1$ is $CH_3$, $R^2$ is Br, $R^3$ is Br, $R^{4a}$ is $CH_3$, $R^{4b}$ is H, and $R^5$ is Cl;
the compound of Formula 1 wherein $R^1$ is $CH_3$, $R^2$ is Br, $R^3$ is Cl, $R^{4a}$ is $CH(CH_3)_2$, $R^{4b}$ is H, and $R^5$ is Cl;
the compound of Formula 1 wherein $R^1$ is $CH_3$, $R^2$ is Br, $R^3$ is Cl, $R^{4a}$ is $CH_3$, $R^{4b}$ is H, and $R^5$ is Cl;
the compound of Formula 1 wherein $R^1$ is $CH_3$, $R^2$ is Cl, $R^3$ is $CF_3$, $R^{4a}$ is $CH(CH_3)_2$, $R^{4b}$ is H, and $R^5$ is Cl;
the compound of Formula 1 wherein $R^1$ is $CH_3$, $R^2$ is Cl, $R^3$ is $CF_3$, $R^{4a}$ is $CH_3$, $R^{4b}$ is H, and $R^5$ is Cl;
the compound of Formula 1 wherein $R^1$ is $CH_3$, $R^2$ is Cl, $R^3$ is Br, $R^{4a}$ is $CH(CH_3)_2$, $R^{4b}$ is H, and $R^5$ is Cl;
the compound of Formula 1 wherein $R^1$ is $CH_3$, $R^2$ is Cl, $R^3$ is Br, $R^{4a}$ is $CH_3$, $R^{4b}$ is H, and $R^5$ is Cl;
the compound of Formula 1 wherein $R^1$ is $CH_3$, $R^2$ is Cl, $R^3$ is Cl, $R^{4a}$ is $CH(CH_3)_2$, $R^{4b}$ is H, and $R^5$ is Cl;
the compound of Formula 1 wherein $R^1$ is $CH_3$, $R^2$ is Cl, $R^3$ is Cl, $R^{4a}$ is $CH_3$, $R^{4b}$ is H, and $R^5$ is Cl;
the compound of Formula 1 wherein $R^1$ is $CH_3$, $R^2$ is Cl, $R^3$ is $OCH_2CF_3$, $R^{4a}$ is $CH(CH_3)_2$, $R^{4b}$ is H, and $R^5$ is Cl;
the compound of Formula 1 wherein $R^1$ is $CH_3$, $R^2$ is Cl, $R^3$ is $OCH_2CF_3$, $R^{4a}$ is $CH_3$, $R^{4b}$ is H, and $R^5$ is Cl;
the compound of Formula 1 wherein $R^1$ is Cl, $R^2$ is Cl, $R^3$ is Br, $R^{4a}$ is $CH_3$, $R^{4b}$ is H, and $R^5$ is Cl; and
the compound of Formula 1 wherein $R^1$ is $CH_3$, $R^2$ is Cl, $R^3$ is $OCH_2CF_3$, $R^{4a}$ is $CH_3$, $R^{4b}$ is H, and $R^5$ is Cl.

The preferred compositions of the present invention are those which comprise the above preferred compounds. The preferred methods of use are those involving the above preferred compounds.

Of note are compounds of Formulae 1, 2 and 4 wherein $R^1$ is $CH_3$, Cl or Br; $R^2$ is F, Cl, Br, I or $CF_3$; $R^3$ is $CF_3$, Cl or Br; $R^{4a}$ is $C_1$-$C_4$ alkyl; $R^{4b}$ is H; and $R^5$ is Cl or Br.

The compounds of Formula 1 can be prepared by one or more of the following methods and variations as described in Schemes 1-11. The definitions of $R^1$, $R^2$, $R^3$, $R^{4a}$, $R^{4b}$ and $R^5$ in the compounds of Formulae 1-24 below are as defined above in the Summary of the Invention unless indicated otherwise.

Compounds of Formula 1 can be prepared by the reaction of benzoxazinones of Formula 2 with $C_1$-$C_4$ alkyl amines as outlined in Scheme 1.

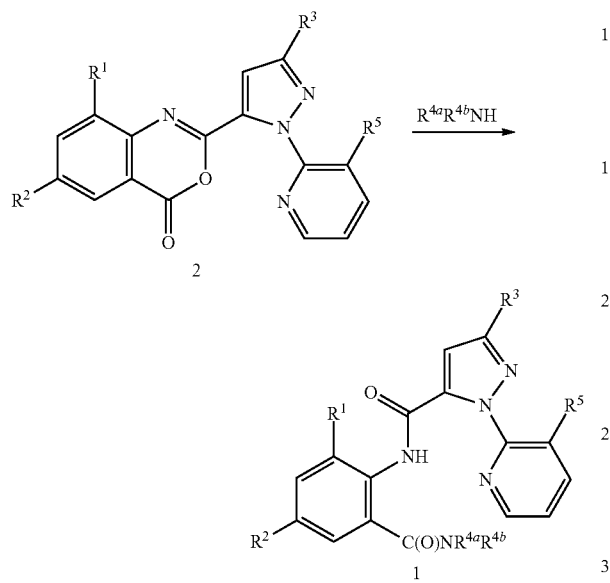

The reaction can be run neat or in a variety of suitable solvents including tetrahydrofuran, diethyl ether, dichloromethane or chloroform with optimum temperatures ranging from room temperature to the reflux temperature of the solvent. The general reaction of benzoxazinones with amines to produce anthranilamides is well documented in the chemical literature. For a review of benzoxazinone chemistry see Jakobsen et al., *Biorganic and Medicinal Chemistry* 2000, 8, 2095-2103 and references cited within. See also G. M. Coppola, *J. Heterocyclic Chemistry* 1999, 36, 563-588.

Benzoxazinones of Formula 2 can be prepared by a variety of known methods. Two methods that are especially useful are detailed in Schemes 2-3. In Scheme 2, a benzoxazinone of Formula 2 is prepared directly via coupling of a pyrazolecarboxylic acid of Formula 4 with an anthranilic acid of Formula 3.

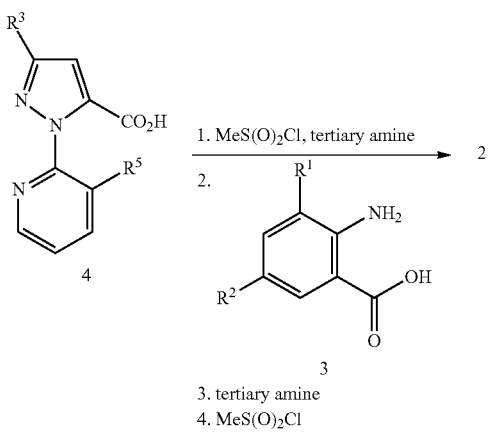

This involves sequential addition of methanesulfonyl chloride in the presence of a tertiary amine such as triethylamine or pyridine to a pyrazolecarboxylic acid of Formula 4, followed by the addition of an anthranilic acid of Formula 3, followed by a second addition of tertiary amine and methanesulfonyl chloride. This method generally affords good yields of the benzoxazinone and is illustrated with greater detail in Example 1.

Scheme 3 depicts an alternate preparation for benzoxazinones of Formula 2 involving coupling of a pyrazole acid chloride of Formula 6 with an isatoic anhydride of Formula 5 to provide the Formula 2 benzoxazinone directly.

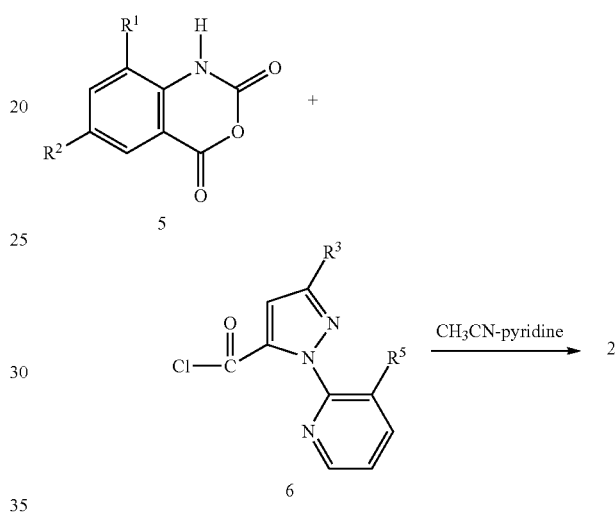

Solvents such as pyridine or pyridine/acetonitrile are suitable for this reaction. The acid chlorides of Formula 6 are available from the corresponding acids of Formula 4 by known methods such as chlorination with thionyl chloride or oxalyl chloride.

Anthranilic acids of Formula 3 are available by a variety of known methods. Many of these compounds are known. As shown in Scheme 4, anthranilic acids containing an $R^2$ substituent of chloro, bromo or iodo can be prepared by direct halogenation of an unsubstituted anthranilic acid of Formula 7 with N-chlorosuccinimide (NCS), N-bromosuccinimide (NBS) or N-iodosuccinimide (NIS) respectively in solvents such as N,N-dimethylformamide (DMF) to produce the corresponding substituted acid of Formula 3.

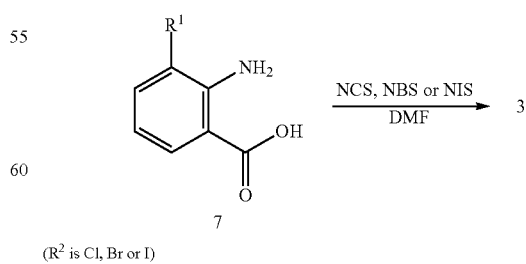

($R^2$ is Cl, Br or I)

Preparation of the isatoic anhydrides of Formula 5 can be achieved from isatins of Formula 9 as outlined in Scheme 5.

Scheme 5

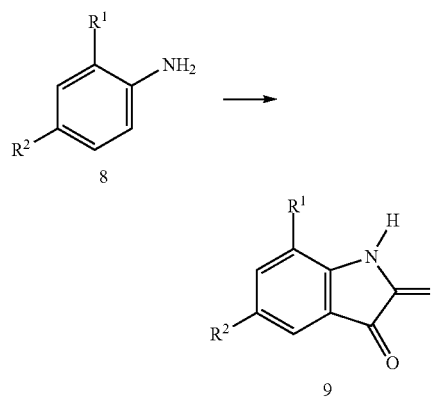

Isatins of Formula 9 are available from aniline derivatives of Formula 8 following literature procedures such as F. D. Popp, *Adv. Heterocycl. Chem.* 1975, 18, 1-58 and J. F. M. Da Silva et al., *Journal of the Brazilian Chemical Society* 2001, 12(3), 273-324. Oxidation of isatin 9 with hydrogen peroxide generally affords good yields of the corresponding isatoic anhydride 5 (G. Reissenweber and D. Mangold, *Angew. Chem. Int. Ed. Engl.* 1980, 19, 222-223). Isatoic anhydrides are also available from the anthranilic acids 3 via many known procedures involving reaction of 3 with phosgene or a phosgene equivalent.

Pyrazolecarboxylic acids of Formula 4 can be prepared by the method outlined in Scheme 6.

Scheme 6

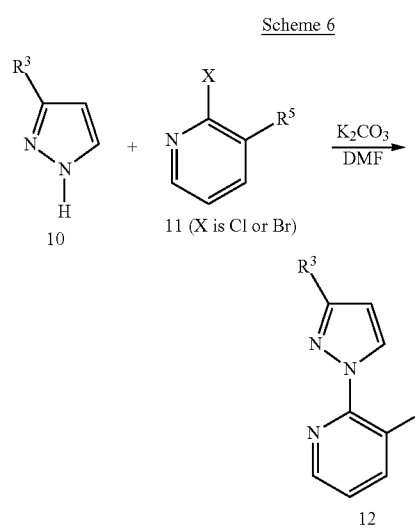

Reaction of pyrazole 10 with a 2,3-dihalopyridine of Formula 11 affords good yields of the 1-pyridylpyrazole 12 with good specificity for the desired regiochemistry. Metallation of 12 with lithium diisopropylamide (LDA) followed by quenching of the lithium salt with carbon dioxide affords the pyrazolecarboxylic acid of Formula 4. Additional procedural details for this method are provided in Examples 1, 3 and 5.

The starting pyrazoles 10 wherein $R^3$ is $CF_3$, Cl or Br are known compounds. Pyrazole 10 wherein $R^3$ is $CF_3$ is commercially available. Pyrazoles 10 wherein $R^3$ is Cl or Br can be prepared by literature procedures (H. Reimlinger and A. Van Overstraeten, *Chem. Ber.* 1966, 99(10), 3350-7). A useful alternative method for the preparation of 10 wherein $R^3$ is Cl or Br is depicted in Scheme 7.

Scheme 7

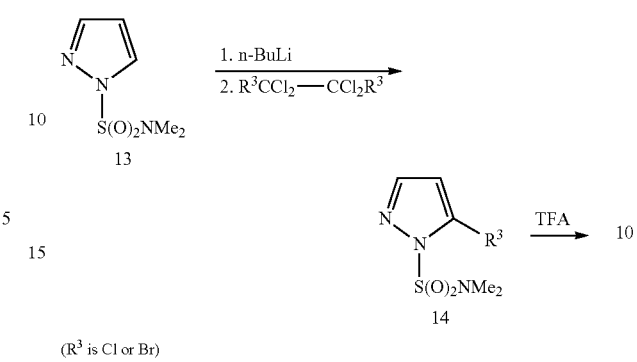

($R^3$ is Cl or Br)

Metallation of the sulfamoyl pyrazole 13 with n-butyllithium followed by direct halogenation of the anion with either hexachloroethane (for $R^3$ being Cl) or 1,2-dibromo-tetrachloroethane (for $R^3$ being Br) affords the halogenated derivatives 14. Removal of the sulfamoyl group with trifluoroacetic acid (TFA) at room temperature proceeds cleanly and in good yield to afford the pyrazoles 10 wherein $R^3$ is Cl or Br respectively. Further experimental details for this method are described in Examples 3 and 5.

As an alternative to the method illustrated in Scheme 6, pyrazolecarboxylic acids of Formula 4 wherein $R^3$ is $CF_3$ can also be prepared by the method outlined in Scheme 8.

Scheme 8

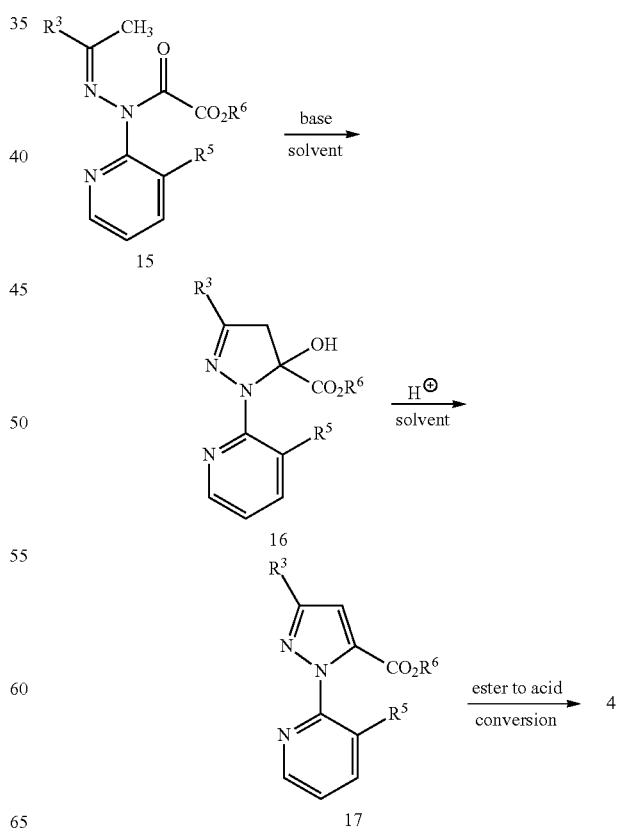

Reaction of a compound of Formula 15 wherein $R^6$ is $C_1$-$C_4$ alkyl with a suitable base in a suitable organic solvent affords the cyclized product of Formula 16 after neutralization with an acid such as acetic acid. The suitable base can be, for example but not limitation, sodium hydride, potassium t-butoxide, dimsyl sodium ($CH_3S(O)CH_2^-$, $Na^+$), alkali metal (such as lithium, sodium or potassium) carbonates or hydroxides, tetraalkyl (such as methyl, ethyl or butyl)ammonium fluorides or hydroxides, or 2-tert-butylimino-2-diethylamino-1,3-dimethyl-perhydro-1,3,2-diazaphosphonine.

The suitable organic solvent can be, for example but not limitation, acetone, acetonitrile, tetrahydrofuran, dichloromethane, dimethylsulfoxide, or N,N-dimethylformamide. The cyclization reaction is usually conducted in a temperature range from about 0 to 120° C. The effects of solvent, base, temperature and addition time are all interdependent, and choice of reaction conditions is important to minimize the formation of byproducts. A preferred base is tetrabutylammonium fluoride.

Dehydration of the compound of Formula 16 to give the compound of Formula 17, followed by converting the carboxylic ester function to carboxylic acid, affords the compound of Formula 4. The dehydration is effected by treatment with a catalytic amount of a suitable acid. This catalytic acid can be, for example but not limitation, sulfuric acid. The reaction is generally conducted using an organic solvent. As one skilled in the art will realize, dehydration reactions may be conducted in a wide variety of solvents in a temperature range generally between about 0 and 200° C., more preferably between about 0 and 100° C.). For the dehydration in the method of Scheme 8, a solvent comprising acetic acid and temperatures of about 65° C. are preferred. Carboxylic ester compounds can be converted to carboxylic acid compounds by numerous methods including nucleophilic cleavage under anhydrous conditions or hydrolytic methods involving the use of either acids or bases (see T. W. Greene and P. G. M. Wuts, *Protective Groups in Organic Synthesis,* 2nd ed., John Wiley & Sons, Inc., New York, 1991, pp. 224-269 for a review of methods). For the method of Scheme 8, base-catalyzed hydrolytic methods are preferred. Suitable bases include alkali metal (such as lithium, sodium or potassium) hydroxides. For example, the ester can be dissolved in a mixture of water and an alcohol such as ethanol. Upon treatment with sodium hydroxide or potassium hydroxide, the ester is saponified to provide the sodium or potassium salt of the carboxylic acid. Acidification with a strong acid, such as hydrochloric acid or sulfuric acid, yields the carboxylic acid of Formula 4. The carboxylic acid can be isolated by methods known to those skilled in the art, including crystallization, extraction and distillation.

Compounds of Formula 15 can be prepared by the method outlined in Scheme 9.

Scheme 9

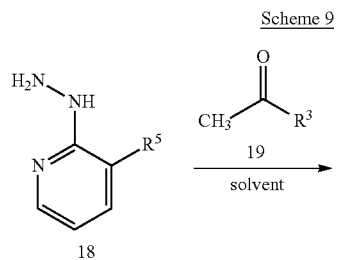

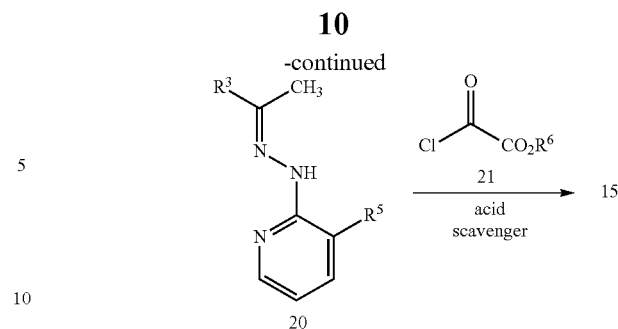

wherein $R^3$ is $CF_3$ and $R^6$ is $C_1$-$C_4$ alkyl.

Treatment of a hydrazine compound of Formula 18 with a ketone of Formula 19 in a solvent such as water, methanol or acetic acid gives the hydrazone of Formula 20. One skilled in the art will recognize that this reaction may require catalysis by an optional acid and may also require elevated temperatures depending on the molecular substitution pattern of the hydrazone of Formula 20. Reaction of the hydrazone of Formula 20 with the compound of Formula 21 in a suitable organic solvent such as, for example but not limitation, dichloromethane or tetrahydrofuran in the presence of an acid scavenger such as triethylamine provides the compound of Formula 15. The reaction is usually conducted at a temperature between about 0 and 100° C. Further experimental details for the method of Scheme 9 are illustrated in Example 7. Hydrazine compounds of Formula 18 can be prepared by standard methods, such as by contacting the corresponding halo compound of Formula 11 with hydrazine.

As an alternative to the method illustrated in Scheme 6, pyrazolecarboxylic acids of Formula 4 wherein $R^3$ is Cl or Br can also be prepared by the method outlined in Scheme 10.

Scheme 10

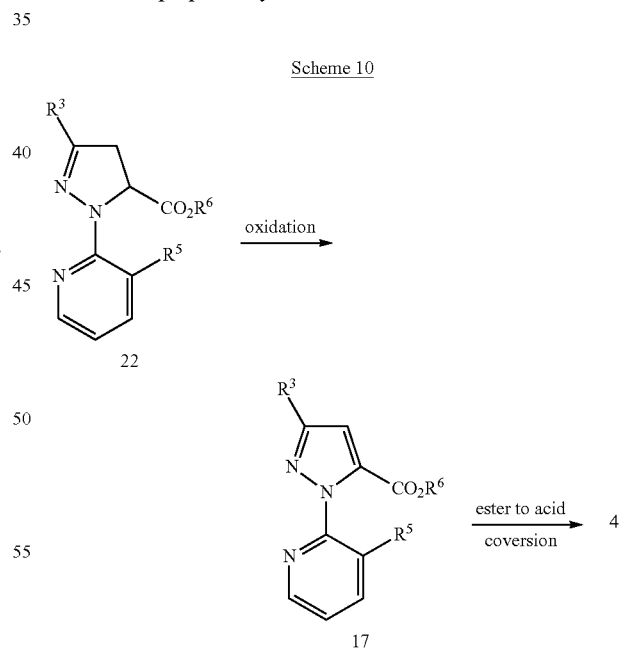

wherein $R^6$ is $C_1$-$C_4$ alkyl.

Oxidization of the compound of Formula 22 optionally in the presence of acid to give the compound of Formula 17 followed by conversion of the carboxylic ester function to the carboxylic acid provides the compound of Formula 4. The oxidizing agent can be hydrogen peroxide, organic peroxides, potassium persulfate, sodium persulfate, ammonium persulfate, potassium monopersulfate (e.g., Oxone®) or potassium permanganate. To obtain complete conversion, at least one equivalent of oxidizing agent versus the compound of Formula 22 should be used, preferably between about one to two equivalents. This oxidation is typically carried out in the presence of a solvent. The solvent can be an ether, such as tetrahydrofuran, p-dioxane and the like, an organic ester, such as ethyl acetate, dimethyl carbonate and the like, or a polar aprotic organic such as N,N-dimethylformamide, acetonitrile and the like. Acids suitable for use in the oxidation step include inorganic acids, such as sulfuric acid, phosphoric acid and the like, and organic acids, such as acetic acid, benzoic acid and the like. The acid, when used, should be used in greater than 0.1 equivalents versus the compound of Formula 22. To obtain complete conversion, one to five equivalents of acid can be used. The preferred oxidant is potassium persulfate and the oxidation is preferably carried out in the presence of sulfuric acid. The reaction can be carried out by mixing the compound of Formula 22 in the desired solvent and, if used, the acid. The oxidant can then be added at a convenient rate. The reaction temperature is typically varied from as low as about 0° C. up to the boiling point of the solvent in order to obtain a reasonable reaction time to complete the reaction, preferably less than 8 hours. The desired product, a compound of Formula 17 can be isolated by methods known to those skilled in the art, including crystallization, extraction and distillation. Methods suitable for converting the ester of Formula 17 to the carboxylic acid of Formula 4 are already described for Scheme 8. Further experimental details for the method of Scheme 10 are illustrated in Examples 8 and 9.

Compounds of Formula 22 can be prepared from corresponding compounds of Formula 23 as shown in Scheme 11.

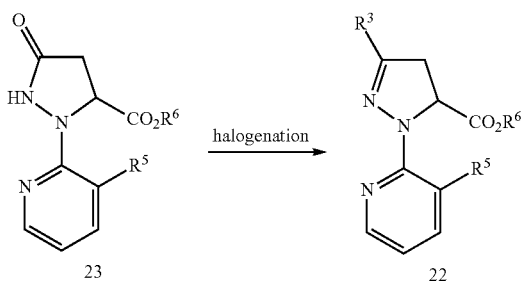

Scheme 11 wherein $R^6$ is $C_1$-$C_4$ alkyl.

Treatment of a compound of Formula 23 with a halogenating reagent, usually in the presence of a solvent, affords the corresponding halo compound of Formula 22. Halogenating reagents that can be used include phosphorus oxyhalides, phosphorus trihalides, phosphorus pentahalides, thionyl chloride, dihalotrialkylphophoranes, dihalodiphenylphosphoranes, oxalyl chloride and phosgene. Preferred are phosphorus oxyhalides and phosphorus pentahalides. To obtain complete conversion, at least 0.33 equivalents of phosphorus oxyhalide versus the compound of Formula 23 should be used, preferably between about 0.33 and 1.2 equivalents. To obtain complete conversion, at least 0.20 equivalents of phosphorus pentahalide versus the compound of Formula 23 should be used, preferably between about 0.20 and 1.0 equivalents. Compounds of Formula 23 wherein $R^6$ is $C_1$-$C_4$ alkyl are preferred for this reaction. Typical solvents for this halogenation include halogenated alkanes, such as dichloromethane, chloroform, chlorobutane and the like, aromatic solvents, such as benzene, xylene, chlorobenzene and the like, ethers, such as tetrahydrofuran, p-dioxane, diethyl ether, and the like, and polar aprotic solvents such as acetonitrile, N,N-dimethylformamide, and the like. Optionally, an organic base, such as triethylamine, pyridine, N,N-dimethylaniline or the like, can be added. Addition of a catalyst, such as N,N-dimethylformamide, is also an option. Preferred is the process in which the solvent is acetonitrile and a base is absent. Typically, neither a base nor a catalyst is required when acetonitrile solvent is used. The preferred process is conducted by mixing the compound of Formula 23 in acetonitrile. The halogenating reagent is then added over a convenient time, and the mixture is then held at the desired temperature until the reaction is complete. The reaction temperature is typically between 20° C. and the boiling point of acetonitrile, and the reaction time is typically less than 2 hours. The reaction mass is then neutralized with an inorganic base, such as sodium bicarbonate, sodium hydroxide and the like, or an organic base, such as sodium acetate. The desired product, a compound of Formula 22, can be isolated by methods known to those skilled in the art, including crystallization, extraction and distillation.

Alternatively, compounds of Formula 22 wherein $R^3$ is Br or Cl can be prepared by treating the corresponding compounds of Formula 22 wherein $R^3$ is a different halogen (e.g., Cl for making Formula 22 wherein $R^3$ is Br) or a sulfonate group such as p-toluenesulfonate, benzenesulfonate and methanesulfonate with hydrogen bromide or hydrogen chloride, respectively. By this method the $R^3$ halogen or sulfonate substituent on the Formula 22 starting compound is replaced with Br or Cl from hydrogen bromide or hydrogen chloride, respectively. The reaction is conducted in a suitable solvent such as dibromomethane, dichloromethane or acetonitrile. The reaction can be conducted at or near atmospheric pressure or above atmospheric pressure in a pressure vessel. When $R^3$ in the starting compound of Formula 22 is a halogen such as Cl, the reaction is preferably conducted in such a way that the hydrogen halide generated from the reaction is removed by sparging or other suitable means. The reaction can be conducted between about 0 and 100° C., most conveniently near ambient temperature (e.g., about 10 to 40° C.), and more preferably between about 20 and 30° C. Addition of a Lewis acid catalyst (such as aluminum tribromide for preparing Formula 22 wherein $R^3$ is Br) can facilitate the reaction. The product of Formula 22 is isolated by the usual methods known to those skilled in the art, including extraction, distillation and crystallization. Further details for this process are illustrated in Example 10.

Starting compounds of Formula 22 wherein $R^3$ is Cl or Br can be prepared from corresponding compounds of Formula 23 as already described. Starting compounds of Formula 22 wherein $R^3$ is a sulfonate group can likewise be prepared from corresponding compounds of Formula 23 by standard methods such as treatment with a sulfonyl chloride (e.g., p-toluenesulfonyl chloride) and base such as a tertiary amine (e.g., triethylamine) in a suitable solvent such as dichloromethane; further details for this process are illustrated in Example 11.

As an alternative to the method illustrated in Scheme 6, pyrazolecarboxylic acids of Formula 4 wherein $R^3$ is $OCH_2CF_3$ can also be prepared by the method outlined in Scheme 12.

Scheme 12

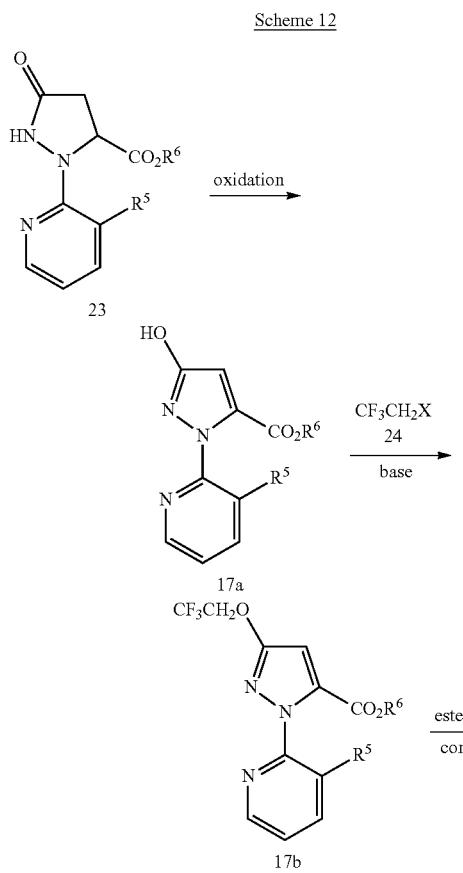

wherein $R^6$ is $C_1$-$C_4$ alkyl, and X is a leaving group.

In this method, instead of being halogenated as shown in Scheme 11, the compound of Formula 23 is oxidized to the compound of Formula 17a. The reaction conditions for this oxidation are as already described for the conversion of the compound of Formula 22 to the compound of Formula 17 in Scheme 10.

The compound of Formula 17a is then alkylated to form the compound of Formula 17b by contact with an alkylating agent $CF_3CH_2X$ (24) in the presence of a base. In the alkylating agent 24, X is a nucleophilic reaction leaving group such as halogen (e.g., Br, I), $OS(O)_2CH_3$ (methanesulfonate), $OS(O)_2CF_3$, $OS(O)_2Ph$-p-$CH_3$ (p-toluenesulfonate), and the like; methanesulfonate works well. The reaction is conducted in the presence of at least one equivalent of a base. Suitable bases include inorganic bases, such as alkali metal (such as lithium, sodium or potassium) carbonates and hydroxides, and organic bases, such as triethylamine, diisopropylethylamine and 1,8-diazabicyclo[5.4.0]undec-7-ene. The reaction is generally conducted in a solvent, which can comprise alcohols, such as methanol and ethanol, halogenated alkanes, such as dichloromethane, aromatic solvents, such as benzene, toluene and chlorobenzene, ethers, such as tetrahydrofuran, and polar aprotic solvents, such as acetonitrile, such as such as acetonitrile, N,N-dimethylformamide, and the like. Alcohols and polar aprotic solvents are preferred for use with inorganic bases. Potassium carbonate as base and acetonitrile as solvent are preferred. The reaction is generally conducted between about 0 and 150° C., with most typically between ambient temperature and 100° C. The product of Formula 17b can be isolated by conventional techniques such as extraction.

The ester of Formula 17b can then be converted to the carboxylic acid of Formula 4 by the methods already described for the conversion of Formula 17 to Formula 4 in Scheme 8. Further experimental details for the method of Scheme 12 are illustrated in Example 12.

Compounds of Formula 23 can be prepared from compounds of Formula 18 as outlined in Scheme 13.

Scheme 13

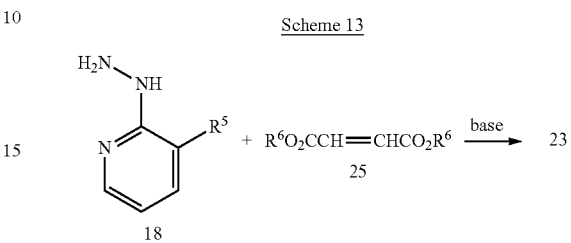

wherein $R^6$ is $C_1$-$C_4$ alkyl.

In this method, a hydrazine compound of Formula 18 is contacted with a compound of Formula 25 (a fumarate ester or maleate ester or a mixture thereof may be used) in the presence of a base and a solvent. The base is typically a metal alkoxide salt, such as sodium methoxide, potassium methoxide, sodium ethoxide, potassium ethoxide, potassium tert-butoxide, lithium tert-butoxide, and the like. Greater than 0.5 equivalents of base versus the compound of Formula 18 should be used, preferably between 0.9 and 1.3 equivalents. Greater than 1.0 equivalents of the compound of Formula 25 should be used, preferably between 1.0 to 1.3 equivalents. Polar protic and polar aprotic organic solvents can be used, such as alcohols, acetonitrile, tetrahydrofuran, N,N-dimethylformamide, dimethyl sulfoxide and the like. Preferred solvents are alcohols such as methanol and ethanol. It is especially preferred that the alcohol be the same as that making up the fumarate or maleate ester and the alkoxide base. The reaction is typically conducted by mixing the compound of Formula 18 and the base in the solvent. The mixture can be heated or cooled to a desired temperature and the compound of Formula 25 added over a period of time. Typically reaction temperatures are between 0° C. and the boiling point of the solvent used. The reaction may be conducted under greater than atmospheric pressure in order to increase the boiling point of the solvent. Temperatures between about 30 and 90° C. are generally preferred. The addition time can be as quick as heat transfer allows. Typical addition times are between 1 minute and 2 hours. Optimum reaction temperature and addition time vary depending upon the identities of the compounds of Formula 18 and Formula 25. After addition, the reaction mixture can be held for a time at the reaction temperature. Depending upon the reaction temperature, the required hold time may be from 0 to 2 hours. Typical hold times are 10 to 60 minutes. The reaction mass then can be acidified by adding an organic acid, such as acetic acid and the like, or an inorganic acid, such as hydrochloric acid, sulfuric acid and the like. Depending on the reaction conditions and the means of isolation, the —$CO_2R^6$ function on the compound of Formula 23 may be hydrolyzed to —$CO_2H$; for example, the presence of water in the reaction mixture can promote such hydrolysis. If the carboxylic acid (—$CO_2H$) is formed, it can be converted back to —$CO_2R^6$ wherein $R^6$ is $C_1$-$C_4$ alkyl using esterification methods well-known in the art. The desired product, a compound of Formula 23, can be isolated by methods known to those skilled in the art, such as crystallization, extraction or distillation.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, T. W. Greene and P. G. M. Wuts, *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

It is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets, and "br s" means broad singlet.

EXAMPLE 1

Preparation of N-[4-chloro-2-methyl-6-[[(1-methylethyl)amino]carbonyl]phenyl]-1-(3-chloro-2-pyridinyl)-3-(trifluoromethyl)-1H-pyrazole-5-carboxamide Step A: Preparation of 2-amino-3-methyl-5-chlorobenzoic acid To a solution of 2-amino-3-methylbenzoic acid (Aldrich, 15.0 g, 99.2 mmol) in N,N-dimethylformamide (50 mL) was added N-chlorosuccinimide (13.3 g, 99.2 mmol) and the reaction mixture was heated to 100° C. for 30 minutes. The heat was removed, the reaction was cooled to room temperature and let stand overnight. The reaction mixture was then slowly poured into ice-water (250 mL) to precipitate a white solid. The solid was filtered and washed four times with water and then taken up in ethyl acetate (900 mL). The ethyl acetate solution was dried over magnesium sulfate, evaporated under reduced pressure and the residual solid was washed with ether to afford the desired intermediate as a white solid (13.9 g).

$^1$H NMR (DMSO-$d_6$) δ 2.11 (s, 3H), 7.22 (s, 1H), 7.55 (s, 1H).

Step B: Preparation of 3-chloro-2-[3-(trifluoromethyl)-1H-pyrazol-1-yl]pyridine

To a mixture of 2,3-dichloropyridine (99.0 g, 0.67 mol) and 3-(trifluoromethyl)-pyrazole (83 g, 0.61 mol) in dry N,N-dimethylformamide (300 mL) was added potassium carbonate (166.0 g, 1.2 mol) and the reaction was then heated to 110-125° C. over 48 hours. The reaction was cooled to 100° C. and filtered through Celite® diatomaceous filter aid to remove solids. N,N-Dimethylformamide and excess dichloropyridine were removed by distillation at atmospheric pressure. Distillation of the product at reduced pressure (b.p. 139-141° C., 7 mm) afforded the desired intermediate as a clear yellow oil (113.4 g).

$^1$H NMR (CDCl$_3$) δ 6.78 (s, 1H), 7.36 (t, 1H), 7.93 (d, 1H), 8.15 (s, 1H), 8.45 (d, 1H).

Step C: Preparation of 1-(3-chloro-2-pyridinyl)-3-(trifluoromethyl)-1H-pyrazole-5-carboxylic acid To a solution of 3-chloro-2-[3-(trifluoromethyl)-1H-pyrazol-1-yl]pyridine (i.e. the pyrazole product from Step B) (105.0 g, 425 mmol) in dry tetrahydrofuran (700 mL) at −75° C. was added via cannula a −30° C. solution of lithium diisopropylamide (425 mmol) in dry tetrahydrofuran (300 mL). The deep red solution was stirred for 15 minutes, after which time carbon dioxide was bubbled through at −63° C. until the solution became pale yellow and the exothermicity ceased. The reaction was stirred for an additional 20 minutes and then quenched with water (20 mL). The solvent was removed under reduced pressure, and the reaction mixture partitioned between ether and 0.5 N aqueous sodium hydroxide solution. The aqueous extracts were washed with ether (3×), filtered through Celite® diatomaceous filter aid to remove residual solids, and then acidified to a pH of approximately 4, at which point an orange oil formed. The aqueous mixture was stirred vigorously and additional acid was added to lower the pH to 2.5-3. The orange oil congealed into a granular solid, which was filtered, washed successively with water and 1 N hydrochloric acid, and dried under vacuum at 50° C. to afford the title product as an off-white solid (130 g). (Product from another run following similar procedure melted at 175-176° C.)

$^1$H NMR (DMSO-$d_6$) δ 7.61 (s, 1H), 7.76 (dd, 1H), 8.31 (d, 1H), 8.60 (d, 1H).

Step D: Preparation of 6-chloro-2-[1-(3-chloro-2-pyridinyl)-3-(trifluoromethyl)-1H-pyrazol-5-yl]-8-methyl-4H-3,1-benzoxazin-4-one To a solution of methanesulfonyl chloride (2.2 mL, 28.3 mmol) in acetonitrile (75 mL) was added dropwise a mixture of 1-(3-chloro-2-pyridinyl)-3-(trifluoromethyl)-1H-pyrazole-5-carboxylic acid (i.e. the carboxylic acid product of Step C) (7.5 g, 27.0 mmol) and triethylamine (3.75 mL, 27.0 mmol) in acetonitrile (75 mL) at 0-5° C. The reaction temperature was then maintained at 0° C. throughout successive addition of reagents. After stirring for 20 minutes, 2-amino-3-methyl-5-chlorobenzoic acid (i.e. the product from Step A) (5.1 g, 27.0 mmol) was added and stirring was continued for an additional 5 minutes. A solution of triethylamine (7.5 mL, 54.0 mmol) in acetonitrile (15 mL) was then added dropwise, and the reaction mixture was stirred 45 minutes, followed by the addition of methanesulfonyl chloride (2.2 mL, 28.3 mmol). The reaction mixture was then warmed to room temperature and stirred overnight. Approximately 75 mL of water was then added to precipitate 5.8 g of a yellow solid. An additional 1 g of product was isolated by extraction from the filtrate to provide a total of 6.8 g of the title compound as a yellow solid.

$^1$H NMR (CDCl$_3$) δ 1.83 (s, 3H), 7.50 (s, 1H), 7.53 (m, 2H), 7.99 (m, 2H), 8.58 (d, 1H).

Step E: Preparation of N-[4-chloro-2-methyl-6-[[(1-methylethyl)amino]carbonyl]-phenyl]-1-(3-chloro-2-pyridinyl)-3-(trifluoromethyl)-1H-pyrazole-5-carboxamide To a solution of 6-chloro-2-[1-(3-chloro-2-pyridinyl)-3-(trifluoromethyl)-1H-pyrazol-5-yl]-8-methyl-4H-3,1-benzoxazin-4-one (i.e. the benzoxazinone product of Step D) (5.0 g, 11.3 mmol) in tetrahydrofuran (35 mL) was added dropwise isopropylamine (2.9 mL, 34.0 mmol) in tetrahydrofuran (10 mL) at room temperature. The reaction mixture was then warmed until all solids had dissolved and stirred an additional five minutes, at which point thin layer chromatography on silica gel confirmed completion of the reaction. The tetrahydrofuran solvent was evaporated under reduced pressure, and the residual solid was purified by chromatography on silica gel, followed by trituration with ether/hexane to afford the title compound, a compound of the present invention, as a solid (4.6 g), melting at 195-196° C.

$^1$H NMR (CDCl$_3$) δ 1.21 (d, 6H), 2.17 (s, 3H), 4.16 (m, 1H), 5.95 (br d, 1H), 7.1-7.3 (m, 2H), 7.39 (s, 1H), 7.4 (m, 1H), 7.84 (d, 1H), 8.50 (d, 1H), 10.24 (br s, 1H).

EXAMPLE 2

Preparation of N-[4-chloro-2-methyl-6-[(methylamino)carbonyl]phenyl]-1-(3-chloro-2-pyridinyl)-3-(trifluoromethyl)-1H-pyrazole-5-carboxamide To a solution of 6-chloro-2-[1-(3-chloro-2-pyridinyl)-3-(trifluoromethyl)-1H-pyrazol-5-yl]-8-methyl-4H-3,1-benzoxazin-4-one (i.e. the benzoxazinone product of Example 1, Step D) (4.50 g, 10.18 mmol) in tetrahydrofuran (THF; 70 mL) was added methylamine (2.0 M solution in THF, 15 mL, 30.0 mmol) dropwise and the reaction mixture was stirred at room temperature for 5 minutes. The tetrahydrofuran solvent was evaporated under reduced pressure and the residual solid was purified by chromatography on silica gel to afford 4.09 g of the title compound, a compound of the present invention, as a white solid melting at 185-186° C.

$^1$H NMR (DMSO-d$_6$) δ 2.17 (s, 3H), 2.65 (d, 3H), 7.35 (d, 1H), 7.46 (dd, 1H), 7.65 (dd, 1H), 7.74 (s, 1H), 8.21 (d, 1H), 8.35 (br q, 1H), 8.74 (d, 1H), 10.39 (s, 1H).

EXAMPLE 3

Preparation of 3-chloro-N-[4-chloro-2-methyl-6-[[(1-methylethyl)amino]carbonyl]phenyl]-1-(3-chloro-2-pyridinyl)-1H-pyrazole-5-carboxamide Step A: Preparation of 3-chloro-N,N-dimethyl-1H-pyrazole-1-sulfonamide To a solution of N-dimethylsulfamoylpyrazole (188.0 g, 1.07 mol) in dry tetrahydrofuran (1500 mL) at −78° C. was added dropwise a solution of 2.5 M n-butyl-lithium (472 mL, 1.18 mol) in hexane while maintaining the temperature below −65° C. Upon completion of the addition the reaction mixture was maintained at −78° C. for an additional 45 minutes, after which time a solution of hexachloroethane (279 g, 1.18 mol) in tetrahydrofuran (120 mL) was added dropwise. The reaction mixture was maintained for an hour at −78° C., warmed to −20° C. and then quenched with water (1 L). The reaction mixture was extracted with methylene chloride (4×500 mL); the organic extracts were dried over magnesium sulfate and concentrated. The crude product was further purified by chromatography on silica gel using methylene chloride as eluent to afford the title product compound as a yellow oil (160 g).

$^1$H NMR (CDCl$_3$) δ 3.07 (d, 6H), 6.33 (s, 1H), 7.61 (s, 1H).

Step B: Preparation of 3-chloropyrazole

To trifluoroacetic acid (290 mL) was added dropwise 3-chloro-N,N-dimethyl-1H-pyrazole-1-sulfonamide (i.e. the chloropyrazole product of Step A) (160 g), and the reaction mixture was stirred at room temperature for 1.5 hrs and then concentrated at reduced pressure. The residue was taken up in hexane, insoluble solids were filtered off, and the hexane was concentrated to afford the crude product as an oil. The crude product was further purified by chromatography on silica gel using ether/hexane (40:60) as eluent to afford the title product as a yellow oil (64.44 g).

$^1$H NMR (CDCl$_3$) δ 6.39 (s, 1H), 7.66 (s, 1H), 9.6 (br s, 1H).

Step C: Preparation of 3-chloro-2-(3-chloro-1H-pyrazol-1-yl)pyridine

To a mixture of 2,3-dichloropyridine (92.60 g, 0.629 mol) and 3-chloropyrazole (i.e. the product of Step B) (64.44 g, 0.629 mol) in N,N-dimethylformamide (400 mL) was added potassium carbonate (147.78 g, 1.06 mol), and the reaction mixture was then heated to 100° C. for 36 hours. The reaction mixture was cooled to room temperature and slowly poured into ice water. The precipitated solids were filtered and washed with water. The solid filter cake was taken up in ethyl acetate, dried over magnesium sulfate and concentrated. The crude solid was chromatographed on silica gel using 20% ethyl acetate/hexane as eluent to afford the title product as a white solid (39.75 g).

$^1$H NMR (CDCl$_3$) δ 6.43 (s, 1H), 7.26 (m, 1H), 7.90 (d, 1H), 8.09 (s, 1H), 8.41 (d, 1H).

Step D: Preparation of 3-chloro-1-(3-chloro-2-pyridinyl)-1H-pyrazole-5-carboxylic acid To a solution of 3-chloro-2-(3-chloro-1H-pyrazol-1-yl)pyridine (i.e. the pyrazole product of Step C) (39.75 g, 186 mmol) in dry tetrahydrofuran (400 mL) at −78° C. was added dropwise a solution of 2.0 M lithium diisopropylamide (93 mL, 186 mmol) in tetrahydrofuran. Carbon dioxide was bubbled through the amber solution for 14 minutes, after which time the solution became pale brownish-yellow. The reaction was made basic with 1 N aqueous sodium hydroxide solution and extracted with ether (2×500 mL). The aqueous extracts were acidified with 6 N hydrochloric acid and extracted with ethyl acetate (3×500 mL). The ethyl acetate extracts were dried over magnesium sulfate and concentrated to afford the title product as an off-white solid (42.96 g). (Product from another run following a similar procedure melted at 198-199° C.)

$^1$H NMR (DMSO-d$_6$) δ 6.99 (s, 1H), 7.45 (m, 1H), 7.93 (d, 1H), 8.51 (d, 1H).

Step E: Preparation of 6-chloro-2-[3-chloro-1-(3-chloro-2-pyridinyl)-1H-pyrazol-5-yl]-8-methyl-4H-3,1-benzoxazin-4-one To a solution of methanesulfonyl chloride (6.96 g, 61.06 mmol) in acetonitrile (150 mL) was added dropwise a mixture of 3-chloro-1-(3-chloro-2-pyridinyl)-1H-pyrazole-5-carboxylic acid (i.e. the carboxylic acid product of Step D) (15.0 g, 58.16 mmol) and triethylamine (5.88 g, 58.16 mmol) in acetonitrile (150 mL) at −5° C. The reaction mixture was then stirred for 30 minutes at 0° C. Then, 2-amino-3-methyl-5-chlorobenzoic acid (i.e. the product from Example 1, Step A) (10.79 g, 58.16 mmol) was added, and stirring was continued for an additional 10 minutes. A solution of triethylamine (11.77 g, 116.5 mmol) in acetonitrile was then added dropwise while keeping the temperature below 10° C. The reaction mixture was stirred 60 minutes at 0° C., and then methanesulfonyl chloride (6.96 g, 61.06 mmol) was added. The reaction mixture was then warmed to room temperature and stirred for an additional 2 hours. The reaction mixture was then concentrated, and the crude product was chromatographed on silica gel using methylene chloride as eluent to afford the title product as a yellow solid (9.1 g).

$^1$H NMR (CDCl$_3$) δ 1.81 (s, 3H), 7.16 (s, 1H), 7.51 (m, 2H), 7.98 (d, 2H), 8.56 (d, 1H).

Step F: Preparation of 3-chloro-N-[4-chloro-2-methyl-6-[[(1-methylethyl)amino]-carbonyl]phenyl]-1-(3-chloro-2-pyridinyl)-1H-pyrazole-5-carboxamide To a solution of 6-chloro-2-[3-chloro-1-(3-chloro-2-pyridinyl)-1H-pyrazol-5-yl]-8-methyl-4H-3,1-benzoxazin-4-one (e.g, the benzoxazinone product of Step E) (6.21 g, 15.21 mmol) in tetrahydrofuran (100 mL) was added isopropylamine (4.23 g, 72.74 mmol) and the reaction mixture was then heated to 60° C., stirred for 1 hour and then cooled to room temperature. The tetrahydrofuran solvent was evaporated under reduced pressure, and the residual solid was purified by chromatography on silica gel to afford the title compound, a compound of the present invention, as a white solid (5.05 g) melting at 173-175° C. $^1$H NMR (CDCl$_3$) δ 1.23 (d, 6H), 2.18 (s, 3H), 4.21 (m, 1H), 5.97 (d, 1H), 7.01 (m, 1H), 7.20 (s, 1H), 7.24 (s, 1H), 7.41 (d, 1H), 7.83 (d, 1H), 8.43 (d, 1H), 10.15 (br s, 1H).

EXAMPLE 4

Preparation of 3-chloro-N-[4-chloro-2-methyl-6-[(methylamino)carbonyl]phenyl]-1-(3-chloro-2-pyridinyl)-1H-pyrazole-5-carboxamide To a solution of 6-chloro-2-[3-chloro-1-(3-chloro-2-pyridinyl)-1H-pyrazol-5-yl]-8-methyl-4H-3,1-benzoxazin-4-one (i.e. the benzoxazinone product of Example 3, Step E) (6.32 g, 15.47 mmol) in tetrahydrofuran (50 mL) was added methylamine (2.0 M solution in THF, 38 mL, 77.38 mmol), and the reaction mixture was heated to 60° C., stirred for 1 hour and then cooled to room temperature. The tetrahydrofuran solvent was evaporated under reduced pressure, and the residual solid was purified by chromatography on silica gel to afford the title compound, a compound of the present invention, as a white solid (4.57 g) melting at 225-226° C.

$^1$H NMR (CDCl$_3$) δ 2.15 (s, 3H), 2.93 (s, 3H), 6.21 (d, 1H), 7.06 (s, 1H), 7.18 (s, 1H), 7.20 (s, 1H), 7.42 (m, 1H), 7.83 (d, 1H), 8.42 (d, 1H), 10.08 (br s, 1H).

EXAMPLE 5

Preparation of 3-bromo-N-[4-chloro-2-methyl-6-[[(1-methylethyl)amino]carbonyl]phenyl]-1-(3-chloro-2-pyridinyl)-1H-pyrazole-5-carboxamide Step A: Preparation of 3-bromo-N,N-dimethyl-1H-pyrazole-1-sulfonamide To a solution of N-dimethylsulfamoylpyrazole (44.0 g, 0.251 mol) in dry tetrahydrofuran (500 mL) at −78° C. was added dropwise a solution of n-butyllithium (2.5 M in hexane, 105.5 mL, 0.264 mol) while maintaining the temperature below −60° C. A thick solid formed during the addition. Upon completion of the addition the reaction mixture was maintained for an additional 15 minutes, after which time a solution of 1,2-dibromo-tetrachloroethane (90 g, 0.276 mol) in tetrahydrofuran (150 mL) was added dropwise while maintaining the temperature below −70° C. The reaction mixture turned a clear orange; stirring was continued for an additional 15 minutes. The −78° C. bath was removed and the reaction was quenched with water (600 mL). The reaction mixture was extracted with methylene chloride (4×), and the organic extracts were dried over magnesium sulfate and concentrated. The crude product was further purified by chromatography on silica gel using methylene chloride-hexane (50:50) as eluent to afford the title product as a clear colorless oil (57.04 g).

$^1$H NMR (CDCl$_3$) δ 3.07 (d, 6H), 6.44 (m, 1H), 7.62 (m, 1H).

Step B: Preparation of 3-bromopyrazole

To trifluoroacetic acid (70 mL) was slowly added 3-bromo-N,N-dimethyl-1H-pyrazole-1-sulfonamide (i.e. the bromopyrazole product of Step A) (57.04 g). The reaction mixture was stirred at room temperature for 30 minutes and then concentrated at reduced pressure. The residue was taken up in hexane, insoluble solids were filtered off, and the hexane was evaporated to afford the crude product as an oil. The crude product was further purified by chromatography on silica gel using ethyl acetate/dichloromethane (10:90) as eluent to afford an oil. The oil was taken up in dichloromethane, neutralized with aqueous sodium bicarbonate solution, extracted with methylene chloride (3×), dried over magnesium sulfate and concentrated to afford the title product as a white solid (25.9 g), m.p. 61-64° C.

$^1$H NMR (CDCl$_3$) δ 6.37 (d, 1H), 7.59 (d, 1H), 12.4 (br s, 1H).

Step C: Preparation of 2-(3-bromo-1H-pyrazol-1-yl)-3-chloropyridine

To a mixture of 2,3-dichloropyridine (27.4 g, 185 mmol) and 3-bromopyrazole (i.e. the product of Step B) (25.4 g, 176 mmol) in dry N,N-dimethylformamide (88 mL) was added potassium carbonate (48.6 g, 352 mmol), and the reaction mixture was heated to 125° C. for 18 hours. The reaction mixture was cooled to room temperature and poured into ice water (800 mL). A precipitate formed. The precipitated solids were stirred for 1.5 hrs, filtered and washed with water (2×100 mL). The solid filter cake was taken up in methylene chloride and washed sequentially with water, 1N hydrochloric acid, saturated aqueous sodium bicarbonate solution, and brine. The organic extracts were then dried over magnesium sulfate and concentrated to afford 39.9 g of a pink solid. The crude solid was suspended in hexane and stirred vigorously for 1 hr. The solids were filtered, washed with hexane and dried to afford the title product as an off-white powder (30.4 g) determined to be >94% pure by NMR. This material was used without further purification in Step D.

$^1$H NMR (CDCl$_3$) δ 6.52 (s, 1H), 7.30 (dd, 1H), 7.92 (d, 1H), 8.05 (s, 1H), 8.43 (d, 1H).

Step D: Preparation of 3-bromo-1-(3-chloro-2-pyridinyl)-1H-pyrazole-5-carboxylic acid To a solution of 2-(3-bromo-1H-pyrazol-1-yl)-3-chloropyridine (i.e. the pyrazole product of Step C) (30.4 g, 118 mmol)

in dry tetrahydrofuran (250 mL) at −76° C. was added dropwise a solution of lithium diisopropylamide (118 mmol) in tetrahydrofuran at such a rate as to maintain the temperature below −71° C. The reaction mixture was stirred for 15 minutes at −76° C., and carbon dioxide was then bubbled through for 10 minutes, causing warming to −57° C. The reaction mixture was warmed to −20° C. and quenched with water. The reaction mixture was concentrated and then taken up in water (1 L) and ether (500 mL), and then aqueous sodium hydroxide solution (1 N, 20 mL) was added. The aqueous extracts were washed with ether and acidified with hydrochloric acid. The precipitated solids were filtered, washed with water and dried to afford the title product as a tan solid (27.7 g). (Product from another run following similar procedure melted at 200-201° C.)

$^1$H NMR (DMSO-$d_6$) δ 7.25 (s, 1H), 7.68 (dd, 1H), 8.24 (d, 1H), 8.56 (d, 1H).

Step E: Preparation of 2-[3-bromo-1-(3-chloro-2-pyridinyl)-1H-pyrazol-5-yl]-6-chloro-8-methyl-4H-3,1-benzoxazin-4-one A procedure analogous to that of Example 1, Step E was used to convert 3-bromo-1-(3-chloro-2-pyridinyl)-1H-pyrazole-5-carboxylic acid (i.e. the pyrazolecarboxylic acid product of Example 5, Step D) (1.5 g, 4.96 mmol) and 2-amino-3-methyl-5-chlorobenzoic acid (i.e. the product of Example 1 Step A) (0.92 g, 4.96 mmol) to the title product as a solid (1.21 g).

$^1$H NMR (CDCl$_3$) δ 2.01 (s, 3H), 7.29 (s, 1H), 7.42 (d, 1H), 7.95 (d, 1H), 8.04 (m, 1H), 8.25 (s, 1H), 8.26 (d, 1H).

Step F: Preparation of 3-bromo-N-[4-chloro-2-methyl-6-[[(1-methylethyl)amino]-carbonyl]phenyl]-1-(3-chloro-2-pyridinyl)-1H-pyrazole-5-carboxamide To a solution of 2-[3-bromo-1-(3-chloro-2-pyridinyl)-1H-pyrazol-5-yl]-6-chloro-8-methyl-4H-3,1-benzoxazin-4-one (i.e. the benzoxazinone product of Step E) (0.20 g, 0.44 mmol) in tetrahydrofuran was added isopropylamine (0.122 mL, 1.42 mmol), and the reaction mixture was heated to 60° C. for 90 minutes and then cooled to room temperature. The tetrahydrofuran solvent was evaporated under reduced pressure, and the residual solid was triturated with ether, filtered, and dried to afford the title compound, a compound of the present invention, as a solid (150 mg), m.p. 159-161° C.

$^1$H NMR (CDCl$_3$) δ 1.22 (d, 6H), 2.19 (s, 3H), 4.21 (m, 1H), 5.99 (m, 1H), 7.05 (m, 1H), 7.22 (m, 2H), 7.39 (m, 1H), 7.82 (d, 1H), 8.41 (d, 1H).

EXAMPLE 6

Preparation of 3-bromo-N-[4-chloro-2-methyl-6-[(methylamino)carbonyl]phenyl]-1-(3-chloro-2-pyridinyl)-1H-pyrazole-5-carboxamide To a solution of 2-[3-bromo-1-(3-chloro-2-pyridinyl)-1H-pyrazol-5-yl]-6-chloro-8-methyl-4H-3,1-benzoxazin-4-one (i.e. the benzoxazinone product of Example 5, Step E) (0.20 g, 0.44 mmol) in tetrahydrofuran was added methylamine (2.0 M solution in THF, 0.514 mL, 1.02 mmol), and the reaction mixture was heated to 60° C. for 90 minutes and then cooled to room temperature. The tetrahydrofuran solvent was evaporated under reduced pressure, and the residual solid was triturated with ether, filtered, and dried to afford the title compound, a compound of the present invention, as a solid (40 mg), m.p. 162-164° C.

$^1$H NMR (CDCl$_3$) δ 2.18 (s, 3H), 2.95 (s, 3H), 6.21 (m, 1H), 7.10 (s, 1H), 7.24 (m, 2H), 7.39 (m, 1H), 7.80 (d, 1H), 8.45 (d, 1H).

The following Example 7 illustrates an alternative preparation of 1-(3-chloro-2-pyridinyl)-3-(trifluoromethyl)-1H-pyrazole-5-carboxylic acid, which can be used to prepare, for example, N-[4-chloro-2-methyl-6-[[(1-methylethyl)amino]carbonyl]phenyl]-1-(3-chloro-2-pyridinyl)-3-(trifluoromethyl)-1H-pyrazole-5-carboxamide and N-[4-chloro-2-methyl-6-[(methylamino)carbonyl]phenyl]-1-(3-chloro-2-pyridinyl)-3-(trifluoromethyl)-1H-pyrazole-5-carboxamide, by further steps illustrated in Examples 1 and 2.

EXAMPLE 7

Preparation of 1-(3-chloro-2-pyridinyl)-3-(trifluoromethyl)-1H-pyrazole-5-carboxylic acid Step A: Preparation of 3-chloro-2(1H)-pyridinone (2,2,2-trifluoro-1-methylethylidene)hydrazone 1,1,1-Trifluoroacetone (7.80 g, 69.6 mmol) was added to 3-chloro-2(1H)-pyridinone hydrazone (alternatively named (3-chloro-pyridin-2-yl)-hydrazine) (10 g, 69.7 mmol) at 20-25° C. After the addition was complete, the mixture was stirred for about 10 minutes. The solvent was removed under reduced pressure and the mixture partitioned between ethyl acetate (100 mL) and saturated aqueous sodium carbonate solution (100 mL). The organic layer was dried and evaporated. Chromatography on silica gel (eluted with ethyl acetate) gave the product as an off-white solid (11 g, 66% yield), m.p. 64-64.5° C. (after crystallization from ethyl acetate/hexanes).

IR (nujol) ν 1629, 1590, 1518, 1403, 1365, 1309, 1240, 1196, 1158, 1100, 1032, 992, 800 cm$^{-1}$.

$^1$H NMR (CDCl$_3$) δ 2.12 (s, 3H), 6.91-6.86 (m, 1H), 7.64-7.61 (m, 1H), 8.33-8.32 (m, 2H).

MS m/z 237 (M$^+$).

Step B: Preparation of ethyl hydrogen ethanedioate (3-chloro-2-pyridinyl)(2,2,2-trifluoro-1-methylethylidene)hydrazide (alternatively named ethyl hydrogen ethanedioate (3-chloro-2-pyridinyl)(2,2,2-trifluoro-1-methylethylidene)hydrazine)

Triethylamine (20.81 g, 0.206 mol) was added to 3-chloro-2(1H)-pyridinone (2,2,2-trifluoro-1-methylethylidene)hydrazone (i.e. the product of Step A) (32.63 g, 0.137 mol) in dichloromethane (68 mL) at 0° C. Ethyl chlorooxoacetate (18.75 g, 0.137 mol) in dichloromethane (69 mL) was added dropwise to the mixture at 0° C. The mixture was allowed to warm to 25° C. over about 2 hours. The mixture was cooled to 0° C. and a further portion of ethyl chlorooxoacetate (3.75 g, 27.47 mmol) in dichloromethane (14 mL) was added dropwise. After about an additional 1 hour, the mixture was diluted with dichloromethane (about 450 mL), and the mixture was washed with water (2×150 mL). The organic layer was dried and evaporated. Chromatography on silica gel (eluted with 1:1 ethyl acetate-hexanes) gave the product as a solid (42.06 g, 90% yield), m.p. 73.0-73.5° C. (after crystallization from ethyl acetate/hexanes).

IR (nujol) ν 1751, 1720, 1664, 1572, 1417, 1361, 1330, 1202, 1214, 1184, 1137, 1110, 1004, 1043, 1013, 942, 807, 836 cm$^{-1}$.

$^1$H NMR (DMSO-$d_6$, 115° C.) 1.19 (t, 3H), 1.72 (br s, 3H), 4.25 (q, 2H), 7.65 (dd, J=8.3, 4.7 Hz, 1H), 8.20 (dd, J=7.6, 1.5 Hz, 1H), 8.55 (d, J=3.6 Hz, 1H).

MS m/z 337 (M$^+$).

Step C: Preparation of ethyl 1-(3-chloro-2-pyridinyl)-4,5-dihydro-5-hydroxy-3-(trifluoromethyl)-1H-pyrazole-5-carboxylate Ethyl hydrogen ethanedioate (3-chloro-2-pyridinyl)(2,2,2-trifluoro-1-methyl-ethylidene)hydrazide (i.e. the product of Step B) (5 g, 14.8 mmol) in dimethyl sulfoxide (25 mL) was added to tetrabutylammonium fluoride hydrate (10 g) in dimethyl sulfoxide (25 mL) over 8 hours. When the addition was complete, the mixture was poured into acetic acid (3.25 g) in water (25 mL). After stirring at 25° C. overnight, the mixture was then extracted with toluene (4×25 mL), and the combined toluene extracts were washed with water (50 mL), dried and evaporated to give a solid. Chromatography on silica gel (eluted with 1:2 ethyl acetate-hexanes) gave the product as a solid (2.91 g, 50% yield, containing about 5% of 3-chloro-2(1H)-pyridinone (2,2,2-trifluoro-1-methylethylidene)hydrazone), m.p. 78-78.5° C. (after recrystallization from ethyl acetate/hexanes).

IR (nujol) ν 3403, 1726, 1618, 1582, 1407, 1320, 1293, 1260, 1217, 1187, 1150, 1122, 1100, 1067, 1013, 873, 829 $cm^{-1}$.

$^1$H NMR ($CDCl_3$) δ 1.19 (s, 3H), 3.20 (½ of ABZ pattern, J=18 Hz, 1H), 3.42 (½ of ABZ pattern, J=18 Hz, 1H), 4.24 (q, 2H), 6.94 (dd, J=7.9, 4.9 Hz, 1H), 7.74 (dd, J=7.7, 1.5 Hz, 1H), 8.03 (dd, J=4.7, 1.5 Hz, 1H).

MS m/z 319 ($M^+$).

Step D: Preparation of ethyl 1-(3-chloro-2-pyridinyl)-3-(trifluoromethyl)-1H-pyrazole-5-carboxylate Sulfuric acid (concentrated, 2 drops) was added to ethyl 1-(3-chloro-2-pyridinyl)-4,5-dihydro-5-hydroxy-3-(trifluoromethyl)-1H-pyrazole-5-carboxylate (i.e. the product of Step C) (1 g, 2.96 mmol) in acetic acid (10 mL) and the mixture was warmed to 65° C. for about 1 hour. The mixture was allowed to cool to 25° C. and most of the acetic acid was removed under reduced pressure. The mixture was partitioned between saturated aqueous sodium carbonate solution (100 mL) and ethyl acetate (100 mL). The aqueous layer was further extracted with ethyl acetate (100 mL). The combined organic extracts were dried and evaporated to give the product as an oil (0.66 g, 77% yield).

IR (neat) ν 3147, 2986, 1734, 1577, 1547, 1466, 1420, 1367, 1277, 1236, 1135, 1082, 1031, 973, 842, 802 $cm^{-1}$.

$^1$H NMR ($CDCl_3$) δ 1.23 (t, 3H), 4.25 (q, 2H), 7.21 (s, 1H), 7.48 (dd, J=8.1, 4.7 Hz, 1H), 7.94 (dd, J=6.6, 2 Hz, 1H), 8.53 (dd, J=4.7, 1.5 Hz, 1H).

MS m/z 319 ($M^+$).

Step E: Preparation of 1-(3-chloro-2-pyridinyl)-3-(trifluoromethyl)-1H-pyrazole-5-carboxylic acid Potassium hydroxide (0.5 g, 85%, 2.28 mmol) in water (1 mL) was added to ethyl 1-(3-chloro-2-pyridinyl)-3-(trifluoromethyl)-1H-pyrazole-5-carboxylate (i.e. the product of Step D) (0.66 g, 2.07 mmol) in ethanol (3 mL). After about 30 minutes, the solvent was removed under reduced pressure, and the mixture was dissolved in water (40 mL). The solution was washed with ethyl acetate (20 mL). The aqueous layer was acidified with concentrated hydrochloric acid and was extracted with ethyl acetate (3×20 mL). The combined extracts were dried and evaporated to give the product as a solid (0.53 g, 93% yield), m.p. 178-179° C. (after crystallization from hexanes-ethyl acetate).

IR (nujol) ν 1711, 1586, 1565, 1550, 1440, 1425, 1292, 1247, 1219, 1170, 1135, 1087, 1059, 1031, 972, 843, 816 $cm^{-1}$.

$^1$H NMR (DMSO-$d_6$) δ 7.61 (s, 1H), 7.77 (m, 1H), 8.30 (d, 1H), 8.60 (s, 1H).

The following Example 8 illustrates an alternative preparation of 3-chloro-1-(3-chloro-2-pyridinyl)-1H-pyrazole-5-carboxylic acid, which can be used to prepare, for example, 3-chloro-N-[4-chloro-2-methyl-6-[[(1-methylethyl)amino]carbonyl]phenyl]-1-(3-chloro-2-pyridinyl)-1H-pyrazole-5-carboxamide and 3-chloro-N-[4-chloro-2-methyl-6-[(methyl-amino)carbonyl]phenyl]-1-(3-chloro-2-pyridinyl)-1H-pyrazole-5-carboxamide, by further steps illustrated in Examples 3 and 4.

EXAMPLE 8

Preparation of 3-chloro-1-(3-chloro-2-pyridinyl)-1H-pyrazole-5-carboxylic acid

Step A: Preparation of ethyl 2-(3-chloro-2-pyridinyl)-5-oxo-3-pyrazolidinecarboxylate (alternatively named ethyl 1-(3-chloro-2-pyridinyl)-3-pyrazolidinone-5-carboxylate)

A 2-L four-necked flask equipped with a mechanical stirrer, thermometer, addition funnel, reflux condenser, and nitrogen inlet was charged with absolute ethanol (250 mL) and an ethanolic solution of sodium ethoxide (21%, 190 mL, 0.504 mol). The mixture was heated to reflux at about 83° C. It was then treated with 3-chloro-2(1H)-pyridinone hydrazone (68.0 g, 0.474 mol). The mixture was re-heated to reflux over a period of 5 minutes. The yellow slurry was then treated dropwise with diethyl maleate (88.0 mL, 0.544 mol) over a period of 5 minutes. The reflux rate increased markedly during the addition. By the end of the addition all of the starting material had dissolved. The resulting orange-red solution was held at reflux for 10 minutes. After being cooled to 65° C., the reaction mixture was treated with glacial acetic acid (50.0 mL, 0.873 mol). A precipitate formed. The mixture was diluted with water (650 mL), causing the precipitate to dissolve. The orange solution was cooled in an ice bath. Product began to precipitate at 28° C. The slurry was held at about 2° C. for 2 hours. The product was isolated via filtration, washed with aqueous ethanol (40%, 3×50 mL), and then air-dried on the filter for about 1 hour. The title product compound was obtained as a highly crystalline, light orange powder (70.3 g, 55% yield). No significant impurities were observed by $^1$H NMR.

$^1$H NMR (DMSO-$d_6$) δ 1.22 (t, 3H), 2.35 (d, 1H), 2.91 (dd, 1H), 4.20 (q, 2H), 4.84 (d, 1H), 7.20 (dd, 1H), 7.92 (d, 1H), 8.27 (d, 1H), 10.18 (s, 1H).

Step B: Preparation of ethyl 3-chloro-1-(3-chloro-2-pyridinyl)-4,5-dihydro-1H-pyrazole-5-carboxylate (alternatively named ethyl 1-(3-chloro-2-pyridinyl)-3-chloro-2-pyrazoline-5-carboxylate)

To a 2-L four-necked flask equipped with a mechanical stirrer, thermometer, reflux condenser, and nitrogen inlet was charged acetonitrile (1000 mL), ethyl 2-(3-chloro-2-pyridinyl)-5-oxo-3-pyrazolidinecarboxylate (i.e. the product of Step A) (91.0 g, 0.337 mol) and phosphorus oxychloride (35.0 mL, 0.375 mol). Upon adding the phosphorus oxychloride, the mixture self-heated from 22 to 25° C. and a precipitate formed. The light-yellow slurry was heated to reflux at 83° C. over a period of 35 minutes, whereupon the precipitate dissolved. The resulting orange solution was held at reflux for 45 minutes, whereupon it had become black-green. The reflux condenser was replaced with a distillation head, and 650 mL of solvent was removed by distillation. A second 2-L four-necked flask equipped with a mechanical stirrer was charged with sodium bicarbonate (130 g, 1.55 mol) and water (400 mL). The concentrated reaction mixture was added to the sodium bicarbonate slurry over a period of 15 minutes. The resulting, two-phase mixture was stirred vigorously for 20 minutes, at which time gas evolution had ceased. The mixture was diluted with dichloromethane (250 mL) and then was stirred for 50 minutes. The mixture was treated with Celite® 545 diatomaceous earth filter aid (11 g) and then filtered to remove a black, tarry substance that inhibited phase separation. Since the filtrate was slow to separate into distinct phases, it was diluted with dichloromethane (200 mL) and water (200 mL) and treated with more Celite® 545 (15 g). The mixture was filtered, and the filtrate was transferred to a separatory funnel. The heavier, deep green organic layer was separated. A rag layer (50 mL) was refiltered and then added to the organic layer. The organic solution (800 mL) was treated with magnesium sulfate (30 g) and silica gel (12 g), and the slurry was stirred magnetically for 30 minutes. The slurry was filtered to remove the magnesium sulfate and silica gel, which had become deep blue-green. The filter cake was washed with dichloromethane (100 mL). The filtrate was concentrated on a rotary evaporator. The product consisted of dark amber oil (92.0 g, 93% yield). The only appreciable impurities observed by $^1$H NMR were 1% starting material and 0.7% acetonitrile.

$^1$H NMR (DMSO-$d_6$) δ 1.15 (t, 3H), 3.26 (dd, 1H), 3.58 (dd, 1H), 4.11 (q, 2H), 5.25 (dd, 1H), 7.00 (dd, 1H), 7.84 (d, 1H), 8.12 (d, 1H).

Step C: Preparation of ethyl 3-chloro-1-(3-chloro-2-pyridinyl)-1H-pyrazole-5-carboxylate (alternatively named ethyl 1-(3-chloro-2-pyridinyl)-3-chloropyrazole-5-carboxylate)

A 2-L four-necked flask equipped with a mechanical stirrer, thermometer, reflux condenser, and nitrogen inlet was charged with ethyl 3-chloro-1-(3-chloro-2-pyridinyl)-4,5-dihydro-1H-pyrazole-5-carboxylate (i.e. the product of Step B) (95% pure, 99.5 g, 0.328 mol), acetonitrile (1000 mL) and sulfuric acid (98%, 35.0 mL, 0.661 mol). The mixture self-heated from 22 to 35° C. upon adding the sulfuric acid. After being stirred for several minutes, the mixture was treated with potassium persulfate (140 g, 0.518 mol). The slurry was heated to reflux at 84° C. for 4.5 hours. The resulting orange slurry while still warm (50-65° C.) was filtered to remove a fine, white precipitate. The filter cake was washed with acetonitrile (50 mL). The filtrate was concentrated to about 500 mL on a rotary evaporator. A second 2-L four-necked flask equipped with a mechanical stirrer was charged with water (1250 mL). The concentrated reaction mass was added to the water over a period of about 5 minutes. The product was isolated via filtration, washed with aqueous acetonitrile (25%, 3×125 mL), washed once with water (100 mL), and then dried overnight in vacuo at room temperature. The product consisted of a crystalline, orange powder (79.3 g, 82% yield). The only appreciable impurities observed by $^1$H NMR were about 1.9% water and 0.6% acetonitrile.

$^1$H NMR (DMSO-$d_6$) δ 1.09 (t, 3H), 4.16 (q, 2H), 7.31 (s, 1H), 7.71 (dd, 1H), 8.38 (d, 1H), 8.59 (d, 1H).

Step D: Preparation of 3-chloro-1-(3-chloro-2-pyridinyl)-1H-pyrazole-5-carboxylic acid (alternatively named 1-(3-chloro-2-pyridinyl)-3-chloropyrazole-5-carboxylic acid)

A 1-L four-necked flask equipped with a mechanical stirrer, thermometer, and nitrogen inlet was charged with ethyl 3-chloro-1-(3-chloro-2-pyridinyl)-1H-pyrazole-5-carboxylate (i.e. the product of Step C) (97.5% pure, 79.3 g, 0.270 mol), methanol (260 mL), water (140 mL) and sodium hydroxide pellets (13.0 g, 0.325 mol). Upon adding the sodium hydroxide the mixture self-heated from 22 to 35° C., and the starting material began to dissolve. After being stirred for 45 minutes under ambient conditions, all of the starting material had dissolved. The resulting deep orange-brown solution was concentrated to about 250 mL on a rotary evaporator. The concentrated reaction mixture was then diluted with water (400 mL). The aqueous solution was extracted with ether (200 mL). Then the aqueous layer was transferred to a 1-L Erlenmeyer flask equipped with a magnetic stirrer. The solution was treated dropwise with concentrated hydrochloric acid (36.0 g, 0.355 mol) over a period of about 10 minutes. The product was isolated via filtration, reslurried with water (2×200 mL), cover washed once with water (100 mL) and then air-dried on the filter for 1.5 hours. The product consisted of a crystalline, light brown powder (58.1 g, 83% yield). About 0.7% ether was the only appreciable impurity observed by $^1$H NMR.

$^1$H NMR (DMSO-$d_6$) δ 7.20 (s, 1H), 7.68 (dd, 1H), 8.25 (d, 1H), 8.56 (d, 1H), 13.95 (br s, 1H).

The following Example 9 illustrates an alternative preparation of 3-bromo-1-(3-chloro-2-pyridinyl)-1H-pyrazole-5-carboxylic acid, which can be used to prepare, for example, 3-bromo-N-[4-chloro-2-methyl-6-[[(1-methylethyl)amino]carbonyl]phenyl]-1-(3-chloro-2-pyridinyl)-1H-pyrazole-5-carboxamide and 3-bromo-N-[4-chloro-2-methyl-6-[(methyl-amino)carbonyl]phenyl]-1-(3-chloro-2-pyridinyl)-1H-pyrazole-5-carboxamide, by further steps illustrated in Examples 5 and 6.

EXAMPLE 9

Preparation of 3-bromo-1-(3-chloro-2-pyridinyl)-1H-pyrazole-5-carboxylic acid

Step A1: Preparation of ethyl 3-bromo-1-(3-chloro-2-pyridinyl)-4,5-dihydro-1H-pyrazole-5-carboxylate (alternatively named ethyl 1-(3-chloro-2-pyridinyl)-3-bromo-2-pyrazoline-5-carboxylate) using phosphorus oxybromide A 1-L four-necked flask equipped with a mechanical stirrer, thermometer, reflux condenser, and nitrogen inlet was charged with acetonitrile (400 mL), ethyl 2-(3-chloro-2-pyridinyl)-5-oxo-3-pyrazolidinecarboxylate (i.e. the product of Example 8, Step A) (50.0 g, 0.185 mol) and phosphorus oxybromide (34.0 g, 0.119 mol). The orange slurry was heated to reflux at 83° C. over a period of 20 minutes. The resulting turbid, orange solution was held at reflux for 75 minutes, at which time a dense, tan, crystalline precipitate had formed. The reflux condenser was replaced with a distillation head, and a cloudy, colorless distillate (300 mL) was collected. A second 1-L four-necked flask equipped with a mechanical stirrer was charged with sodium bicarbonate (45 g, 0.54 mol) and water (200 mL). The concentrated reaction mixture was added to the sodium bicarbonate slurry over a period of 5 minutes. The resulting two-phase mixture was stirred vigorously for 5 minutes, at which time gas evolution had ceased. The mixture was diluted with dichloromethane (200 mL) and then was stirred for 75 minutes. The mixture was treated with 5 g of Celite® 545 diatomaceous filter aid and then filtered to remove a brown, tarry substance. The filtrate was transferred to a separatory funnel. The brown organic layer (400 mL) was separated and then was treated with magnesium sulfate (15 g) and Darco® G60 activated charcoal (2.0 g). The resulting slurry was stirred magnetically for 15 minutes and then filtered to remove the magnesium sulfate and charcoal. The green filtrate was treated with silica gel (3 g) and stirred for several minutes. The deep blue-green silica gel was removed by filtration, and the filtrate was concentrated on a rotary evaporator. The product consisted of a light amber oil (58.6 g, 95% yield), which crystallized upon standing. The only appreciable impurity observed by $^1$H NMR was 0.3% acetonitrile.

$^1$H NMR (DMSO-$d_6$) δ 1.15 (t, 3H), 3.29 (dd, 1H), 3.60 (dd, 1H), 4.11 (q, 2H), 5.20 (dd, 1H), 6.99 (dd, 1H), 7.84 (d, 1H), 8.12 (d, 1H).

Step A2: Preparation of ethyl 3-bromo-1-(3-chloro-2-pyridinyl)-4,5-dihydro-1H-pyrazole-5-carboxylate using phosphorus pentabromide A 1-L four-necked flask equipped with a mechanical stirrer, thermometer, reflux condenser, and nitrogen inlet was charged with acetonitrile (330 mL), ethyl 2-(3-chloro-2-pyridinyl)-5-oxo-3-pyrazolidinecarboxylate (i.e. the product of Example 8, Step A) (52.0 g, 0.193 mol), and phosphorus pentabromide (41.0 g, 0.0952 mol). The orange slurry was heated to reflux at 84° C. over a period of 20 minutes. The resulting brick-red mixture was held at reflux for 90 minutes, at which time a dense tan crystalline precipitate had formed. The reflux condenser was replaced with a distillation head, and a cloudy, colorless distillate (220 mL) was collected. A second 1-L four-necked flask equipped with a mechanical stirrer was charged with sodium bicarbonate (40 g, 0.48 mol) and water (200 mL). The concentrated reaction mixture was added to the sodium bicarbonate slurry over a period of 5 minutes. The resulting, two-phase mixture was stirred vigorously for 10 minutes, at which time gas evolution had ceased. The mixture was diluted with dichloromethane (200 mL) and then was stirred for 10 minutes. The mixture was treated with Celite® 545 diatomaceous filter aid (5 g) and then filtered to remove a purple, tarry substance. The filter cake was washed with dichloromethane (50 mL). The filtrate was transferred to a separatory funnel. The purple-red organic layer (400 mL) was separated and then was treated with magnesium sulfate (15 g) and Darco® G60 activated charcoal (2.2 g). The slurry was stirred magnetically for 40 minutes. The slurry was filtered to remove the magnesium sulfate and charcoal. The filtrate was concentrated on a rotary evaporator. The product consisted of a dark amber oil (61.2 g, 95% yield), which crystallized upon standing. The only appreciable impurity observed by $^1$H NMR was 0.7% acetonitrile.

$^1$H NMR (DMSO-$d_6$) δ 1.15 (t, 3H), 3.29 (dd, 1H), 3.60 (dd, 1H), 4.11 (q, 2H), 5.20 (dd, 1H), 6.99 (dd, 1H), 7.84 (d, 1H), 8.12 (d, 1H).

Step B: Preparation of ethyl 3-bromo-1-(3-chloro-2-pyridinyl)-1H-pyrazole-5-carboxylate (alternatively named ethyl 1-(3-chloro-2-pyridinyl)-3-bromopyrazole-5-carboxylate)

A 1-L four-necked flask equipped with a mechanical stirrer, thermometer, reflux condenser, and nitrogen inlet was charged with ethyl 3-bromo-1-(3-chloro-2-pyridinyl)-4,5-dihydro-1H-pyrazole-5-carboxylate (i.e. the product of Steps A1 and A2) (40.2 g, 0.121 mol), acetonitrile (300 mL) and sulfuric acid (98%, 13.0 mL, 0.245 mol). The mixture self-heated from 22 to 36° C. upon adding the sulfuric acid. After being stirred for several minutes, the mixture was treated with potassium persulfate (48.0 g, 0.178 mol). The slurry was heated to reflux at 84° C. for 2 hours. The resulting orange slurry while still warm (50-65° C.) was filtered to remove a white precipitate. The filter cake was washed with acetonitrile (2×50 mL). The filtrate was concentrated to about 200 mL on a rotary evaporator. A second 1-L four-necked flask equipped with a mechanical stirrer was charged with water (400 mL). The concentrated reaction mass was added to the water over a period of about 5 minutes. The product was isolated via filtration, washed sequentially with aqueous acetonitrile (20%, 100 mL) and water (75 mL), and was then air-dried on the filter for 1 hour. The product consisted of a crystalline, orange powder (36.6 g, 90% yield). The only appreciable impurities observed by $^1$H NMR were about 1% of an unknown and 0.5% acetonitrile.

$^1$H NMR (DMSO-$d_6$) δ 1.09 (t, 3H), 4.16 (q, 2H), 7.35 (s, 1H), 7.72 (dd, 1H), 8.39 (d, 1H), 8.59 (d, 1H).

Step C: Preparation of 3-bromo-1-(3-chloro-2-pyridinyl)-1H-pyrazole-5-carboxylic acid (alternatively named 1-(3-chloro-2-pyridinyl)-3-bromopyrazole-5-carboxylic acid)

A 300-mL four-necked flask equipped with a mechanical stirrer, thermometer, and nitrogen inlet was charged with ethyl 3-bromo-1-(3-chloro-2-pyridinyl)-1H-pyrazole-5-carboxylate (i.e. the product of Step B) (98.5% pure, 25.0 g, 0.0756 mol), methanol (75 mL), water (50 mL), and sodium hydroxide pellets (3.30 g, 0.0825 mol). Upon adding the sodium hydroxide the mixture self-heated from 29 to 34° C. and the starting material began to dissolve. After being stirred for 90 minutes under ambient conditions, all of the starting material had dissolved. The resulting dark orange solution was concentrated to about 90 mL on a rotary evaporator. The concentrated reaction mixture was then diluted with water (160 mL). The aqueous solution was extracted with ether (100 mL). Then the aqueous layer was transferred to a 500-mL Erlenmeyer flask equipped with a magnetic stirrer. The solution was treated dropwise with concentrated hydrochloric acid (8.50 g, 0.0839 mol) over a period of about 10 minutes. The product was isolated via filtration, reslurried with water (2×40 mL), cover washed once with water (25 mL), and then air-dried on the filter for 2 hours. The product consisted of a crystalline, tan powder (20.9 g, 91% yield). The only appreciable impurities observed by $^1$H NMR were about 0.8% of an unknown and 0.7% ether.

$^1$H NMR (DMSO-$d_6$) δ 7.25 (s, 1H), 13.95 (br s, 1H), 8.56 (d, 1H), 8.25 (d, 1H), 7.68 (dd, 1H).

The following Example 10 illustrates an alternative preparation of ethyl 3-bromo-1-(3-chloro-2-pyridinyl)-4,5-dihydro-1H-pyrazole-5-carboxylate, which can be used to prepare, for example, ethyl 3-bromo-1-(3-chloro-2-pyridinyl)-1H-pyrazole-5-carboxylate (i.e. product of Example 9, Step B).

EXAMPLE 10

Preparation of ethyl 3-bromo-1-(3-chloro-2-pyridinyl)-4,5-dihydro-1H-pyrazole-5-carboxylate from ethyl 3-chloro-1-(3-chloro-2-pyridinyl)-4,5-dihydro-1H-pyrazole-5-carboxylate using hydrogen bromide Hydrogen bromide was passed through a solution of ethyl 3-chloro-1-(3-chloro-2-pyridinyl)-4,5-dihydro-1H-pyrazole-5-carboxylate (i.e. product of Example 8, Step B) (8.45 g, 29.3 mmol) in dibromomethane (85 mL). After 90 minutes the gas flow was terminated, and the reaction mixture was washed with aqueous sodium bicarbonate solution (100 mL). The organic phase was dried and evaporated under reduced pressure to give the title product as an oil (9.7 g, 99% yield), which crystallized on standing.

$^1$H NMR (CDCl$_3$) δ 1.19 (t, 3H), 3.24 (½ of AB in ABX pattern, J=9.3, 17.3 Hz, 1H), 3.44 (½ of AB in ABX pattern, J=11.7, 17.3 Hz, 1H), 4.18 (q, 2H), 5.25 (X of ABX, 1H, J=9.3, 11.9 Hz), 6.85 (dd, J=4.7, 7.7 Hz, 1H), 7.65 (dd, J=1.6, 7.8 Hz, 1H), 8.07 (dd, J=1.6, 4.8 Hz, 1H).

The following Example 11 illustrates the preparation of ethyl 1-(3-chloro-2-pyridinyl)-4,5-dihydro-3-[[(4-methylphenyl)sulfonyl]oxy]-1H-pyrazole-5-carboxylate, which can be used to prepare ethyl 3-bromo-1-(3-chloro-2-pyridinyl)-4,5-dihydro-1H-pyrazole-5-carboxylate by procedures similar to that described in Example 10.

EXAMPLE 11

Preparation of ethyl 1-(3-chloro-2-pyridinyl)-4,5-dihydro-3-[[(4-methylphenyl)sulfonyl]oxy]-1H-pyrazole-5-carboxylate Triethylamine (3.75 g, 37.1 mmol) was added dropwise to a mixture of ethyl 2-(3-chloro-2-pyridinyl)-5-oxo-3-pyrazolidinecarboxylate (i.e. the product of Example 8, Step A) (10.0 g, 37.1 mmol) and p-toluenesulfonyl chloride (7.07 g, 37.1 mmol) in dichloromethane (100 mL) at 0° C. Further portions of p-toluenesulfonyl chloride (0.35 g, 1.83 mmol) and triethylamine (0.19 g, 1.88 mmol) were added. The reaction mixture was then allowed to warm to room temperature and was stirred overnight. The mixture was then diluted with dichloromethane (200 mL) and washed with water (3×70 mL). The organic phase was dried and evaporated to leave the title product as an oil (13.7 g, 87% yield), which slowly formed crystals. Product recrystallized from ethyl acetate/hexanes melted at 99.5-100° C.

IR (nujol): 1740, 1638, 1576, 1446, 1343, 1296, 1228, 1191, 1178, 1084, 1027, 948, 969, 868, 845 cm$^{-1}$.

$^1$H NMR (CDCl$_3$) δ 1.19 (t, 3H), 2.45 (s, 3H), 3.12 (½ of AB in ABX pattern, J=17.3, 9 Hz, 1H), 3.33 (½ of AB in ABX pattern, J=17.5, 11.8 Hz, 1H), 4.16 (q, 2H), 5.72 (X of ABX, J=9, 11.8 Hz, 1H), 6.79 (dd, J=4.6, 7.7 Hz, 1H), 7.36 (d, J=8.4 Hz, 2H), 7.56 (dd, J=1.6, 7.8 Hz, 1H), 7.95 (d, J=8.4 Hz, 2H), 8.01 (dd, J=1.4, 4.6 Hz, 1H).

EXAMPLE 12

Preparation of N-[4-chloro-2-methyl-6-[(methylamino)carbonyl]phenyl]-1-(3-chloro-2-pyridinyl)-3-(2,2,2-trifluoroethoxy)-1H-pyrazole-5-carboxamide Step A: Preparation of ethyl 1-(3-chloro-2-pyridinyl)-2,3-dihydro-3-oxo-1H-pyrazole-5-carboxylate To a suspension of ethyl 2-(3-chloro-2-pyridinyl)-5-oxo-3-pyrazolidinecarboxylate (i.e. product of Example 8, Step A) (27 g, 100 mmol) stirred in dry acetonitrile (200 mL) was added sulfuric acid (20 g, 200 mmol) in one portion. The reaction mixture thinned to form a pale green, nearly clear solution before thickening again to form a pale yellow suspension. Potassium persulfate (33 g, 120 mmol) was added in one portion, and then the reaction mixture was heated at gentle reflux for 3.5 hours. After cooling using an ice bath, a precipitate of white solid was removed by filtration and discarded. The filtrate was diluted with water (400 mL) and then extracted three times with ethyl ether (700 mL total). Concentration of the combined ether extracts to a reduced volume (75 mL) caused precipitation of an off-white solid (3.75 g), which was collected by filtration. The ether mother liquor was further concentrated to yield a second crop of an off-white precipitate (4.2 g), which was also collected by filtration. An off-white solid also precipitated from the aqueous phase; this solid (4.5 g) was collected by filtration to provide a combined total of 12.45 g of the title compound.

$^1$H NMR (DMSO-d$_6$) δ 1.06 (t, 3H), 4.11 (q, 2H), 6.34 (s, 1H), 7.6 (t, 1H), 8.19 (d, 1H), 8.5 (d, 1H), 10.6 (s, 1H).

Step B: Preparation of ethyl 1-(3-chloro-2-pyridinyl)-3-(2,2,2-trifluoroethoxy)-1H-pyrazole-5-carboxylate To a suspension of ethyl 1-(3-chloro-2-pyridinyl)-2,3-dihydro-3-oxo-1H-pyrazole-5-carboxylate (i.e. product of Step A) (0.8 g, 3 mmol) stirred in dry acetonitrile (15 mL) at −5° C. was added potassium carbonate (0.85 g, 6.15 mmol). The suspension was stirred for 15 minutes at 20° C. The stirred suspension was then cooled to 5° C., and 2,2,2-trifluoro-ethyl trifluoromethanesulfonate (0.8 g, 3.45 mmol) was added dropwise. The reaction mixture was warmed to room temperature and then heated to reflux, at which time thin layer chromatography showed the reaction to be complete. Water (25 mL) was added to the reaction mixture, which was then extracted with ethyl ether. The ether extract was dried over magnesium sulfate and concentrated to yield the title product compound (1.05 g) as a pale yellow oil.

$^1$H NMR (CDCl$_3$) δ 1.21 (t, 3H), 4.20 (q, 2H), 4.63 (q, 2H), 6.53 (s, 1H), 7.4 (t, 1H), 7.9 (d, 1H), 8.5 (d, 1H).

Step C: Preparation of 1-(3-chloro-2-pyridinyl)-3-(2,2,2-trifluoroethoxy)-1H-pyrazole-5-carboxylic acid To a stirred solution of ethyl 1-(3-chloro-2-pyridinyl)-3-(2,2,2-trifluoroethoxy)-1H-pyrazole-5-carboxylate (i.e. product of Step B) (0.92 g, 2.8 mmol) in methanol (15 mL) was added water (5 mL), which caused the reaction mixture to become cloudy. An aqueous solution of sodium hydroxide (50%, 1.5 g, 19.2 mmol) was added dropwise, and the reaction mixture was stirred at room temperature for 30 minutes, during which time the reaction mixture became again clear. Water (20 mL) was added and the reaction mixture was extracted with ethyl ether, which was discarded. The aqueous phase was acidified to pH 2 using concentrated hydrochloric acid and then extracted with ethyl acetate (50 mL). The ethyl acetate extract, which was washed with water (20 mL) and brine (20 mL), dried over magnesium sulfate and concentrated to give the title compound, isolated as a white solid (0.8 g).

$^1$H NMR (DMSO-d$_6$) δ 4.9 (q, 2H), 6.75 (s, 1H), 7.6 (t, 1H), 8.2 (d, 1H), 8.55 (d, 1H), 13.7 (bs, 1H).

Step D: Preparation of 6-chloro-8-methyl-2H-3,1-benzoxazine-2,4(1H)-dione

To a suspension of 2-amino-3-methyl-5-chlorobenzoic acid (i.e. product of Example 1, Step A) (97 g, 520 mmol) stirred in dry dioxane (750 mL) at room temperature, trichloromethyl chloroformate (63 g, 320 mmol) was added dropwise. The reaction mixture exothermically warmed slowly to 42° C., and the solid almost completely dissolved before a thick suspension formed again. After the suspension was stirred at ambient temperature for 2.5 hours, the title compound was isolated by filtration, washed with ethyl ether, and dried to yield the title product compound, obtained as a white solid (98 g).

$^1$H NMR (DMSO-d$_6$) δ 2.3 (s, 3H), 7.70 (s, 1H), 7.75 (s, 1H), 11.2 (s, 1H).

Step E: Preparation of 6-chloro-2-[1-(3-chloro-2-pyridinyl)-3-(2,2,2-trifluoroethoxy)-1H-pyrazol-5-yl]-8-methyl-4H-3,1-benzoxazin-4-one To a suspension of 1-(3-chloro-2-pyridinyl)-3-(2,2,2-trifluoroethoxy)-1H-pyrazole-5-carboxylic acid (i.e. product of Step C) (7.9 g, 24 mmol) stirred in dichloromethane (100 mL) was added N,N-dimethylformamide (4 drops). Oxalyl chloride (4.45 g, 35 mmol) was added dropwise over a period of 45 minutes. The resulting solution was stirred at room temperature for 4 hours and then concentrated under vacuum. The isolated acid chloride was dissolved in dry acetonitrile (10 mL) and added to a suspension of 6-chloro-8-methyl-2H-3,1-benzoxazine-2,4(1H)-dione (i.e. product of Step D) (4.9 g, 23 mmol) stirred in dry acetonitrile (14 mL). Pyridine (10 mL) was added, and the solution heated at reflux 6 hours. After cooling using an ice bath, a precipitate of white solid (9.15 g) was collected. The $^1$H NMR spectrum of the collected precipitate showed peaks consistent with the title compound and residual 6-chloro-8-methyl-2H-3,1-benzoxazine-2,4(1H)-dione starting material. A small portion of the collected precipitate was recrystallized from acetonitrile to yield the pure title product melting at 178-180° C.

$^1$H NMR (DMSO-d$_6$) δ 1.72 (s, 3H), 4.96 (q, 2H), 7.04 (s, 1H), 7.7 (t, 1H), 7.75 (s, 1H), 7.9 (s, 1H), 8.3 (d, 1H), 8.6 (d, 1H).

Step F: Preparation of N-[4-chloro-2-methyl-6-[(methylamino)carbonyl]phenyl]-1-(3-chloro-2-pyridinyl)-3-(2,2,2-trifluoroethoxy)-1H-pyrazole-5-carboxamide To a suspension of the 6-chloro-2-[1-(3-chloro-2-pyridinyl)-3-(2,2,2-trifluoroethoxy)-1H-pyrazol-5-yl]-8-methyl-4H-3,1-benzoxazin-4-one (i.e. precipitate product of Step E) (3.53 g, 7.5 mmol) in tetrahydrofuran (15 mL), methylamine (2.0 M solution in THF, 11 mL, 22 mmol) was added dropwise, and the resulting solution was stirred at room temperature for 45 minutes. Thin layer chromatography then showed the reaction to be complete. Ethyl ether (100 mL) was added, and the reaction mixture was stirred for 2 hours while a precipitate formed. The precipitate was collected by filtration and then recrystallized from acetonitrile to yield a white solid (0.82 g). A second crop of white solid (0.35 g) precipitated from the acetonitrile mother liquor and was collected by filtration. The initial ether/tetrahydrofuran mother liquor was concentrated to dryness, and the residual solid was recrystallized from acetonitrile to yield a third crop of white solid (0.95 g). The three crops were combined, totaling 2.12 g (after drying) of the title compound, isolated as a white solid, melting at 207-208° C.

$^1$H NMR (CDCl$_3$) δ 2.18 (s, 3H), 2.92 (d, 3H), 4.66 (q, 2H), 6.15 (q, 1H), 6.6 (s, 1H), 7.2 (s, 1H), 7.25 (s, 1H), 7.35 (t, 1H), 7.8 (d, 1H), 8.45 (d, 1H), 10.0 (s, 1H).

Examples 13 and 14 illustrate alternatives to reaction conditions described in Example 5, Step E and Example 3, Step E, respectively.

EXAMPLE 13

Preparation of 2-[3-bromo-1-(3-chloro-2-pyridinyl)-1H-pyrazol-5-yl]-6-chloro-8-methyl-4H-3,1-benzoxazin-4-one Methanesulfonyl chloride (1.0 mL, 1.5 g, 13 mmol) was dissolved in acetonitrile (10 mL), and the mixture was cooled to −5° C. A solution of 3-bromo-1-(3-chloro-2-pyridinyl)-1H-pyrazole-5-carboxylic acid (i.e. the pyrazolecarboxylic acid product of Example 5, Step D) (3.02 g, 10 mmol) and pyridine (1.4 mL, 1.4 g, 17 mmol) in acetonitrile (10 mL) was added dropwise over 5 minutes at −5 to 0° C. A slurry formed during the addition. The mixture was stirred 5 minutes at this temperature, and then a mixture of 2-amino-3-methyl-5-chlorobenzoic acid (i.e. the product of Example 1 Step A) (1.86 g, 10 mmol) and pyridine (2.8 mL, 2.7 g, 35 mmol) in acetonitrile (10 mL) was added, rinsing with more acetonitrile (5 mL). The mixture was stirred 15 minutes at −5 to 0° C., and then methanesulfonyl chloride (1.0 mL, 1.5 mL, 13 mmol) in acetonitrile (5 mL) was added dropwise over 5 minutes at a temperature of −5 to 0° C. The reaction mixture was stirred 15 minutes more at this temperature, then allowed to warm slowly to room temperature, and stirred 4 h. Water (20 mL) was added dropwise, and the mixture was stirred 15 minutes. Then the mixture was filtered, and the solids were washed with 2:1 acetonitrile-water (3×3 mL), then with acetonitrile (2×3 mL), and dried under nitrogen to afford the title product as a light yellow powder, 4.07 g (90.2% crude yield), melting at 203-205° C. HPLC of the product using a Zorbax® RX-C8 chromatography column (4.6 mm x 25 cm, eluent 25-95% acetonitrile/pH 3 water) showed a major peak corresponding to the title compound and having 95.7% of total chromatogram peak area.

$^1$H NMR (DMSO-d$_6$) δ 1.72 (s, 3H) 7.52 (s, 1H), 7.72-7.78 (m, 2H), 7.88 (m, 1H), 8.37 (dd, 1H), 8.62 (dd, 1H).

EXAMPLE 14

Preparation of 6-chloro-2-[3-chloro-1-(3-chloro-2-pyridinyl)-1H-pyrazol-5-yl]-8-methyl-4H-3,1-benzoxazin-4-one Methanesulfonyl chloride (1.0 mL, 1.5 g, 13 mmol) was dissolved in acetonitrile (10 mL), and the mixture was cooled to −5° C. A solution of 3-chloro-1-(3-chloro-2-pyridinyl)-1H-pyrazole-5-carboxylic acid (i.e. the carboxylic acid product of Example 3, Step D) (2.58 g, 10 mmol) and pyridine (1.4 mL, 1.4 g, 17 mmol) in acetonitrile (10 mL) was added dropwise over 5 minutes at −5 to 0° C. A slurry formed during the addition. The mixture was stirred 5 minutes at this temperature, and then 2-amino-3-methyl-5-chlorobenzoic acid (i.e. the product from Example 1, Step A) (1.86 g, 10 mmol) was added all at once. Then a solution of pyridine (2.8 mL, 2.7 g, 35 mmol) in acetonitrile (10 mL) was added dropwise in 5 min at −5 to 0° C. The mixture was stirred 15 minutes at −5 to 0° C., and then methanesulfonyl chloride (1.0 mL, 1.5 mL, 13 mmol) in acetonitrile (5 mL) was added dropwise in 5 min at −5 to 0° C. The reaction mixture was stirred 15 minutes at this temperature, then allowed to warm slowly to room temperature, and stirred 4 h. Water (15 mL) was added dropwise, and the mixture was stirred 15 minutes. Then the mixture was filtered, and the solids were washed with 2:1 acetonitrile-water (3×3 mL), then with acetonitrile (2×3 mL), and dried under nitrogen to afford the title product as a pale yellow powder, 3.83 g (94.0% crude yield), melting at 199-201° C. HPLC of the product using a Zorbax® RX-C8 chromatography column (4.6 mm×25 cm, eluent 25-95% acetonitrile/pH 3 water) showed a major peak corresponding to the title compound and having 97.8% of total chromatogram peak area.

$^1$H NMR (DMSO-d$_6$) δ 1.72 (s, 3H), 7.48 (s, 1H), 7.74-7.80 (m, 2H), 7.87 (m, 1H), 8.37 (dd, 1H), 8.62 (dd, 1H).

By the procedures described herein together with methods known in the art, the following compounds of Table 1 can be prepared. The following abbreviations are used in the Tables which follow: t means tertiary, s means secondary, n means normal, i means iso, Me means methyl, Et means ethyl, Pr means propyl, i-Pr means isopropyl, and Bu means butyl.

TABLE 1

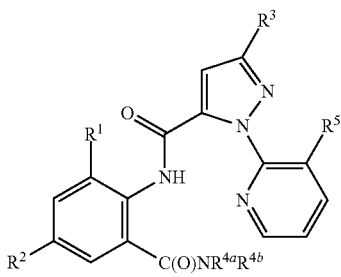

| R¹ | R² | R³ | R⁴ᵃ | R⁴ᵇ | R⁵ | R¹ | R² | R³ | R⁴ᵃ | R⁴ᵇ | R⁵ |
|---|---|---|---|---|---|---|---|---|---|---|---|
| CH₃ | F | CF₃ | Me | H | Cl | Cl | F | CF₃ | Me | H | Cl |
| CH₃ | F | CF₃ | Et | H | Cl | Cl | F | CF₃ | Et | H | Cl |
| CH₃ | F | CF₃ | i-Pr | H | Cl | Cl | F | CF₃ | i-Pr | H | Cl |
| CH₃ | F | CF₃ | t-Bu | H | Cl | Cl | F | CF₃ | t-Bu | H | Cl |
| CH₃ | F | CF₃ | Me | Me | Cl | Cl | F | CF₃ | Me | Me | Cl |
| CH₃ | F | CF₃ | Me | H | Br | Cl | F | CF₃ | Me | H | Br |
| CH₃ | F | CF₃ | Et | H | Br | Cl | F | CF₃ | Et | H | Br |
| CH₃ | F | CF₃ | i-Pr | H | Br | Cl | F | CF₃ | i-Pr | H | Br |
| CH₃ | F | CF₃ | t-Bu | H | Br | Cl | F | CF₃ | t-Bu | H | Br |
| CH₃ | F | CF₃ | Me | Me | Br | Cl | F | CF₃ | Me | Me | Br |
| CH₃ | F | Cl | Me | H | Cl | Cl | F | Cl | Me | H | Cl |
| CH₃ | F | Cl | Et | H | Cl | Cl | F | Cl | Et | H | Cl |
| CH₃ | F | Cl | i-Pr | H | Cl | Cl | F | Cl | i-Pr | H | Cl |
| CH₃ | F | Cl | t-Bu | H | Cl | Cl | F | Cl | t-Bu | H | Cl |
| CH₃ | F | Cl | Me | Me | Cl | Cl | F | Cl | Me | Me | Cl |
| CH₃ | F | Cl | Me | H | Br | Cl | F | Cl | Me | H | Br |
| CH₃ | F | Cl | Et | H | Br | Cl | F | Cl | Et | H | Br |
| CH₃ | F | Cl | i-Pr | H | Br | Cl | F | Cl | i-Pr | H | Br |
| CH₃ | F | Cl | t-Bu | H | Br | Cl | F | Cl | t-Bu | H | Br |
| CH₃ | F | Cl | Me | Me | Br | Cl | F | Cl | Me | Me | Br |
| CH₃ | F | Br | Me | H | Cl | Cl | F | Br | Me | H | Cl |
| CH₃ | F | Br | Et | H | Cl | Cl | F | Br | Et | H | Cl |
| CH₃ | F | Br | i-Pr | H | Cl | Cl | F | Br | i-Pr | H | Cl |
| CH₃ | F | Br | t-Bu | H | Cl | Cl | F | Br | t-Bu | H | Cl |
| CH₃ | F | Br | Me | Me | Cl | Cl | F | Br | Me | Me | Cl |
| CH₃ | F | Br | Me | H | Br | Cl | F | Br | Me | H | Br |
| CH₃ | F | Br | Et | H | Br | Cl | F | Br | Et | H | Br |
| CH₃ | F | Br | i-Pr | H | Br | Cl | F | Br | i-Pr | H | Br |
| CH₃ | F | Br | t-Bu | H | Br | Cl | F | Br | t-Bu | H | Br |
| CH₃ | F | Br | Me | Me | Br | Cl | F | Br | Me | Me | Br |
| CH₃ | F | OCH₂CF₃ | Me | H | Cl | Cl | F | OCH₂CF₃ | Me | H | Cl |
| CH₃ | F | OCH₂CF₃ | Et | H | Cl | Cl | F | OCH₂CF₃ | Et | H | Cl |
| CH₃ | F | OCH₂CF₃ | i-Pr | H | Cl | Cl | F | OCH₂CF₃ | i-Pr | H | Cl |
| CH₃ | F | OCH₂CF₃ | t-Bu | H | Cl | Cl | F | OCH₂CF₃ | t-Bu | H | Cl |
| CH₃ | F | OCH₂CF₃ | Me | Me | Cl | Cl | F | OCH₂CF₃ | Me | Me | Cl |
| CH₃ | F | OCH₂CF₃ | Me | H | Br | Cl | F | OCH₂CF₃ | Me | H | Br |
| CH₃ | F | OCH₂CF₃ | Et | H | Br | Cl | F | OCH₂CF₃ | Et | H | Br |
| CH₃ | F | OCH₂CF₃ | i-Pr | H | Br | Cl | F | OCH₂CF₃ | i-Pr | H | Br |
| CH₃ | F | OCH₂CF₃ | t-Bu | H | Br | Cl | F | OCH₂CF₃ | t-Bu | H | Br |
| CH₃ | F | OCH₂CF₃ | Me | Me | Br | Cl | F | OCH₂CF₃ | Me | Me | Br |
| CH₃ | Cl | CF₃ | Me | H | Cl | Cl | Cl | CF₃ | Me | H | Cl |
| CH₃ | Cl | CF₃ | Et | H | Cl | Cl | Cl | CF₃ | Et | H | Cl |
| CH₃ | Cl | CF₃ | i-Pr | H | Cl | Cl | Cl | CF₃ | i-Pr | H | Cl |
| CH₃ | Cl | CF₃ | t-Bu | H | Cl | Cl | Cl | CF₃ | t-Bu | H | Cl |
| CH₃ | Cl | CF₃ | Me | Me | Cl | Cl | Cl | CF₃ | Me | Me | Cl |
| CH₃ | Cl | CF₃ | Me | H | Br | Cl | Cl | CF₃ | Me | H | Br |
| CH₃ | Cl | CF₃ | Et | H | Br | Cl | Cl | CF₃ | Et | H | Br |
| CH₃ | Cl | CF₃ | i-Pr | H | Br | Cl | Cl | CF₃ | i-Pr | H | Br |
| CH₃ | Cl | CF₃ | t-Bu | H | Br | Cl | Cl | CF₃ | t-Bu | H | Br |
| CH₃ | Cl | CF₃ | Me | Me | Br | Cl | Cl | CF₃ | Me | Me | Br |
| CH₃ | Cl | Cl | Me | H | Cl | Cl | Cl | Cl | Me | H | Cl |
| CH₃ | Cl | Cl | Et | H | Cl | Cl | Cl | Cl | Et | H | Cl |
| CH₃ | Cl | Cl | i-Pr | H | Cl | Cl | Cl | Cl | i-Pr | H | Cl |
| CH₃ | Cl | Cl | t-Bu | H | Cl | Cl | Cl | Cl | t-Bu | H | Cl |
| CH₃ | Cl | Cl | Me | Me | Cl | Cl | Cl | Cl | Me | Me | Cl |
| CH₃ | Cl | Cl | Me | H | Br | Cl | Cl | Cl | Me | H | Br |
| CH₃ | Cl | Cl | Et | H | Br | Cl | Cl | Cl | Et | H | Br |
| CH₃ | Cl | Cl | i-Pr | H | Br | Cl | Cl | Cl | i-Pr | H | Br |
| CH₃ | Cl | Cl | t-Bu | H | Br | Cl | Cl | Cl | t-Bu | H | Br |
| CH₃ | Cl | Cl | Me | Me | Br | Cl | Cl | Cl | Me | Me | Br |
| CH₃ | Cl | Br | Me | H | Cl | Cl | Cl | Br | Me | H | Cl |
| CH₃ | Cl | Br | Et | H | Cl | Cl | Cl | Br | Et | H | Cl |
| CH₃ | Cl | Br | i-Pr | H | Cl | Cl | Cl | Br | i-Pr | H | Cl |
| CH₃ | Cl | Br | t-Bu | H | Cl | Cl | Cl | Br | t-Bu | H | Cl |

TABLE 1-continued

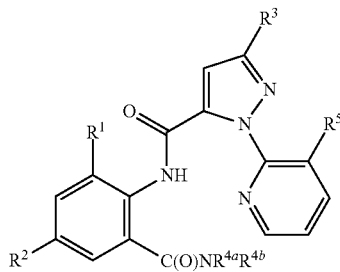

| R¹ | R² | R³ | R⁴ᵃ | R⁴ᵇ | R⁵ | R¹ | R² | R³ | R⁴ᵃ | R⁴ᵇ | R⁵ |
|---|---|---|---|---|---|---|---|---|---|---|---|
| CH₃ | Cl | Br | Me | Me | Cl | Cl | Cl | Br | Me | Me | Cl |
| CH₃ | Cl | Br | Me | H | Br | Cl | Cl | Br | Me | H | Br |
| CH₃ | Cl | Br | Et | H | Br | Cl | Cl | Br | Et | H | Br |
| CH₃ | Cl | Br | i-Pr | H | Br | Cl | Cl | Br | i-Pr | H | Br |
| CH₃ | Cl | Br | t-Bu | H | Br | Cl | Cl | Br | t-Bu | H | Br |
| CH₃ | Cl | Br | Me | Me | Br | Cl | Cl | Br | Me | Me | Br |
| CH₃ | Cl | OCH₂CF₃ | Me | H | Cl | Cl | Cl | OCH₂CF₃ | Me | H | Cl |
| CH₃ | Cl | OCH₂CF₃ | Et | H | Cl | Cl | Cl | OCH₂CF₃ | Et | H | Cl |
| CH₃ | Cl | OCH₂CF₃ | i-Pr | H | Cl | Cl | Cl | OCH₂CF₃ | i-Pr | H | Cl |
| CH₃ | Cl | OCH₂CF₃ | t-Bu | H | Cl | Cl | Cl | OCH₂CF₃ | t-Bu | H | Cl |
| CH₃ | Cl | OCH₂CF₃ | Me | Me | Cl | Cl | Cl | OCH₂CF₃ | Me | Me | Cl |
| CH₃ | Cl | OCH₂CF₃ | Me | H | Br | Cl | Cl | OCH₂CF₃ | Me | H | Br |
| CH₃ | Cl | OCH₂CF₃ | Et | H | Br | Cl | Cl | OCH₂CF₃ | Et | H | Br |
| CH₃ | Cl | OCH₂CF₃ | i-Pr | H | Br | Cl | Cl | OCH₂CF₃ | i-Pr | H | Br |
| CH₃ | Cl | OCH₂CF₃ | t-Bu | H | Br | Cl | Cl | OCH₂CF₃ | t-Bu | H | Br |
| CH₃ | Cl | OCH₂CF₃ | Me | Me | Br | Cl | Cl | OCH₂CF₃ | Me | Me | Br |
| CH₃ | Br | CF₃ | Me | H | Cl | Cl | Br | CF₃ | Me | H | Cl |
| CH₃ | Br | CF₃ | Et | H | Cl | Cl | Br | CF₃ | Et | H | Cl |
| CH₃ | Br | CF₃ | i-Pr | H | Cl | Cl | Br | CF₃ | i-Pr | H | Cl |
| CH₃ | Br | CF₃ | t-Bu | H | Cl | Cl | Br | CF₃ | t-Bu | H | Cl |
| CH₃ | Br | CF₃ | Me | Me | Cl | Cl | Br | CF₃ | Me | Me | Cl |
| CH₃ | Br | CF₃ | Me | H | Br | Cl | Br | CF₃ | Me | H | Br |
| CH₃ | Br | CF₃ | Et | H | Br | Cl | Br | CF₃ | Et | H | Br |
| CH₃ | Br | CF₃ | i-Pr | H | Br | Cl | Br | CF₃ | i-Pr | H | Br |
| CH₃ | Br | CF₃ | t-Bu | H | Br | Cl | Br | CF₃ | t-Bu | H | Br |
| CH₃ | Br | CF₃ | Me | Me | Br | Cl | Br | CF₃ | Me | Me | Br |
| CH₃ | Br | Cl | Me | H | Cl | Cl | Br | Cl | Me | H | Cl |
| CH₃ | Br | Cl | Et | H | Cl | Cl | Br | Cl | Et | H | Cl |
| CH₃ | Br | Cl | i-Pr | H | Cl | Cl | Br | Cl | i-Pr | H | Cl |
| CH₃ | Br | Cl | t-Bu | H | Cl | Cl | Br | Cl | t-Bu | H | Cl |
| CH₃ | Br | Cl | Me | Me | Cl | Cl | Br | Cl | Me | Me | Cl |
| CH₃ | Br | Cl | Me | H | Br | Cl | Br | Cl | Me | H | Br |
| CH₃ | Br | Cl | Et | H | Br | Cl | Br | Cl | Et | H | Br |
| CH₃ | Br | Cl | i-Pr | H | Br | Cl | Br | Cl | i-Pr | H | Br |
| CH₃ | Br | Cl | t-Bu | H | Br | Cl | Br | Cl | t-Bu | H | Br |
| CH₃ | Br | Cl | Me | Me | Br | Cl | Br | Cl | Me | Me | Br |
| CH₃ | Br | Br | Me | H | Cl | Cl | Br | Br | Me | H | Cl |
| CH₃ | Br | Br | Et | H | Cl | Cl | Br | Br | Et | H | Cl |
| CH₃ | Br | Br | i-Pr | H | Cl | Cl | Br | Br | i-Pr | H | Cl |
| CH₃ | Br | Br | t-Bu | H | Cl | Cl | Br | Br | t-Bu | H | Cl |
| CH₃ | Br | Br | Me | Me | Cl | Cl | Br | Br | Me | Me | Cl |
| CH₃ | Br | Br | Me | H | Br | Cl | Br | Br | Me | H | Br |
| CH₃ | Br | Br | Et | H | Br | Cl | Br | Br | Et | H | Br |
| CH₃ | Br | Br | i-Pr | H | Br | Cl | Br | Br | i-Pr | H | Br |
| CH₃ | Br | Br | t-Bu | H | Br | Cl | Br | Br | t-Bu | H | Br |
| CH₃ | Br | Br | Me | Me | Br | Cl | Br | Br | Me | Me | Br |
| CH₃ | Br | OCH₂CF₃ | Me | H | Cl | Cl | Br | OCH₂CF₃ | Me | H | Cl |
| CH₃ | Br | OCH₂CF₃ | Et | H | Cl | Cl | Br | OCH₂CF₃ | Et | H | Cl |
| CH₃ | Br | OCH₂CF₃ | i-Pr | H | Cl | Cl | Br | OCH₂CF₃ | i-Pr | H | Cl |
| CH₃ | Br | OCH₂CF₃ | t-Bu | H | Cl | Cl | Br | OCH₂CF₃ | t-Bu | H | Cl |
| CH₃ | Br | OCH₂CF₃ | Me | Me | Cl | Cl | Br | OCH₂CF₃ | Me | Me | Cl |
| CH₃ | Br | OCH₂CF₃ | Me | H | Br | Cl | Br | OCH₂CF₃ | Me | H | Br |
| CH₃ | Br | OCH₂CF₃ | Et | H | Br | Cl | Br | OCH₂CF₃ | Et | H | Br |
| CH₃ | Br | OCH₂CF₃ | i-Pr | H | Br | Cl | Br | OCH₂CF₃ | i-Pr | H | Br |
| CH₃ | Br | OCH₂CF₃ | t-Bu | H | Br | Cl | Br | OCH₂CF₃ | t-Bu | H | Br |
| CH₃ | Br | OCH₂CF₃ | Me | Me | Br | Cl | Br | OCH₂CF₃ | Me | Me | Br |
| CH₃ | I | CF₃ | Me | H | Cl | Cl | I | CF₃ | Me | H | Cl |
| CH₃ | I | CF₃ | Et | H | Cl | Cl | I | CF₃ | Et | H | Cl |
| CH₃ | I | CF₃ | i-Pr | H | Cl | Cl | I | CF₃ | i-Pr | H | Cl |
| CH₃ | I | CF₃ | t-Bu | H | Cl | Cl | I | CF₃ | t-Bu | H | Cl |
| CH₃ | I | CF₃ | Me | Me | Cl | Cl | I | CF₃ | Me | Me | Cl |
| CH₃ | I | CF₃ | Me | H | Br | Cl | I | CF₃ | Me | H | Br |
| CH₃ | I | CF₃ | Et | H | Br | Cl | I | CF₃ | Et | H | Br |
| CH₃ | I | CF₃ | i-Pr | H | Br | Cl | I | CF₃ | i-Pr | H | Br |

TABLE 1-continued

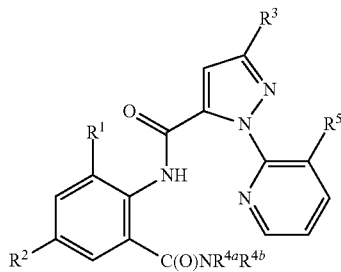

| R¹ | R² | R³ | R⁴ᵃ | R⁴ᵇ | R⁵ | R¹ | R² | R³ | R⁴ᵃ | R⁴ᵇ | R⁵ |
|---|---|---|---|---|---|---|---|---|---|---|---|
| CH₃ | I | CF₃ | t-Bu | H | Br | Cl | I | CF₃ | t-Bu | H | Br |
| CH₃ | I | CF₃ | Me | Me | Br | Cl | I | CF₃ | Me | Me | Br |
| CH₃ | I | Cl | Me | H | Cl | Cl | I | Cl | Me | H | Cl |
| CH₃ | I | Cl | Et | H | Cl | Cl | I | Cl | Et | H | Cl |
| CH₃ | I | Cl | i-Pr | H | Cl | Cl | I | Cl | i-Pr | H | Cl |
| CH₃ | I | Cl | t-Bu | H | Cl | Cl | I | Cl | t-Bu | H | Cl |
| CH₃ | I | Cl | Me | Me | Cl | Cl | I | Cl | Me | Me | Cl |
| CH₃ | I | Cl | Me | H | Br | Cl | I | Cl | Me | H | Br |
| CH₃ | I | Cl | Et | H | Br | Cl | I | Cl | Et | H | Br |
| CH₃ | I | Cl | i-Pr | H | Br | Cl | I | Cl | i-Pr | H | Br |
| CH₃ | I | Cl | t-Bu | H | Br | Cl | I | Cl | t-Bu | H | Br |
| CH₃ | I | Cl | Me | Me | Br | Cl | I | Cl | Me | Me | Br |
| CH₃ | I | Br | Me | H | Cl | Cl | I | Br | Me | H | Cl |
| CH₃ | I | Br | Et | H | Cl | Cl | I | Br | Et | H | Cl |
| CH₃ | I | Br | i-Pr | H | Cl | Cl | I | Br | i-Pr | H | Cl |
| CH₃ | I | Br | t-Bu | H | Cl | Cl | I | Br | t-Bu | H | Cl |
| CH₃ | I | Br | Me | Me | Cl | Cl | I | Br | Me | Me | Cl |
| CH₃ | I | Br | Me | H | Br | Cl | I | Br | Me | H | Br |
| CH₃ | I | Br | Et | H | Br | Cl | I | Br | Et | H | Br |
| CH₃ | I | Br | i-Pr | H | Br | Cl | I | Br | i-Pr | H | Br |
| CH₃ | I | Br | t-Bu | H | Br | Cl | I | Br | t-Bu | H | Br |
| CH₃ | I | Br | Me | Me | Br | Cl | I | Br | Me | Me | Br |
| CH₃ | I | OCH₂CF₃ | Me | H | Cl | Cl | I | OCH₂CF₃ | Me | H | Cl |
| CH₃ | I | OCH₂CF₃ | Et | H | Cl | Cl | I | OCH₂CF₃ | Et | H | Cl |
| CH₃ | I | OCH₂CF₃ | i-Pr | H | Cl | Cl | I | OCH₂CF₃ | i-Pr | H | Cl |
| CH₃ | I | OCH₂CF₃ | t-Bu | H | Cl | Cl | I | OCH₂CF₃ | t-Bu | H | Cl |
| CH₃ | I | OCH₂CF₃ | Me | Me | Cl | Cl | I | OCH₂CF₃ | Me | Me | Cl |
| CH₃ | I | OCH₂CF₃ | Me | H | Br | Cl | I | OCH₂CF₃ | Me | H | Br |
| CH₃ | I | OCH₂CF₃ | Et | H | Br | Cl | I | OCH₂CF₃ | Et | H | Br |
| CH₃ | I | OCH₂CF₃ | i-Pr | H | Br | Cl | I | OCH₂CF₃ | i-Pr | H | Br |
| CH₃ | I | OCH₂CF₃ | t-Bu | H | Br | Cl | I | OCH₂CF₃ | t-Bu | H | Br |
| CH₃ | I | OCH₂CF₃ | Me | Me | Br | Cl | I | OCH₂CF₃ | Me | Me | Br |
| CH₃ | CF₃ | CF₃ | Me | H | Cl | Cl | CF₃ | CF₃ | Me | H | Cl |
| CH₃ | CF₃ | CF₃ | Et | H | Cl | Cl | CF₃ | CF₃ | Et | H | Cl |
| CH₃ | CF₃ | CF₃ | i-Pr | H | Cl | Cl | CF₃ | CF₃ | i-Pr | H | Cl |
| CH₃ | CF₃ | CF₃ | t-Bu | H | Cl | Cl | CF₃ | CF₃ | t-Bu | H | Cl |
| CH₃ | CF₃ | CF₃ | Me | Me | Cl | Cl | CF₃ | CF₃ | Me | Me | Cl |
| CH₃ | CF₃ | CF₃ | Me | H | Br | Cl | CF₃ | CF₃ | Me | H | Br |
| CH₃ | CF₃ | CF₃ | Et | H | Br | Cl | CF₃ | CF₃ | Et | H | Br |
| CH₃ | CF₃ | CF₃ | i-Pr | H | Br | Cl | CF₃ | CF₃ | i-Pr | H | Br |
| CH₃ | CF₃ | CF₃ | t-Bu | H | Br | Cl | CF₃ | CF₃ | t-Bu | H | Br |
| CH₃ | CF₃ | CF₃ | Me | Me | Br | Cl | CF₃ | CF₃ | Me | Me | Br |
| CH₃ | CF₃ | Cl | Me | H | Cl | Cl | CF₃ | Cl | Me | H | Cl |
| CH₃ | CF₃ | Cl | Et | H | Cl | Cl | CF₃ | Cl | Et | H | Cl |
| CH₃ | CF₃ | Cl | i-Pr | H | Cl | Cl | CF₃ | Cl | i-Pr | H | Cl |
| CH₃ | CF₃ | Cl | t-Bu | H | Cl | Cl | CF₃ | Cl | t-Bu | H | Cl |
| CH₃ | CF₃ | Cl | Me | Me | Cl | Cl | CF₃ | Cl | Me | Me | Cl |
| CH₃ | CF₃ | Cl | Me | H | Br | Cl | CF₃ | Cl | Me | H | Br |
| CH₃ | CF₃ | Cl | Et | H | Br | Cl | CF₃ | Cl | Et | H | Br |
| CH₃ | CF₃ | Cl | i-Pr | H | Br | Cl | CF₃ | Cl | i-Pr | H | Br |
| CH₃ | CF₃ | Cl | t-Bu | H | Br | Cl | CF₃ | Cl | t-Bu | H | Br |
| CH₃ | CF₃ | Cl | Me | Me | Br | Cl | CF₃ | Cl | Me | Me | Br |
| CH₃ | CF₃ | Br | Me | H | Cl | Cl | CF₃ | Br | Me | H | Cl |
| CH₃ | CF₃ | Br | Et | H | Cl | Cl | CF₃ | Br | Et | H | Cl |
| CH₃ | CF₃ | Br | i-Pr | H | Cl | Cl | CF₃ | Br | i-Pr | H | Cl |
| CH₃ | CF₃ | Br | t-Bu | H | Cl | Cl | CF₃ | Br | t-Bu | H | Cl |
| CH₃ | CF₃ | Br | Me | Me | Cl | Cl | CF₃ | Br | Me | Me | Cl |
| CH₃ | CF₃ | Br | Me | H | Br | Cl | CF₃ | Br | Me | H | Br |
| CH₃ | CF₃ | Br | Et | H | Br | Cl | CF₃ | Br | Et | H | Br |
| CH₃ | CF₃ | Br | i-Pr | H | Br | Cl | CF₃ | Br | i-Pr | H | Br |
| CH₃ | CF₃ | Br | t-Bu | H | Br | Cl | CF₃ | Br | t-Bu | H | Br |
| CH₃ | CF₃ | Br | Me | Me | Br | Cl | CF₃ | Br | Me | Me | Br |
| CH₃ | CF₃ | OCH₂CF₃ | Me | H | Cl | Cl | CF₃ | OCH₂CF₃ | Me | H | Cl |
| CH₃ | CF₃ | OCH₂CF₃ | Et | H | Cl | Cl | CF₃ | OCH₂CF₃ | Et | H | Cl |

TABLE 1-continued

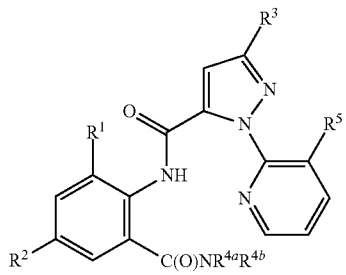

| R¹ | R² | R³ | R⁴ᵃ | R⁴ᵇ | R⁵ | R¹ | R² | R³ | R⁴ᵃ | R⁴ᵇ | R⁵ |
|---|---|---|---|---|---|---|---|---|---|---|---|
| CH₃ | CF₃ | OCH₂CF₃ | i-Pr | H | Cl | Cl | CF₃ | OCH₂CF₃ | i-Pr | H | Cl |
| CH₃ | CF₃ | OCH₂CF₃ | t-Bu | H | Cl | Cl | CF₃ | OCH₂CF₃ | t-Bu | H | Cl |
| CH₃ | CF₃ | OCH₂CF₃ | Me | Me | Cl | Cl | CF₃ | OCH₂CF₃ | Me | Me | Cl |
| CH₃ | CF₃ | OCH₂CF₃ | Me | H | Br | Cl | CF₃ | OCH₂CF₃ | Me | H | Br |
| CH₃ | CF₃ | OCH₂CF₃ | Et | H | Br | Cl | CF₃ | OCH₂CF₃ | Et | H | Br |
| CH₃ | CF₃ | OCH₂CF₃ | i-Pr | H | Br | Cl | CF₃ | OCH₂CF₃ | i-Pr | H | Br |
| CH₃ | CF₃ | OCH₂CF₃ | t-Bu | H | Br | Cl | CF₃ | OCH₂CF₃ | t-Bu | H | Br |
| CH₃ | CF₃ | OCH₂CF₃ | Me | Me | Br | Cl | CF₃ | OCH₂CF₃ | Me | Me | Br |
| CH₃ | Cl | Cl | n-Pr | H | Cl | Cl | Cl | Cl | n-Pr | H | Cl |
| CH₃ | Cl | Cl | n-Bu | H | Cl | Cl | Cl | Cl | n-Bu | H | Cl |
| CH₃ | Cl | Cl | s-Bu | H | Cl | Cl | Cl | Cl | s-Bu | H | Cl |
| CH₃ | Cl | Cl | i-Bu | H | Cl | Cl | Cl | Cl | i-Bu | H | Cl |
| CH₃ | Cl | Cl | Et | Me | Cl | Cl | Cl | Cl | Et | Me | Cl |
| F | F | CF₃ | Me | H | Cl | Br | F | CF₃ | Me | H | Cl |
| F | F | CF₃ | Et | H | Cl | Br | F | CF₃ | Et | H | Cl |
| F | F | CF₃ | i-Pr | H | Cl | Br | F | CF₃ | i-Pr | H | Cl |
| F | F | CF₃ | t-Bu | H | Cl | Br | F | CF₃ | t-Bu | H | Cl |
| F | F | CF₃ | Me | Me | Cl | Br | F | CF₃ | Me | Me | Cl |
| F | F | CF₃ | Me | H | Br | Br | F | CF₃ | Me | H | Br |
| F | F | CF₃ | Et | H | Br | Br | F | CF₃ | Et | H | Br |
| F | F | CF₃ | i-Pr | H | Br | Br | F | CF₃ | i-Pr | H | Br |
| F | F | CF₃ | t-Bu | H | Br | Br | F | CF₃ | t-Bu | H | Br |
| F | F | CF₃ | Me | Me | Br | Br | F | CF₃ | Me | Me | Br |
| F | F | Cl | Me | H | Cl | Br | F | Cl | Me | H | Cl |
| F | F | Cl | Et | H | Cl | Br | F | Cl | Et | H | Cl |
| F | F | Cl | i-Pr | H | Cl | Br | F | Cl | i-Pr | H | Cl |
| F | F | Cl | t-Bu | H | Cl | Br | F | Cl | t-Bu | H | Cl |
| F | F | Cl | Me | Me | Cl | Br | F | Cl | Me | Me | Cl |
| F | F | Cl | Me | H | Br | Br | F | Cl | Me | H | Br |
| F | F | Cl | Et | H | Br | Br | F | Cl | Et | H | Br |
| F | F | Cl | i-Pr | H | Br | Br | F | Cl | i-Pr | H | Br |
| F | F | Cl | t-Bu | H | Br | Br | F | Cl | t-Bu | H | Br |
| F | F | Cl | Me | Me | Br | Br | F | Cl | Me | Me | Br |
| F | F | Br | Me | H | Cl | Br | F | Br | Me | H | Cl |
| F | F | Br | Et | H | Cl | Br | F | Br | Et | H | Cl |
| F | F | Br | i-Pr | H | Cl | Br | F | Br | i-Pr | H | Cl |
| F | F | Br | t-Bu | H | Cl | Br | F | Br | t-Bu | H | Cl |
| F | F | Br | Me | Me | Cl | Br | F | Br | Me | Me | Cl |
| F | F | Br | Me | H | Br | Br | F | Br | Me | H | Br |
| F | F | Br | Et | H | Br | Br | F | Br | Et | H | Br |
| F | F | Br | i-Pr | H | Br | Br | F | Br | i-Pr | H | Br |
| F | F | Br | t-Bu | H | Br | Br | F | Br | t-Bu | H | Br |
| F | F | Br | Me | Me | Br | Br | F | Br | Me | Me | Br |
| F | F | OCH₂CF₃ | Me | H | Cl | Br | F | OCH₂CF₃ | Me | H | Cl |
| F | F | OCH₂CF₃ | Et | H | Cl | Br | F | OCH₂CF₃ | Et | H | Cl |
| F | F | OCH₂CF₃ | i-Pr | H | Cl | Br | F | OCH₂CF₃ | i-Pr | H | Cl |
| F | F | OCH₂CF₃ | t-Bu | H | Cl | Br | F | OCH₂CF₃ | t-Bu | H | Cl |
| F | F | OCH₂CF₃ | Me | Me | Cl | Br | F | OCH₂CF₃ | Me | Me | Cl |
| F | F | OCH₂CF₃ | Me | H | Br | Br | F | OCH₂CF₃ | Me | H | Br |
| F | F | OCH₂CF₃ | Et | H | Br | Br | F | OCH₂CF₃ | Et | H | Br |
| F | F | OCH₂CF₃ | i-Pr | H | Br | Br | F | OCH₂CF₃ | i-Pr | H | Br |
| F | F | OCH₂CF₃ | t-Bu | H | Br | Br | F | OCH₂CF₃ | t-Bu | H | Br |
| F | F | OCH₂CF₃ | Me | Me | Br | Br | F | OCH₂CF₃ | Me | Me | Br |
| F | Cl | CF₃ | Me | H | Cl | Br | Cl | CF₃ | Me | H | Cl |
| F | Cl | CF₃ | Et | H | Cl | Br | Cl | CF₃ | Et | H | Cl |
| F | Cl | CF₃ | i-Pr | H | Cl | Br | Cl | CF₃ | i-Pr | H | Cl |
| F | Cl | CF₃ | t-Bu | H | Cl | Br | Cl | CF₃ | t-Bu | H | Cl |
| F | Cl | CF₃ | Me | Me | Cl | Br | Cl | CF₃ | Me | Me | Cl |
| F | Cl | CF₃ | Me | H | Br | Br | Cl | CF₃ | Me | H | Br |
| F | Cl | CF₃ | Et | H | Br | Br | Cl | CF₃ | Et | H | Br |
| F | Cl | CF₃ | i-Pr | H | Br | Br | Cl | CF₃ | i-Pr | H | Br |
| F | Cl | CF₃ | t-Bu | H | Br | Br | Cl | CF₃ | t-Bu | H | Br |
| F | Cl | CF₃ | Me | Me | Br | Br | Cl | CF₃ | Me | Me | Br |
| F | Cl | Cl | Me | H | Cl | Br | Cl | Cl | Me | H | Cl |

TABLE 1-continued

| R¹ | R² | R³ | R⁴ᵃ | R⁴ᵇ | R⁵ | R¹ | R² | R³ | R⁴ᵃ | R⁴ᵇ | R⁵ |
|---|---|---|---|---|---|---|---|---|---|---|---|
| F | Cl | Cl | Et | H | Cl | Br | Cl | Cl | Et | H | Cl |
| F | Cl | Cl | i-Pr | H | Cl | Br | Cl | Cl | i-Pr | H | Cl |
| F | Cl | Cl | t-Bu | H | Cl | Br | Cl | Cl | t-Bu | H | Cl |
| F | Cl | Cl | Me | Me | Cl | Br | Cl | Cl | Me | Me | Cl |
| F | Cl | Cl | Me | H | Br | Br | Cl | Cl | Me | H | Br |
| F | Cl | Cl | Et | H | Br | Br | Cl | Cl | Et | H | Br |
| F | Cl | Cl | i-Pr | H | Br | Br | Cl | Cl | i-Pr | H | Br |
| F | Cl | Cl | t-Bu | H | Br | Br | Cl | Cl | t-Bu | H | Br |
| F | Cl | Cl | Me | Me | Br | Br | Cl | Cl | Me | Me | Br |
| F | Cl | Br | Me | H | Cl | Br | Cl | Br | Me | H | Cl |
| F | Cl | Br | Et | H | Cl | Br | Cl | Br | Et | H | Cl |
| F | Cl | Br | i-Pr | H | Cl | Br | Cl | Br | i-Pr | H | Cl |
| F | Cl | Br | t-Bu | H | Cl | Br | Cl | Br | t-Bu | H | Cl |
| F | Cl | Br | Me | Me | Cl | Br | Cl | Br | Me | Me | Cl |
| F | Cl | Br | Me | H | Br | Br | Cl | Br | Me | H | Br |
| F | Cl | Br | Et | H | Br | Br | Cl | Br | Et | H | Br |
| F | Cl | Br | i-Pr | H | Br | Br | Cl | Br | i-Pr | H | Br |
| F | Cl | Br | t-Bu | H | Br | Br | Cl | Br | t-Bu | H | Br |
| F | Cl | Br | Me | Me | Br | Br | Cl | Br | Me | Me | Br |
| F | Cl | OCH₂CF₃ | Me | H | Cl | Br | Cl | OCH₂CF₃ | Me | H | Cl |
| F | Cl | OCH₂CF₃ | Et | H | Cl | Br | Cl | OCH₂CF₃ | Et | H | Cl |
| F | Cl | OCH₂CF₃ | i-Pr | H | Cl | Br | Cl | OCH₂CF₃ | i-Pr | H | Cl |
| F | Cl | OCH₂CF₃ | t-Bu | H | Cl | Br | Cl | OCH₂CF₃ | t-Bu | H | Cl |
| F | Cl | OCH₂CF₃ | Me | Me | Cl | Br | Cl | OCH₂CF₃ | Me | Me | Cl |
| F | Cl | OCH₂CF₃ | Me | H | Br | Br | Cl | OCH₂CF₃ | Me | H | Br |
| F | Cl | OCH₂CF₃ | Et | H | Br | Br | Cl | OCH₂CF₃ | Et | H | Br |
| F | Cl | OCH₂CF₃ | i-Pr | H | Br | Br | Cl | OCH₂CF₃ | i-Pr | H | Br |
| F | Cl | OCH₂CF₃ | t-Bu | H | Br | Br | Cl | OCH₂CF₃ | t-Bu | H | Br |
| F | Cl | OCH₂CF₃ | Me | Me | Br | Br | Cl | OCH₂CF₃ | Me | Me | Br |
| F | Br | CF₃ | Me | H | Cl | Br | Br | CF₃ | Me | H | Cl |
| F | Br | CF₃ | Et | H | Cl | Br | Br | CF₃ | Et | H | Cl |
| F | Br | CF₃ | i-Pr | H | Cl | Br | Br | CF₃ | i-Pr | H | Cl |
| F | Br | CF₃ | t-Bu | H | Cl | Br | Br | CF₃ | t-Bu | H | Cl |
| F | Br | CF₃ | Me | Me | Cl | Br | Br | CF₃ | Me | Me | Cl |
| F | Br | CF₃ | Me | H | Br | Br | Br | CF₃ | Me | H | Br |
| F | Br | CF₃ | Et | H | Br | Br | Br | CF₃ | Et | H | Br |
| F | Br | CF₃ | i-Pr | H | Br | Br | Br | CF₃ | i-Pr | H | Br |
| F | Br | CF₃ | t-Bu | H | Br | Br | Br | CF₃ | t-Bu | H | Br |
| F | Br | CF₃ | Me | Me | Br | Br | Br | CF₃ | Me | Me | Br |
| F | Br | Cl | Me | H | Cl | Br | Br | Cl | Me | H | Cl |
| F | Br | Cl | Et | H | Cl | Br | Br | Cl | Et | H | Cl |
| F | Br | Cl | i-Pr | H | Cl | Br | Br | Cl | i-Pr | H | Cl |
| F | Br | Cl | t-Bu | H | Cl | Br | Br | Cl | t-Bu | H | Cl |
| F | Br | Cl | Me | Me | Cl | Br | Br | Cl | Me | Me | Cl |
| F | Br | Cl | Me | H | Br | Br | Br | Cl | Me | H | Br |
| F | Br | Cl | Et | H | Br | Br | Br | Cl | Et | H | Br |
| F | Br | Cl | i-Pr | H | Br | Br | Br | Cl | i-Pr | H | Br |
| F | Br | Cl | t-Bu | H | Br | Br | Br | Cl | t-Bu | H | Br |
| F | Br | Cl | Me | Me | Br | Br | Br | Cl | Me | Me | Br |
| F | Br | Br | Me | H | Cl | Br | Br | Br | Me | H | Cl |
| F | Br | Br | Et | H | Cl | Br | Br | Br | Et | H | Cl |
| F | Br | Br | i-Pr | H | Cl | Br | Br | Br | i-Pr | H | Cl |
| F | Br | Br | t-Bu | H | Cl | Br | Br | Br | t-Bu | H | Cl |
| F | Br | Br | Me | Me | Cl | Br | Br | Br | Me | Me | Cl |
| F | Br | Br | Me | H | Br | Br | Br | Br | Me | H | Br |
| F | Br | Br | Et | H | Br | Br | Br | Br | Et | H | Br |
| F | Br | Br | i-Pr | H | Br | Br | Br | Br | i-Pr | H | Br |
| F | Br | Br | t-Bu | H | Br | Br | Br | Br | t-Bu | H | Br |
| F | Br | Br | Me | Me | Br | Br | Br | Br | Me | Me | Br |
| F | Br | OCH₂CF₃ | Me | H | Cl | Br | Br | OCH₂CF₃ | Me | H | Cl |
| F | Br | OCH₂CF₃ | Et | H | Cl | Br | Br | OCH₂CF₃ | Et | H | Cl |
| F | Br | OCH₂CF₃ | i-Pr | H | Cl | Br | Br | OCH₂CF₃ | i-Pr | H | Cl |
| F | Br | OCH₂CF₃ | t-Bu | H | Cl | Br | Br | OCH₂CF₃ | t-Bu | H | Cl |
| F | Br | OCH₂CF₃ | Me | Me | Cl | Br | Br | OCH₂CF₃ | Me | Me | Cl |

TABLE 1-continued

| R¹ | R² | R³ | R⁴ᵃ | R⁴ᵇ | R⁵ | R¹ | R² | R³ | R⁴ᵃ | R⁴ᵇ | R⁵ |
|---|---|---|---|---|---|---|---|---|---|---|---|
| F | Br | OCH₂CF₃ | Me | H | Br | Br | Br | OCH₂CF₃ | Me | H | Br |
| F | Br | OCH₂CF₃ | Et | H | Br | Br | Br | OCH₂CF₃ | Et | H | Br |
| F | Br | OCH₂CF₃ | i-Pr | H | Br | Br | Br | OCH₂CF₃ | i-Pr | H | Br |
| F | Br | OCH₂CF₃ | t-Bu | H | Br | Br | Br | OCH₂CF₃ | t-Bu | H | Br |
| F | Br | OCH₂CF₃ | Me | Me | Br | Br | Br | OCH₂CF₃ | Me | Me | Br |
| F | I | CF₃ | Me | H | Cl | Br | I | CF₃ | Me | H | Cl |
| F | I | CF₃ | Et | H | Cl | Br | I | CF₃ | Et | H | Cl |
| F | I | CF₃ | i-Pr | H | Cl | Br | I | CF₃ | i-Pr | H | Cl |
| F | I | CF₃ | t-Bu | H | Cl | Br | I | CF₃ | t-Bu | H | Cl |
| F | I | CF₃ | Me | Me | Cl | Br | I | CF₃ | Me | Me | Cl |
| F | I | CF₃ | Me | H | Br | Br | I | CF₃ | Me | H | Br |
| F | I | CF₃ | Et | H | Br | Br | I | CF₃ | Et | H | Br |
| F | I | CF₃ | i-Pr | H | Br | Br | I | CF₃ | i-Pr | H | Br |
| F | I | CF₃ | t-Bu | H | Br | Br | I | CF₃ | t-Bu | H | Br |
| F | I | CF₃ | Me | Me | Br | Br | I | CF₃ | Me | Me | Br |
| F | I | Cl | Me | H | Cl | Br | I | Cl | Me | H | Cl |
| F | I | Cl | Et | H | Cl | Br | I | Cl | Et | H | Cl |
| F | I | Cl | i-Pr | H | Cl | Br | I | Cl | i-Pr | H | Cl |
| F | I | Cl | t-Bu | H | Cl | Br | I | Cl | t-Bu | H | Cl |
| F | I | Cl | Me | Me | Cl | Br | I | Cl | Me | Me | Cl |
| F | I | Cl | Me | H | Br | Br | I | Cl | Me | H | Br |
| F | I | Cl | Et | H | Br | Br | I | Cl | Et | H | Br |
| F | I | Cl | i-Pr | H | Br | Br | I | Cl | i-Pr | H | Br |
| F | I | Cl | t-Bu | H | Br | Br | I | Cl | t-Bu | H | Br |
| F | I | Cl | Me | Me | Br | Br | I | Cl | Me | Me | Br |
| F | I | Br | Me | H | Cl | Br | I | Br | Me | H | Cl |
| F | I | Br | Et | H | Cl | Br | I | Br | Et | H | Cl |
| F | I | Br | i-Pr | H | Cl | Br | I | Br | i-Pr | H | Cl |
| F | I | Br | t-Bu | H | Cl | Br | I | Br | t-Bu | H | Cl |
| F | I | Br | Me | Me | Cl | Br | I | Br | Me | Me | Cl |
| F | I | Br | Me | H | Br | Br | I | Br | Me | H | Br |
| F | I | Br | Et | H | Br | Br | I | Br | Et | H | Br |
| F | I | Br | i-Pr | H | Br | Br | I | Br | i-Pr | H | Br |
| F | I | Br | t-Bu | H | Br | Br | I | Br | t-Bu | H | Br |
| F | I | Br | Me | Me | Br | Br | I | Br | Me | Me | Br |
| F | I | OCH₂CF₃ | Me | H | Cl | Br | I | OCH₂CF₃ | Me | H | Cl |
| F | I | OCH₂CF₃ | Et | H | Cl | Br | I | OCH₂CF₃ | Et | H | Cl |
| F | I | OCH₂CF₃ | i-Pr | H | Cl | Br | I | OCH₂CF₃ | i-Pr | H | Cl |
| F | I | OCH₂CF₃ | t-Bu | H | Cl | Br | I | OCH₂CF₃ | t-Bu | H | Cl |
| F | I | OCH₂CF₃ | Me | Me | Cl | Br | I | OCH₂CF₃ | Me | Me | Cl |
| F | I | OCH₂CF₃ | Me | H | Br | Br | I | OCH₂CF₃ | Me | H | Br |
| F | I | OCH₂CF₃ | Et | H | Br | Br | I | OCH₂CF₃ | Et | H | Br |
| F | I | OCH₂CF₃ | i-Pr | H | Br | Br | I | OCH₂CF₃ | i-Pr | H | Br |
| F | I | OCH₂CF₃ | t-Bu | H | Br | Br | I | OCH₂CF₃ | t-Bu | H | Br |
| F | I | OCH₂CF₃ | Me | Me | Br | Br | I | OCH₂CF₃ | Me | Me | Br |
| F | CF₃ | CF₃ | Me | H | Cl | Br | CF₃ | CF₃ | Me | H | Cl |
| F | CF₃ | CF₃ | Et | H | Cl | Br | CF₃ | CF₃ | Et | H | Cl |
| F | CF₃ | CF₃ | i-Pr | H | Cl | Br | CF₃ | CF₃ | i-Pr | H | Cl |
| F | CF₃ | CF₃ | t-Bu | H | Cl | Br | CF₃ | CF₃ | t-Bu | H | Cl |
| F | CF₃ | CF₃ | Me | Me | Cl | Br | CF₃ | CF₃ | Me | Me | Cl |
| F | CF₃ | CF₃ | Me | H | Br | Br | CF₃ | CF₃ | Me | H | Br |
| F | CF₃ | CF₃ | Et | H | Br | Br | CF₃ | CF₃ | Et | H | Br |
| F | CF₃ | CF₃ | i-Pr | H | Br | Br | CF₃ | CF₃ | i-Pr | H | Br |
| F | CF₃ | CF₃ | t-Bu | H | Br | Br | CF₃ | CF₃ | t-Bu | H | Br |
| F | CF₃ | CF₃ | Me | Me | Br | Br | CF₃ | CF₃ | Me | Me | Br |
| F | CF₃ | Cl | Me | H | Cl | Br | CF₃ | Cl | Me | H | Cl |
| F | CF₃ | Cl | Et | H | Cl | Br | CF₃ | Cl | Et | H | Cl |
| F | CF₃ | Cl | i-Pr | H | Cl | Br | CF₃ | Cl | i-Pr | H | Cl |
| F | CF₃ | Cl | t-Bu | H | Cl | Br | CF₃ | Cl | t-Bu | H | Cl |
| F | CF₃ | Cl | Me | Me | Cl | Br | CF₃ | Cl | Me | Me | Cl |
| F | CF₃ | Cl | Me | H | Br | Br | CF₃ | Cl | Me | H | Br |
| F | CF₃ | Cl | Et | H | Br | Br | CF₃ | Cl | Et | H | Br |
| F | CF₃ | Cl | i-Pr | H | Br | Br | CF₃ | Cl | i-Pr | H | Br |
| F | CF₃ | Cl | t-Bu | H | Br | Br | CF₃ | Cl | t-Bu | H | Br |

TABLE 1-continued

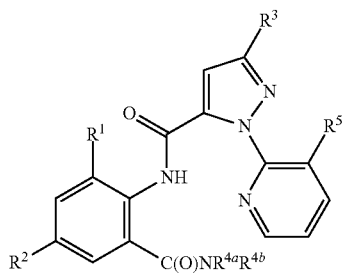

| R¹ | R² | R³ | R⁴ᵃ | R⁴ᵇ | R⁵ | R¹ | R² | R³ | R⁴ᵃ | R⁴ᵇ | R⁵ |
|---|---|---|---|---|---|---|---|---|---|---|---|
| F | CF₃ | Cl | Me | Me | Br | Br | CF₃ | Cl | Me | Me | Br |
| F | CF₃ | Br | Me | H | Cl | Br | CF₃ | Br | Me | H | Cl |
| F | CF₃ | Br | Et | H | Cl | Br | CF₃ | Br | Et | H | Cl |
| F | CF₃ | Br | i-Pr | H | Cl | Br | CF₃ | Br | i-Pr | H | Cl |
| F | CF₃ | Br | t-Bu | H | Cl | Br | CF₃ | Br | t-Bu | H | Cl |
| F | CF₃ | Br | Me | Me | Cl | Br | CF₃ | Br | Me | Me | Cl |
| F | CF₃ | Br | Me | H | Br | Br | CF₃ | Br | Me | H | Br |
| F | CF₃ | Br | Et | H | Br | Br | CF₃ | Br | Et | H | Br |
| F | CF₃ | Br | i-Pr | H | Br | Br | CF₃ | Br | i-Pr | H | Br |
| F | CF₃ | Br | t-Bu | H | Br | Br | CF₃ | Br | t-Bu | H | Br |
| F | CF₃ | Br | Me | Me | Br | Br | CF₃ | Br | Me | Me | Br |
| F | CF₃ | OCH₂CF₃ | Me | H | Cl | Br | CF₃ | OCH₂CF₃ | Me | H | Cl |
| F | CF₃ | OCH₂CF₃ | Et | H | Cl | Br | CF₃ | OCH₂CF₃ | Et | H | Cl |
| F | CF₃ | OCH₂CF₃ | i-Pr | H | Cl | Br | CF₃ | OCH₂CF₃ | i-Pr | H | Cl |
| F | CF₃ | OCH₂CF₃ | t-Bu | H | Cl | Br | CF₃ | OCH₂CF₃ | t-Bu | H | Cl |
| F | CF₃ | OCH₂CF₃ | Me | Me | Cl | Br | CF₃ | OCH₂CF₃ | Me | Me | Cl |
| F | CF₃ | OCH₂CF₃ | Me | H | Br | Br | CF₃ | OCH₂CF₃ | Me | H | Br |
| F | CF₃ | OCH₂CF₃ | Et | H | Br | Br | CF₃ | OCH₂CF₃ | Et | H | Br |
| F | CF₃ | OCH₂CF₃ | i-Pr | H | Br | Br | CF₃ | OCH₂CF₃ | i-Pr | H | Br |
| F | CF₃ | OCH₂CF₃ | t-Bu | H | Br | Br | CF₃ | OCH₂CF₃ | t-Bu | H | Br |
| F | CF₃ | OCH₂CF₃ | Me | Me | Br | Br | CF₃ | OCH₂CF₃ | Me | Me | Br |

As shown in Scheme 1 and further illustrated in Examples 1-10, the benzoxazines of Formula 2 such as those listed in Table 2 are useful for preparing the compounds of Formula 1, including those listed in Table 1.

TABLE 2

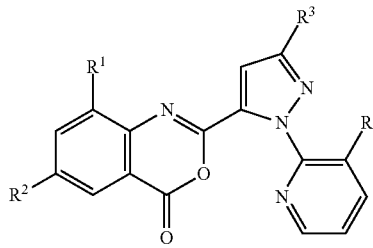

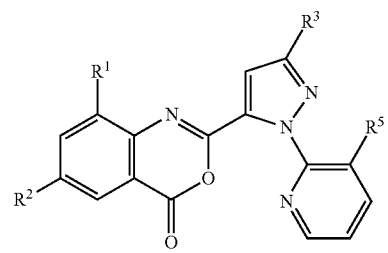

| R¹ | R² | R³ | R⁵ | R¹ | R² | R³ | R⁵ |
|---|---|---|---|---|---|---|---|
| CH₃ | F | CF₃ | Cl | Cl | F | CF₃ | Cl |
| CH₃ | F | CF₃ | Br | Cl | F | CF₃ | Br |
| CH₃ | F | Cl | Cl | Cl | F | Cl | Cl |
| CH₃ | F | Cl | Br | Cl | F | Cl | Br |
| CH₃ | F | Br | Cl | Cl | F | Br | Cl |
| CH₃ | F | Br | Br | Cl | F | Br | Br |
| CH₃ | F | OCH₂CF₃ | Cl | Cl | F | OCH₂CF₃ | Cl |
| CH₃ | F | OCH₂CF₃ | Br | Cl | F | OCH₂CF₃ | Br |
| CH₃ | Cl | CF₃ | Cl | Cl | Cl | CF₃ | Cl |
| CH₃ | Cl | CF₃ | Br | Cl | Cl | CF₃ | Br |
| CH₃ | Cl | Cl | Cl | Cl | Cl | Cl | Cl |
| CH₃ | Cl | Cl | Br | Cl | Cl | Cl | Br |
| CH₃ | Cl | Br | Cl | Cl | Cl | Br | Cl |
| CH₃ | Cl | Br | Br | Cl | Cl | Br | Br |
| CH₃ | Cl | OCH₂CF₃ | Cl | Cl | Cl | OCH₂CF₃ | Cl |
| CH₃ | Cl | OCH₂CF₃ | Br | Cl | Cl | OCH₂CF₃ | Br |
| CH₃ | Br | CF₃ | Cl | Cl | Br | CF₃ | Cl |
| CH₃ | Br | CF₃ | Br | Cl | Br | CF₃ | Br |
| CH₃ | Br | Cl | Cl | Cl | Br | Cl | Cl |
| CH₃ | Br | Cl | Br | Cl | Br | Cl | Br |
| CH₃ | Br | Br | Cl | Cl | Br | Br | Cl |
| CH₃ | Br | Br | Br | Cl | Br | Br | Br |
| CH₃ | Br | OCH₂CF₃ | Cl | Cl | Br | OCH₂CF₃ | Cl |
| CH₃ | Br | OCH₂CF₃ | Br | Cl | Br | OCH₂CF₃ | Br |
| CH₃ | I | CF₃ | Cl | Cl | I | CF₃ | Cl |
| CH₃ | I | CF₃ | Br | Cl | I | CF₃ | Br |
| CH₃ | I | Cl | Cl | Cl | I | Cl | Cl |
| CH₃ | I | Cl | Br | Cl | I | Cl | Br |
| CH₃ | I | Br | Cl | Cl | I | Br | Cl |
| CH₃ | I | Br | Br | Cl | I | Br | Br |
| CH₃ | I | OCH₂CF₃ | Cl | Cl | I | OCH₂CF₃ | Cl |
| CH₃ | I | OCH₂CF₃ | Br | Cl | I | OCH₂CF₃ | Br |
| CH₃ | CF₃ | CF₃ | Cl | Cl | CF₃ | CF₃ | Cl |
| CH₃ | CF₃ | CF₃ | Br | Cl | CF₃ | CF₃ | Br |
| CH₃ | CF₃ | Cl | Cl | Cl | CF₃ | Cl | Cl |
| CH₃ | CF₃ | Cl | Br | Cl | CF₃ | Cl | Br |
| CH₃ | CF₃ | Br | Cl | Cl | CF₃ | Br | Cl |
| CH₃ | CF₃ | Br | Br | Cl | CF₃ | Br | Br |

TABLE 2-continued

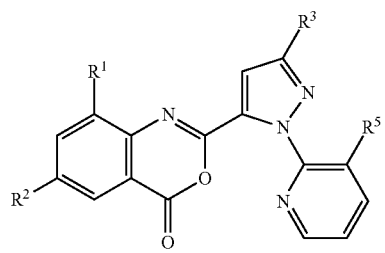

| $R^1$ | $R^2$ | $R^3$ | $R^5$ | $R^1$ | $R^2$ | $R^3$ | $R^5$ |
|---|---|---|---|---|---|---|---|
| $CH_3$ | $CF_3$ | $OCH_2CF_3$ | Cl | Cl | $CF_3$ | $OCH_2CF_3$ | Cl |
| $CH_3$ | $CF_3$ | $OCH_2CF_3$ | Br | Cl | $CF_3$ | $OCH_2CF_3$ | Br |
| F | F | $CF_3$ | Cl | Br | F | $CF_3$ | Cl |
| F | F | $CF_3$ | Br | Br | F | $CF_3$ | Br |
| F | F | Cl | Cl | Br | F | Cl | Cl |
| F | F | Cl | Br | Br | F | Cl | Br |
| F | F | Br | Cl | Br | F | Br | Cl |
| F | F | Br | Br | Br | F | Br | Br |
| F | F | $OCH_2CF_3$ | Cl | Br | F | $OCH_2CF_3$ | Cl |
| F | F | $OCH_2CF_3$ | Br | Br | F | $OCH_2CF_3$ | Br |
| F | Cl | $CF_3$ | Cl | Br | Cl | $CF_3$ | Cl |
| F | Cl | $CF_3$ | Br | Br | Cl | $CF_3$ | Br |
| F | Cl | Cl | Cl | Br | Cl | Cl | Cl |
| F | Cl | Cl | Br | Br | Cl | Cl | Br |
| F | Cl | Br | Cl | Br | Cl | Br | Cl |
| F | Cl | Br | Br | Br | Cl | Br | Br |
| F | Cl | $OCH_2CF_3$ | Cl | Br | Cl | $OCH_2CF_3$ | Cl |
| F | Cl | $OCH_2CF_3$ | Br | Br | Cl | $OCH_2CF_3$ | Br |
| F | Br | $CF_3$ | Cl | Br | Br | $CF_3$ | Cl |
| F | Br | $CF_3$ | Br | Br | Br | $CF_3$ | Br |
| F | Br | Cl | Cl | Br | Br | Cl | Cl |
| F | Br | Cl | Br | Br | Br | Cl | Br |
| F | Br | Br | Cl | Br | Br | Br | Cl |
| F | Br | Br | Br | Br | Br | Br | Br |
| F | Br | $OCH_2CF_3$ | Cl | Br | Br | $OCH_2CF_3$ | Cl |
| F | Br | $OCH_2CF_3$ | Br | Br | Br | $OCH_2CF_3$ | Br |
| F | I | $CF_3$ | Cl | Br | I | $CF_3$ | Cl |
| F | I | $CF_3$ | Br | Br | I | $CF_3$ | Br |
| F | I | Cl | Cl | Br | I | Cl | Cl |
| F | I | Cl | Br | Br | I | Cl | Br |
| F | I | Br | Cl | Br | I | Br | Cl |
| F | I | Br | Br | Br | I | Br | Br |
| F | I | $OCH_2CF_3$ | Cl | Br | I | $OCH_2CF_3$ | Cl |
| F | I | $OCH_2CF_3$ | Br | Br | I | $OCH_2CF_3$ | Br |
| F | $CF_3$ | $CF_3$ | Cl | Br | $CF_3$ | $CF_3$ | Cl |
| F | $CF_3$ | $CF_3$ | Br | Br | $CF_3$ | $CF_3$ | Br |
| F | $CF_3$ | Cl | Cl | Br | $CF_3$ | Cl | Cl |
| F | $CF_3$ | Cl | Br | Br | $CF_3$ | Cl | Br |
| F | $CF_3$ | Br | Cl | Br | $CF_3$ | Br | Cl |
| F | $CF_3$ | Br | Br | Br | $CF_3$ | Br | Br |
| F | $CF_3$ | $OCH_2CF_3$ | Cl | Br | $CF_3$ | $OCH_2CF_3$ | Cl |
| F | $CF_3$ | $OCH_2CF_3$ | Br | Br | $CF_3$ | $OCH_2CF_3$ | Br |

As shown in Scheme 2 and further illustrated in Examples 1-10, the pyrazolecarboxylic acids of Formula 4 such as those listed in Table 3 are useful in preparing the compounds of Formula 1, including those listed in Table 1.

TABLE 3

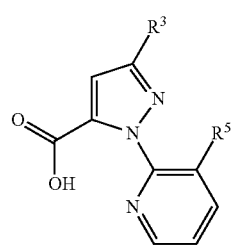

| $R^3$ | $R^5$ | $R^3$ | $R^5$ | $R^3$ | $R^5$ |
|---|---|---|---|---|---|
| $CF_3$ | Cl | $OCH_2CF_3$ | Cl | Br | Br |
| Cl | Cl | $CF_3$ | Br | $OCH_2CF_3$ | Br |
| Br | Cl | Cl | Br | | |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges that add up to 100 percent by weight.

| | Weight Percent | | |
|---|---|---|---|
| | Active Ingredient | Diluent | Surfactant |
| Water-Dispersible and Water-soluble Granules, Tablets and Powders. | 5-90 | 0-94 | 1-15 |
| Suspensions, Emulsions, Solutions (including Emulsifiable Concentrates) | 5-50 | 40-95 | 0-15 |
| Dusts | 1-25 | 70-99 | 0-5 |
| Granules and Pellets | 0.01-99 | 5-99.99 | 0-15 |
| High Strength Compositions | 90-99 | 0-10 | 0-2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide,* 2nd Ed., Interscience, New York, 1950. *McCutcheon's Detergents and Emulsifiers Annual,* Allured Publ. Corp., Ridgewood, N.J., as well as Sisely and Wood, *Encyclopedia of Surface Active Agents,* Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxy-ethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, propylene carbonate, dibasic esters, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol, benzyl and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering,* Dec. 4, 1967, pp 147-48, *Perry's Chemical Engineer's Handbook,* 4th Ed., McGraw-Hill, New York, 1963, pages 8-57 and following, and PCT Publication WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food—Environment Challenge,* T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science,* John Wiley and Sons, Inc., New York, 1961, pp 81-96; and Hance et al., *Weed Control Handbook,* 8th Ed., Blackwell Scientific Publications, Oxford, 1989.

In the following Examples, all percentages are by weight and all formulations are prepared in conventional ways. Compound numbers refer to compounds in Index Table A.

EXAMPLE A

Wettable Powder

| | |
|---|---|
| Compound 2 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

EXAMPLE B

Granule

| | |
|---|---|
| Compound 10 | 10.0% |
| attapulgite granules (low volatile matter, 0.71/0.30 mm; U.S.S. No. 25-50 sieves) | 90.0%. |

EXAMPLE C

Extruded Pellet

| | |
|---|---|
| Compound 20 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

EXAMPLE D

Emulsifiable Concentrate

| | |
|---|---|
| Compound 33 | 20.0% |
| blend of oil soluble sulfonates and polyoxyethylene ethers | 10.0% |
| isophorone | 70.0%. |

Compounds of this invention are characterized by favorable metabolic and/or soil residual patterns and exhibit activity controlling a spectrum of agronomic and non-agronomic invertebrate pests. (In the context of this disclosure "invertebrate pest control" means inhibition of invertebrate pest development (including mortality) that causes significant reduction in feeding or other injury or damage caused by the pest; related expressions are defined analogously.) As referred to in this disclosure, the term "invertebrate pest" includes arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" includes all of the helminths, such as: roundworms, heartworms, and phytophagous nematodes (Nematoda), flukes (Tematoda), Acanthocephala, and tapeworms (Cestoda). Those skilled in the art will recognize that not all compounds are equally effective against all pests. Compounds of this invention display activity against economically important agronomic and nonagronomic pests. The term "agronomic" refers to the production of field crops such as for food and fiber and includes the growth of cereal crops (e.g., wheat, oats, barley, rye, rice, maize), soybeans, vegetable crops (e.g., lettuce, cabbage, tomatoes, beans), potatoes, sweet potatoes, grapes, cotton, and tree fruits (e.g., pome fruits, stone fruits and citrus fruits). The term "nonagronomic" refers to other horticultural (e.g., forest, greenhouse, nursery or ornamental plants not grown in a field), public (human) and animal health, domestic and commercial structure, household, and stored product applications or pests. For reason of invertebrate pest control spectrum and economic importance, protection (from damage or injury caused by invertebrate pests) of agronomic crops of cotton, maize, soybeans, rice, vegetable crops, potato, sweet potato, grapes and tree fruit by controlling invertebrate pests are preferred embodiments of the invention. Agronomic or nonagronomic pests include larvae of the order Lepidoptera, such as armyworms, cutworms, loopers, and heliothines in the family Noctuidae (e.g., fall armyworm (*Spodoptera fugiperda* J. E. Smith), beet armyworm (*Spodoptera exigua* Hübner), black cutworm (*Agrotis ipsilon* Hufnagel), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworm (*Herpetogramma licarsisalis* Walker)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus)); nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella germanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)); foliar feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scaribaeidae (e.g., Japanese beetle (*Popillia japonica* Newman) and European chafer (*Rhizotrogus majalis* Razoumowsky)); carpet beetles from the family Dermestidae; wireworms from the family Elateridae; bark beetles from the family Scolytidae and flour beetles from the family Tenebrionidae. In addition, agronomic and nonagronomic pests include: adults and larvae of the order Dermaptera including earwigs from the family Forficulidae (e.g., European earwig (*Forficula auricularia* Linnaeus), black earwig (*Chelisoches morio* Fabricius)); adults and nymphs of the orders Hemiptera and Homoptera such as, plant bugs from the family Miridae, cicadas from the family Cicadidae, leafhoppers (e.g. *Empoasca* spp.) from the family Cicadellidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, cinch bugs (e.g., *Blissus* spp.) and other seed bugs from the family Lygaeidae, spittlebugs from the family Cercopidae squash bugs from the family Coreidae, and red bugs and cotton stainers from the family Pyrrhocoridae. Also included are adults and larvae of the order Acari (mites) such as spider mites and red mites in the family Tetranychidae (e.g., European red mite (*Panonychus ulmi* Koch), two spotted spider mite (*Tetranychus urticae* Koch), McDaniel mite (*Tetranychus mcdanieli* McGregor)), flat mites in the family Tenuipalpidae (e.g., citrus flat mite (*Brevipalpus lewisi* McGregor)), rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus) and scab and itch mites in the families Psoroptidae, Pyemotidae, and Sarcoptidae; adults and immatures of the order Orthoptera including grasshoppers, locusts and crickets (e.g., migratory grasshoppers (e.g., *Melanoplus sanguinipes* Fabricius, *M. differentialis* Thomas), American grasshoppers (e.g., *Schistocerca americana* Drury), desert locust (*Schistocerca gregaria* Forskal), migratory locust (*Locusta migratoria* Linnaeus), house cricket (*Acheta domesticus* Linnaeus), mole crickets (*Gryllotalpa* spp.)); adults and immatures of the order Diptera including leafminers, midges, fruit flies (Tephritidae), frit flies (e.g., *Oscinella fit* Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; adults and immatures of the order Thysanoptera including onion thrips (*Thrips tabaci* Lindeman) and other foliar feeding thrips; insect pests of the order Hymenoptera including ants (e.g., red carpenter ant (*Camponotus ferrugineus* Fabricius), black carpenter ant (*Camponotus pennsylvanicus* De Geer), Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Förster), odorous house ant (*nTapinoma sessile* Say)), bees (including carpenter bees), hornets, yellow jackets and wasps; insect pests of the order Isoptera including the eastern subterranean termite (*Reticulitermes flavipes* Kollar), western subterranean termite (*Reticulitermes hesperus* Banks), Formosan subterranean termite (*Coptotermes formosanus*

Shiraki), West Indian drywood termite (*Incisitermes immigrans* Snyder) and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus capitis* De Geer), body louse (*Pediculus humanus humanus* Linnaeus), chicken body louse (*Menacanthus stramineus* Nitzsch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch & Mulaik) and the black widow spider (Latrodectus mactans Fabricius), and centipedes in the order Scutigeromorpha such as the house centipede (*Scutigera coleoptrata* Linnaeus). Compounds of the present invention also have activity on members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as Strongylus vulgaris in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Compounds of the invention show particularly high activity against pests in the order Lepidoptera (e.g., *Alabama argillacea* Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrosis medinalis* Guenee (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittella* Fabricius (spotted bollworm), *Helicoverpa armigera* Hübner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis & Schiffermüller (grape berry moth), *Pectinophora gossypiella* Saunders (pink bollworm), *Phyllocnistis citrella* Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hübner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tuta absoluta* Meyrick (tomato leafminer)). Compounds of the invention also have commercially significant activity on members from the order Homoptera including: *Acyrthisiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid), *Eriosoma lanigerum* Hausmann (woolly apple aphid), *Hyalopterus pruni* Geoffroy (mealy plum aphid), *Lipaphis erysimi* Kaltenbach (turnip aphid), *Metopolophium dirrhodum* Walker (cereal aphid), *Macrosipum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii* Boyer de Fonscolombe (black citrus aphid), and *Toxoptera citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly), *Bemisia argentifolii* Bellows & Perring (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *Nephotettix nigropictus* Stål (rice leafhopper), *Nilaparvata lugens* Stål (brown planthopper), *Peregrinus maidis* Ashmead (corn planthopper), *Sogatella furcifera* Horvath (white-backed planthopper), *Sogatodes orizicola* Muir (rice delphacid), *Typhlocyba pomaria* McAtee white apple leafhopper, *Erythroneoura* spp. (grape leafhoppers); *Magicidada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimmon psylla). These compounds also have activity on members from the order Hemiptera including: *Acrosternum hilare* Say (green stink bug), *Anasa tristis* De Geer (squash bug), *Blissus leucopterus leucopterus* Say (chinch bug), *Corythuca gossypii* Fabricius (cotton lace bug), *Cyrtopeltis modesta* Distant (tomato bug), *Dysdercus suturellus* Herrich-Schäffer (cotton stainer), *Euchistus servus* Say (brown stink bug), *Euchistus variolarius* Palisot de Beauvois (one-spotted stink bug), *Graptosthetus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* Dallas (large milkweed bug), *Pseudatomoscelis seriatus* Reuter (cotton fleahopper). Other insect orders controlled by compounds of the invention include Thysanoptera (e.g., *Franklliniella occidentalis* Pergande (western flower thrip), *Scirthothrips citri* Moulton (citrus thrip), *Sericothrips variabilis* Beach (soybean thrip), and *Thrips tabaci* Lindeman (onion thrip); and the order Coleoptera (e.g., *Leptinotarsa decemlineata* Say (Colorado potato beetle), *Epilachna varivestis* Mulsant (Mexican bean beetle) and wireworms of the genera *Agriotes, Athous* or *Limonius*).

Compounds of this invention can also be mixed with one or more other biologically active compounds or agents including insecticides, fungicides, nematocides, bactericides, acaricides, growth regulators such as rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agricultural utility. Thus the present invention also pertains to a composition comprising a biologically effective amount of a compound of Formula 1 and an effective amount of at least one additional biologically active compound or agent and can further comprise at least one of a surfactant, a solid diluent or a liquid diluent. Examples of such biologically active compounds or agents with which compounds of this invention can be formulated are: insecticides such as abamectin, acephate, acetamiprid, amidoflumet (S-1955), avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenvalerate, fipronil, flonicamid, flucythrinate, tau-fluvalinate, flufenerim (UR-50701), flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron (XDE-007), oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin (BSN 2060), sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron; fungicides such as acibenzolar, azoxystrobin, benomyl, blasticidin-S, Bordeaux mixture (tribasic copper sulfate), bromuconazole, carpropamid, captafol, captan, carbendazim, chloroneb, chlorothalonil, copper oxychloride, copper salts, cyflufenamid, cymoxanil, cyproconazole, cyprodinil, (S)-3,5-dichloro-N-(3-chloro-1-ethyl-1-methyl-2-oxopropyl)-4-methylbenzamide (RH 7281), diclocymet (S-2900), diclomezine, dicloran, difenoconazole, (S)-3,5-dihydro-5-methyl-2-(methylthio)-5-phenyl-3-(phenylamino)-4H-imidazol-4-one (RP 407213), dimethomorph, dimoxystrobin, diniconazole, diniconazole-M, dodine, edifenphos, epoxiconazole, famoxadone, fenamidone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), flumorf/flumorlin (SYP-L190), fluoxastrobin (HEC 5725), fluquinconazole, flusilazole, flutolanil, flutriafol, folpet, fosetyl-aluminum, furalaxyl, furametapyr (S-82658), hexaconazole, ipconazole, iprobenfos, iprodione, isoprothiolane, kasugamycin, kresoxim-methyl, mancozeb, maneb, mefenoxam, mepronil, metalaxyl, metconazole, metominostrobin/fenominostrobin (S S F-126), metrafenone (AC375839), myclobutanil, neo-asozin (ferric methanearsonate), nicobifen (BAS 510), orysastrobin, oxadixyl, penconazole, pencycuron, probenazole, prochloraz, propamocarb, propiconazole, proquinazid (DPX-KQ926), prothioconazole (JAU 6476), pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, tiadinil, triadimefon, triadimenol, tricyclazole, trifloxystrobin, triticonazole, validamycin and vinclozolin; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents such as *Bacillus thuringiensis* including ssp. *aizawai* and *kurstaki*, *Bacillus thuringiensis* delta endotoxin, baculovirus, and entomopathogenic bacteria, virus and fungi. Compounds of this invention and compositions thereof can be applied to plants genetically transformed to express proteins toxic to invertebrate pests (such as *Bacillus thuringiensis* toxin). The effect of the exogenously applied invertebrate pest control compounds of this invention may be synergistic with the expressed toxin proteins.

A general reference for these agricultural protectants is *The Pesticide Manual*, 12th Edition, C. D. S. Tomlin, Ed., British Crop Protection Council, Farnham, Surrey, U.K., 2000.

Preferred insecticides and acaricides for mixing with compounds of this invention include pyrethroids such as cypermethrin, cyhalothrin, cyfluthrin, beta-cyfluthrin, esfenvalerate, fenvalerate and tralomethrin; carbamates such as fenothicarb, methomyl, oxamyl and thiodicarb; neonicotinoids such as clothianidin, imidacloprid and thiacloprid; neuronal sodium channel blockers such as indoxacarb; insecticidal macrocyclic lactones such as spinosad, abamectin, avermectin and emamectin; γ-aminobutyric acid (GABA) antagonists such as endosulfan, ethiprole and fipronil; insecticidal ureas such as flufenoxuron and triflumuron; juvenile hormone mimics such as diofenolan and pyriproxyfen; pymetrozine; and amitraz. Preferred biological agents for mixing with compounds of this invention include *Bacillus thuringiensis* and *Bacillus thuringiensis* delta endotoxin as well as naturally occurring and genetically modified viral insecticides including members of the family Baculoviridae as well as entomophagous fungi.

Most preferred mixtures include a mixture of a compound of this invention with cyhalothrin; a mixture of a compound of this invention with beta-cyfluthrin; a mixture of a compound of this invention with esfenvalerate; a mixture of a compound of this invention with methomyl; a mixture of a compound of this invention with imidacloprid; a mixture of a compound of this invention with thiacloprid; a mixture of a compound of this invention with indoxacarb; a mixture of a compound of this invention with abamectin; a mixture of a compound of this invention with endosulfan; a mixture of a compound of this invention with ethiprole; a mixture of a compound of this invention with fipronil; a mixture of a compound of this invention with flufenoxuron; a mixture of a compound of this invention with pyriproxyfen; a mixture of a compound of this invention with pymetrozine; a mixture of a compound of this invention with amitraz; a mixture of a compound of this invention with *Bacillus thuringiensis* and a mixture of a compound of this invention with *Bacillus thuringiensis* delta endotoxin.

In certain instances, combinations with other invertebrate pest control compounds or agents having a similar spectrum of control but a different mode of action will be particularly advantageous for resistance management. Thus, compositions of the present invention can further comprise a biologically effective amount of at least one additional invertebrate pest control compound or agent having a similar spectrum of control but a different mode of action. Contacting a plant genetically modified to express a plant protection compound (e.g., protein) or the locus of the plant with a biologically effective amount of a compound of invention can also provide a broader spectrum of plant protection and be advantageous for resistance management.

Invertebrate pests are controlled in agronomic and nonagronomic applications by applying one or more of the compounds of this invention, in an effective amount, to the environment of the pests including the agronomic and/or nonagronomic locus of infestation, to the area to be protected, or directly on the pests to be controlled. Thus, the present invention further comprises a method for controlling an invertebrate pest, comprising contacting the invertebrate pest or its environment with a biologically effective amount of one or more of the compounds of the invention, or with a composition comprising at least one such compound, or with a composition comprising at least one such compound and an effective amount of at least one additional biologically active compound or agent. Examples of suitable compositions comprising a compound of the invention and an effective amount of at least one additional biologically active compound or agent include granular compositions wherein the additional biologically active compound or agent is present on the same granule as the compound of the invention or on granules separate from those of the compound of this invention.

A preferred method of contact is by spraying. Alternatively, a granular composition comprising a compound of the invention can be applied to the plant foliage or the soil. Compounds of this invention are also effectively delivered through plant uptake by contacting the plant with a composition comprising a compound of this invention applied as a soil drench of a liquid formulation, a granular formulation to the soil, a nursery box treatment or a dip of transplants. Compounds are also effective by topical application of a composition comprising a compound of this invention to the locus of infestation. Other methods of contact include application of a compound or a composition of the invention by direct and residual sprays, aerial sprays, gels, seed coatings, microencapsulations, systemic uptake, baits, eartags, boluses, foggers, fumigants, aerosols, dusts and many others. The compounds of this invention may also be impregnated into materials for fabricating invertebrate control devices (e.g., insect netting).

The compounds of this invention can be incorporated into baits that are consumed by the invertebrates or within devices such as traps and the like. Granules or baits comprising between 0.01-5% active ingredient, 0.05-10% moisture retaining agent(s) and 40-99% vegetable flour are effective in controlling soil insects at very low application rates, particularly at doses of active ingredient that are lethal by ingestion rather than by direct contact.

The compounds of this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrations, spreader stickers, adjuvants, other solvents, and synergists such as piperonyl butoxide often enhance compound efficacy.

The rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control.

The following Tests in the Biological Examples of the Invention demonstrate the control efficacy of compounds of this invention on specific pests. "Control efficacy" represents inhibition of arthropod development (including mortality) that causes significantly reduced feeding. The pest control protection afforded by the compounds is not limited, however, to these species. See Index Table A for compound descriptions. The following abbreviations are used in the Index Table which follows: t is tertiary, n is normal, i is iso, s is secondary, Me is methyl, Et is ethyl, Pr is propyl and Bu is butyl; accordingly i-Pr is isopropyl, s-Bu is secondary butyl, etc. The abbreviation "Ex." stands for "Example" and is followed by a number indicating in which example the compound is prepared.

INDEX TABLE A

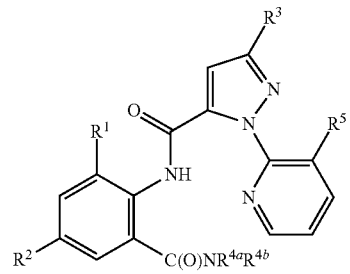

| Compound | $R^1$ | $R^2$ | $R^3$ | $R^{4a}$ | $R^{4b}$ | $R^5$ | m.p. (° C.) |
|---|---|---|---|---|---|---|---|
| 1 | Me | Br | $CF_3$ | i-Pr | H | Cl | 197-198 |
| 2 (Ex. 1) | Me | Cl | $CF_3$ | i-Pr | H | Cl | 195-196 |
| 3 | Me | Cl | $CF_3$ | t-Bu | H | Cl | 223-225 |
| 4 (Ex. 2) | Me | Cl | $CF_3$ | Me | H | Cl | 185-186 |
| 5 | Br | Br | $CF_3$ | i-Pr | H | Cl | 192-193 |
| 6 | Br | Br | $CF_3$ | t-Bu | H | Cl | 246-247 |
| 7 | Br | Br | $CF_3$ | Me | H | Cl | 162-163 |
| 8 | Br | Br | $CF_3$ | Et | H | Cl | 188-189 |
| 9 | Cl | Cl | $CF_3$ | i-Pr | H | Cl | 200-201 |
| 10 | Cl | Cl | $CF_3$ | t-Bu | H | Cl | 170-172 |
| 11 | Cl | Cl | $CF_3$ | Me | H | Cl | 155-157 |
| 12 | Cl | Cl | $CF_3$ | Et | H | Cl | 201-202 |
| 13 | Me | Br | $CF_3$ | t-Bu | H | Cl | 247-248 |
| 14 | Me | Br | $CF_3$ | Et | H | Cl | 192-193 |
| 15 | Me | F | $CF_3$ | i-Pr | H | Cl | 179-180 |
| 16 | Me | Br | Br | i-Pr | H | Cl | 185-187 |
| 17 | Me | $CF_3$ | $CF_3$ | i-Pr | H | Cl | 235-236 |
| 18 | Me | $CF_3$ | $CF_3$ | Et | H | Cl | 216-217 |
| 19 | Me | I | $CF_3$ | i-Pr | H | Cl | 188-189 |
| 20 (Ex. 6) | Me | Cl | Br | Me | H | Cl | 162-164 |
| 21 | Me | Cl | Br | t-Bu | H | Cl | 159-161 |
| 22 | Br | Br | Br | i-Pr | H | Cl | 162-163 |
| 23 | Br | Br | Br | Me | H | Cl | 166-168 |
| 24 | Br | Br | Br | t-Bu | H | Cl | 210-212 |
| 25 | Cl | Cl | Br | i-Pr | H | Cl | 188-190 |
| 26 | Cl | Cl | Br | t-Bu | H | Cl | 179-180 |
| 27 (Ex. 5) | Me | Cl | Br | i-Pr | H | Cl | 159-161 |
| 28 | Cl | Cl | $CF_3$ | i-Pr | H | Cl | 200-202 |
| 29 | Cl | Br | $CF_3$ | t-Bu | H | Cl | 143-145 |
| 30 | Cl | Br | $CF_3$ | Me | H | Cl | 171-173 |
| 31 | Me | Br | Br | Me | H | Cl | 147-149 |
| 32 | Me | Br | $CF_3$ | Me | H | Cl | 222-223 |
| 33 (Ex. 3) | Me | Cl | Cl | i-Pr | H | Cl | 173-175 |
| 34 (Ex. 4) | Me | Cl | Cl | Me | H | Cl | 225-226 |
| 35 | Me | Cl | Cl | t-Bu | H | Cl | 163-165 |
| 36 | Me | Br | Cl | i-Pr | H | Cl | 152-153 |
| 37 | Me | Br | Cl | Me | H | Cl | 140-141 |
| 38 | Me | Br | Br | t-Bu | H | Cl | 215-221 |
| 39 | Me | I | $CF_3$ | Me | H | Cl | 199-200 |
| 40 | Me | $CF_3$ | $CF_3$ | t-Bu | H | Cl | 148-149 |
| 41 | Me | Cl | Cl | Et | H | Cl | 199-200 |
| 42 | Br | Br | Cl | i-Pr | H | Cl | 197-199 |

INDEX TABLE A-continued

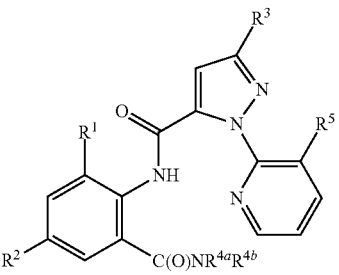

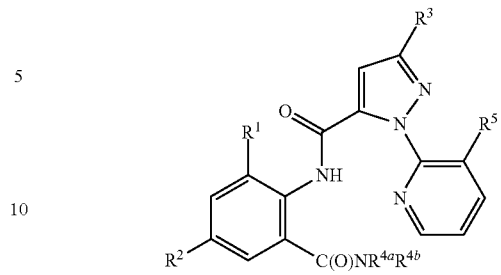

| Compound | R¹ | R² | R³ | R⁴ᵃ | R⁴ᵇ | R⁵ | m.p. (° C.) |
|---|---|---|---|---|---|---|---|
| 43 | Br | Br | Cl | Me | H | Cl | 188-190 |
| 44 | Br | Br | Cl | t-Bu | H | Cl | 194-196 |
| 45 | Br | Br | Cl | Et | H | Cl | 192-194 |
| 46 | Cl | Cl | Cl | i-Pr | H | Cl | 197-199 |
| 47 | Cl | Cl | Cl | Me | H | Cl | 205-206 |
| 48 | Cl | Cl | Cl | t-Bu | H | Cl | 172-173 |
| 49 | Cl | Cl | Cl | Et | H | Cl | 206-208 |
| 50 | Me | F | Br | t-Bu | H | Cl | 124-125 |
| 51 | Br | Br | Br | Et | H | Cl | 196-197 |
| 52 | Cl | Cl | Br | Me | H | Cl | 245-246 |
| 53 | Cl | Cl | Br | Et | H | Cl | 214-215 |
| 54 | Me | Br | Br | Et | H | Cl | 194-196 |
| 55 | Me | I | Br | Me | H | Cl | 229-230 |
| 56 | Me | I | Br | i-Pr | H | Cl | 191-192 |
| 57 | Me | CF₃ | CF₃ | Me | H | Cl | 249-250 |
| 58 | Me | Cl | CF₃ | Et | H | Cl | 163-164 |
| 59 | Me | I | CF₃ | Et | H | Cl | 199-200 |
| 60 | Me | I | CF₃ | t-Bu | H | Cl | 242-243 |
| 61 | Me | Cl | Br | Et | H | Cl | 194-195 |
| 62 | Me | F | CF₃ | Me | H | Cl | 213-214 |
| 63 | Me | F | CF₃ | Et | H | Cl | 212-213 |
| 64 | Me | F | CF₃ | t-Bu | H | Cl | 142-143 |
| 65 | Me | F | Br | Me | H | Cl | 214-215 |
| 66 | Me | F | Br | Et | H | Cl | 205-205 |
| 67 | Me | F | Br | i-Pr | H | Cl | 206-208 |
| 68 | Me | F | Cl | i-Pr | H | Cl | 184-185 |
| 69 | Me | F | Cl | Me | H | Cl | 180-182 |
| 70 | Me | F | Cl | Et | H | Cl | 163-165 |
| 71 | Me | Br | Cl | Et | H | Cl | 192-194 |
| 72 | Me | I | Cl | Me | H | Cl | 233-234 |
| 73 | Me | I | Cl | Et | H | Cl | 196-197 |
| 74 | Me | I | Cl | i-Pr | H | Cl | 189-190 |
| 75 | Me | I | Cl | t-Bu | H | Cl | 228-229 |
| 76 | Me | Br | Cl | t-Bu | H | Cl | 224-225 |
| 77 | Br | Br | Cl | Me | Me | Cl | 153-155 |
| 78 | Me | Br | CF₃ | Me | Me | Cl | 207-208 |
| 79 | Cl | Cl | Cl | Me | Me | Cl | 231-232 |
| 80 | Br | Br | Br | Me | Me | Cl | 189-190 |
| 81 | Cl | Cl | Br | Me | Me | Cl | 216-218 |
| 82 | Cl | Cl | CF₃ | Me | Me | Cl | 225-227 |
| 83 | Me | Br | OCH₂CF₃ | i-Pr | H | Cl | 213-215 |
| 84 | Me | Br | OCH₂CF₃ | Me | H | Cl | 206-208 |
| 85 | Me | Cl | OCH₂CF₃ | i-Pr | H | Cl | 217-218 |
| 86 | Me | Cl | OCH₂CF₃ | Et | H | Cl | 205-207 |
| 87 (Ex. 10) | Me | Cl | OCH₂CF₃ | Me | H | Cl | 207-208 |
| 88 | Me | Br | OCH₂CF₃ | Et | H | Cl | 208-211 |
| 89 | Me | Br | OCH₂CF₃ | t-Bu | H | Cl | 213-216 |
| 90 | Br | Br | CF₃ | Me | Me | Cl | 228-229 |
| 91 | Cl | Br | CF₃ | Me | Me | Cl | 238-239 |
| 92 | Cl | C | OCH₂CF₃ | i-Pr | H | Cl | 232-235 |
| 93 | Cl | Cl | OCH₂CF₃ | Me | H | Cl | 192-195 |
| 94 | Cl | Cl | OCH₂CF₃ | Me | Me | Cl | 132-135 |
| 95 | Br | Br | OCH₂CF₃ | i-Pr | H | Cl | 225-227 |
| 96 | Br | Br | OCH₂CF₃ | Me | H | Cl | 206-208 |
| 97 | Br | Br | OCH₂CF₃ | Me | Me | Cl | 175-177 |
| 98 | Cl | Br | Br | Me | Me | Cl | 237-238 |
| 99 | Cl | Br | Cl | Me | H | Cl | 228-229 |
| 100 | Cl | Br | Cl | Me | Me | Cl | 236-237 |
| 101 | Cl | Br | Br | Me | H | Cl | 226-227 |
| 102 | Cl | F | CF₃ | Me | Me | Cl | 215-216 |
| 103 | Cl | F | CF₃ | Me | H | Cl | 219-220 |
| 104 | Br | F | Br | Me | Me | Cl | 235-236 |
| 105 | Br | F | Br | Me | H | Cl | 238-239 |
| 106 | Br | F | Br | i-Pr | H | Cl | 236-237 |
| 107 | Br | F | Cl | Me | Me | Cl | 246-247 |
| 108 | Br | F | Cl | Me | H | Cl | 233-234 |
| 109 | Br | F | Cl | i-Pr | H | Cl | 153-154 |
| 110 | Me | F | Cl | Me | Me | Cl | 242-243 |
| 111 | Cl | F | Br | Me | Me | Cl | 245-246 |
| 112 | Cl | F | Br | Me | H | Cl | 217-218 |
| 113 | Cl | F | Br | i-Pr | H | Cl | 168-169 |
| 114 | Cl | F | Cl | Me | Me | Cl | 239-240 |
| 115 | Cl | F | Cl | Me | H | Cl | 248-249 |
| 116 | Cl | F | Cl | i-Pr | H | Cl | 169-170 |
| 117 | Br | F | CF₃ | Me | Me | Cl | 191-192 |
| 118 | Br | F | CF₃ | Me | H | Cl | 228-229 |
| 119 | Br | F | CF₃ | i-Pr | H | Cl | 224-226 |
| 120 | Br | Cl | Br | Me | Me | Cl | 188-189 |
| 121 | Br | Cl | Br | Me | H | Cl | 248-249 |
| 122 | Br | Cl | Br | i-Pr | H | Cl | 252-253 |
| 123 | Br | Cl | Cl | Me | Me | Cl | 147-148 |
| 124 | Br | Cl | Cl | Me | H | Cl | 249-250 |
| 125 | Br | Cl | Cl | i-Pr | H | Cl | 239-240 |
| 126 | Br | Cl | CF₃ | Me | Me | Cl | 200-201 |
| 127 | Br | Cl | CF₃ | Me | H | Cl | 158-159 |
| 128 | Br | Cl | CF₃ | i-Pr | H | Cl | 250-250 |
| 129 | Me | Cl | Cl | Me | Me | Cl | 232-233 |
| 130 | Me | Cl | Br | Me | Me | Cl | 210-211 |
| 131 | F | F | Br | Me | H | Cl | 197-198 |
| 132 | F | F | Br | Me | Me | Cl | 218-222 |
| 133 | F | Cl | Br | Me | H | Cl | 203-204 |
| 134 | F | Cl | Br | Me | Me | Cl | 226-227 |
| 135 | F | Cl | Br | i-Pr | H | Cl | 207-208 |
| 136 | F | Cl | Cl | Me | H | Cl | 211-212 |
| 137 | F | Cl | Cl | Me | Me | Cl | 237-238 |
| 138 | F | F | Cl | Me | H | Cl | 159-160 |
| 139 | F | F | Cl | Me | Me | Cl | 225-226 |
| 140 | F | F | Cl | i-Pr | H | Cl | 201-202 |
| 141 | F | Br | Br | Me | H | Cl | 209-210 |
| 142 | F | Br | Br | Me | Me | Cl | 225-226 |
| 143 | F | Br | Br | i-Pr | H | Cl | 208-209 |
| 144 | F | Br | Cl | Me | H | Cl | 209-210 |
| 145 | F | Br | Cl | Me | Me | Cl | 244-245 |
| 146 | F | Br | Cl | i-Pr | H | Cl | 207-208 |
| 147 | F | Br | OCH₂CF₃ | Me | H | Cl | 210-211 |
| 148 | F | Br | OCH₂CF₃ | Me | Me | Cl | 204-206 |

Biological Examples of the Invention

Test A

For evaluating control of diamondback moth (*Plutella xylostella*) the test unit consisted of a small open container with a 12-14-day-old radish plant inside. This was pre-infested with 10-15 neonate larvae on a piece of insect diet by use of a core sampler to remove a plug from a sheet of hardened insect diet having many larvae growing on it and transfer the plug containing larvae and diet to the test unit. The larvae moved onto the test plant as the diet plug dried out.

Test compounds were formulated using a solution containing 10% acetone, 90% water and 300 ppm X-77® Spreader Lo-Foam Formula non-ionic surfactant containing alkylarylpolyoxyethylene, free fatty acids, glycols and isopropanol (Loveland Industries, Inc.), unless otherwise indicated. The formulated compounds were applied in 1 mL of liquid through a SUJ2 atomizer nozzle with ⅛ JJ custom body (Spraying Systems Co.) positioned 1.27 cm (0.5 inches) above the top of each test unit. All experimental compounds in this screen were sprayed at 50 ppm and replicated three times. After spraying of the formulated test compound, each test unit was allowed to dry for 1 hour and then a black, screened cap was placed on top. The test units were held for 6 days in a growth chamber at 25° C. and 70% relative humidity. Plant feeding damage was then visually assessed.

Of the compounds tested, the following provided excellent levels of plant protection (10% or less feeding damage): 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 119, 120, 121, 122, 123, 124, 125, 126, 127, 128, 129, 130, 131, 132, 133, 134, 135, 136, 137.

Test B

For evaluating control of fall armyworm (*Spodoptera frugiperda*) the test unit consisted of a small open container with a 4-5-day-old corn (maize) plant inside. This was pre-infested with 10-15 1-day-old larvae on a piece of insect diet by use of a core sampler as described for Test A.

Test compounds were formulated and sprayed at 50 ppm as described for Test A. The applications were replicated three times. After spraying, the test units were maintained in a growth chamber and then visually rated as described for Test A.

Of the compounds tested, the following provided excellent levels of plant protection (10% or less feeding damage): 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 92, 93, 94, 95, 96, 97, 98, 99, 100, 101, 102, 103, 104, 105, 106, 107, 108, 109, 110, 111, 112, 113, 114, 115, 116, 117, 119, 120, 121, 122, 123, 124, 125, 126, 127, 128, 129, 130, 131, 132, 133, 134, 135, 136, 137.

Test C

For evaluating control of tobacco budworm (*Heliothis virescens*) the test unit consisted of a small open container with a 6-7 day old cotton plant inside. This was pre-infested with 8 2-day-old larvae on a piece of insect diet by use of a core sampler as described for Test A.

Test compounds were formulated and sprayed at 50 ppm as described for Test A. The applications were replicated three times. After spraying, the test units were maintained in a growth chamber and then visually rated as described for Test A.

Of the compounds tested, the following provided excellent levels of plant protection (10% or less feeding damage): 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 92, 93, 94, 95, 96, 97, 98, 99, 100, 101, 102, 103, 104, 105, 106, 107, 108, 109, 110, 111, 112, 113, 114, 115, 116, 117, 119, 120, 121, 122, 123, 124, 125, 126, 127, 128, 129.

Test D

For evaluating control of beet armyworm (*Spodoptera exigua*) the test unit consisted of a small open container with a 4-5-day-old corn plant inside. This was pre-infested with 10-15 1-day-old larvae on a piece of insect diet by use of a core sampler as described for Test A.

Test compounds were formulated and sprayed at 50 ppm as described for Test A. The applications were replicated three times. After spraying, the test units were maintained in a growth chamber and then visually rated as described for Test A.

Of the compounds tested, the following provided excellent levels of plant protection (10% or less feeding damage): 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 100 101, 102, 103, 104, 105, 106, 107, 108, 109, 110, 111, 112, 113, 114, 115, 116, 117, 119, 120, 121, 122, 123, 124, 125, 126, 127, 128, 129.

Test E

For evaluating control of green peach aphid (*Myzus persicae*) through contact and/or systemic means, the test unit consisted of a small open container with a 12-15-day-old radish plant inside. This was pre-infested by placing on a leaf of the test plant 30-40 insects on a piece of leaf excised from a culture plant (cut-leaf method). The larvae moved onto the test plant as the leaf piece desiccated. After pre-infestation, the soil of the test unit was covered with a layer of sand.

Test compounds were formulated using a solution containing 10% acetone, 90% water and 300 ppm X-77® Spreader Lo-Foam Formula non-ionic surfactant containing alkylarylpolyoxyethylene, free fatty acids, glycols and isopropanol (Loveland Industries, Inc.), unless otherwise indicated. The formulated compounds were applied in 1 mL of liquid through a SUJ2 atomizer nozzle with ⅛ JJ custom body (Spraying Systems Co.) positioned 1.27 cm (0.5 inches) above the top of each test unit. All experimental compounds in this screen were sprayed at 250 ppm and replicated three times. After spraying of the formulated test compound, each test unit was allowed to dry for 1 hour and then a black, screened cap was placed on top. The test units were held for 6 days in a growth chamber at 19-21° C. and 50-70% relative humidity. Each test unit was then visually assessed for insect mortality.

Of the compounds tested, the following resulted in at least 80% mortality: 1, 2, 3, 4, 5, 6, 7, 8, 10, 11, 12, 13, 14, 16, 20, 21, 22, 23, 25, 26, 27, 28, 29, 31, 32, 33, 36, 38, 39, 41, 42, 43, 45, 46, 47, 49, 51, 52, 54, 55, 56, 58, 59, 60, 61, 62, 63, 64, 65, 66, 67, 69, 72, 74, 77, 78, 79, 80, 81, 82, 83, 84, 85, 86, 87, 88, 90, 91, 93, 98, 99, 100, 101, 102, 103, 104, 105, 106, 108, 109, 111, 112, 113, 114, 115, 116, 126, 127, 128, 131, 135.

Test F

For evaluating control of cotton melon aphid (*Aphis gossypii*) through contact and/or systemic means, the test unit consisted of a small open container with a 6-7-day-old cotton plant inside. This was pre-infested with 30-40 insects on a piece of leaf according to the cut-leaf method described for Test E, and the soil of the test unit was covered with a layer of sand.

Test compounds were formulated and sprayed at 250 ppm as described for Test E. The applications were replicated three times. After spraying, the test units were maintained in a growth chamber and then visually rated as described for Test E.

Of the compounds tested, the following resulted in at least 80% mortality: 1, 2, 4, 5, 7, 8, 10, 11, 12, 13, 14, 16, 20, 21, 22, 23, 25, 26, 27, 28, 29, 31, 32, 33, 34, 36, 38, 39, 42, 43, 45, 46, 47, 49, 51, 52, 53, 54, 55, 56, 58, 59, 62, 63, 65, 66, 67, 77, 78, 79, 80, 81, 82, 87, 88, 90, 91, 93, 94, 96, 98, 99, 100, 101, 102, 103, 104, 105, 106, 107, 108, 109, 111, 112, 113, 114, 115, 116, 117, 119, 120, 121, 122, 123, 124, 125, 126, 127, 128, 131, 133, 135, 136.

Test G

For evaluating control of silverleaf whitefly (*Bemisia tabaci*), the test unit consisted of a 14-21-day-old cotton plant grown in Redi-Earth® media (Scotts Co.) with at least two true leaves infested with 2nd and 3rd instar nymphs on the underside of the leaves.

Test compounds were formulated in no more than 2 mL of acetone and then diluted with water to 25-30 mL. The formulated compounds were applied using a flat fan air-assisted nozzle (Spraying Systems 122440) at 10 psi (69 kPa). Plants were sprayed to run-off on a turntable sprayer (patent application EP-1110617-A1). All experimental compounds in this screen were sprayed at 250 ppm and replicated three times. After spraying of the test compound, the test units were held for 6 days in a growth chamber at 50-60% relative humidity and 28° C. daytime and 24° C. nighttime temperature. Then the leaves were removed and then dead and live nymphs were counted to calculate percent mortality.

Of the compounds tested, the following resulted in at least 80% mortality: 1, 2, 3, 4, 5, 6, 7, 8, 9, 10, 11, 12, 13, 14, 16, 19, 20, 21, 22, 23, 24, 25, 26, 27, 29, 31, 32, 33, 34, 39, 42, 43, 45, 46, 47, 49, 51, 52, 53, 54, 55, 56, 59, 77, 78, 79, 80, 81, 82, 87, 90, 93.

Test H

For evaluating soil systemic control of tobacco budworm (*Heliothis virescens*), cotton plants were grown in sassafras soil in 15-cm pots in aluminum trays. When the plants reached square stage (bud formation on the plant) the plants were treated with the test compounds.

Test compounds were formulated in 0.25 mL of acetone and then diluted with water to provide solutions of 1, 5, 10 and 50 ppm. 10 mL of the treatment solutions were added to the pots weekly for four weeks, with four replicates of each treatment rate. One day after the second, third and fourth treatments, 35-50 first instar *Heliothis virescens* larvae were brushed on each plant with paintbrushes and placed on the terminal area, squares, and bolls. Five days after the last infestation with larvae the plants were rated for damage. Of the compounds tested, the following provided excellent levels of plant protection at 10 ppm (10% or less feeding damage): 16.

Of the compounds tested, the following also provided excellent protection of squares and bolls at 10 ppm, with no feeding or minimal sepal damage: 16.

Test I

Test I followed an alternative protocol for evaluating soil systemic control of tobacco budworm (*Heliothis virescens*). Cotton plants were grown in sassafras soil in 15-cm pots under greenhouse conditions. When the plants reached square stage (bud formation on the plant) the soil surface was treated with the test compounds.

Test compounds were formulated in 0.25 mL of acetone and then diluted with water. Ten mL of treatment solution containing 3 mg of compound was added to the soil surface of each pot. The plants were watered the next day and each day following as needed. At 1, 2 and 4 days after treatment, leaves were excised for evaluation. Two sets of leaves were selected from each plant: upper leaves at approximately second node from terminal and with area greater than 25 $cm^2$ and lower leaves at approximately third node from bottom and with area greater than 25 $cm^2$. The excised leaves were cut into 3 cm×2 cm sections and placed into test trays made of high-impact styrene consisting of sixteen contiguous wells, each 6 cm wide, 4 cm long and 3 cm deep, with a clear plastic lid molded so that it locked into each well by friction. Solidified agar was placed into the bottom of each well to maintain moisture for plant material. One second instar tobacco budworm was placed into each well with plant material; cells were sealed and held at 25° C. and provided with 16 hours of light per day. For leaves excised at 1, 2, and 4 days mortality was observed 4 days after treatment with one second instar todacco budworm.

Of the compounds tested, the following compounds provided excellent levels of mortality (greater than 70% mortality) on upper leaves excised at 4 days after treatment at the test rate: 2, 27, 33.

Test J

For evaluating soil systemic control of fall armyworm (*Spodoptera frugiperda*), corn (maize) plants (Pioneer #3394) were grown in small pots for 5 days until they were at least 4 cm tall and the first leaf was unfurling.

Test compounds were dissolved in 0.25 mL of acetone and diluted with water to provide solutions of 1, 10, 50 and 200 ppm. 1 mL of the test solution was applied by pipette to the surface of the soil in each pot, with eight plants for each compound/rate. The pots were covered and held at 25° C. with 16 hours of light per day. The plants were watered the next day and each day following as needed. After 6 days, the plant matter above the first leaf was excised and cut into 3-cm lengths. Each test unit was a high-impact styrene tray (Supplier: Clearpack Company, 11610 Copenhagen Court, Franklin Park, Ill. 60131) consisting of sixteen contiguous wells each 6 cm wide, 4 cm long and 3 cm deep, with a clear plastic lid molded so that it locked into each well by friction. Solidified agar (2 to 4 mL) was placed onto the bottom of each well to maintain moisture in the wells during the test. Each 3-cm length of corn plant matter was placed into a tray such that the plant matter was contained within two wells. One second-instar fall armyworm (Spodoptera frugiperda) larva was placed in each well, the tray was covered and then the test units were held at 25° C. with 16 hours of light per day. Mortality was observed after four days.

$LC_{90}$ concentrations (test compound concentrations giving 90% kill of the larvae) were calculated based on probit analysis (log linear regression) using a general linearized model (GLIM) of the SAS statistical computer analysis product of SAS Institute (Cary, N.C., U.S.A.). Of the compounds tested, the following provided excellent levels of mortality, with $LC_{90}$ values of 10 ppm or less: 1, 2, 4, 9, 11, 12, 14, 16, 20, 22, 24, 31, 32, 33, 34.

Test K

For evaluating control of Colorado potato beetle (*Leptinotarsa decemlineate*), 5 mg samples of the test compounds were dissolved in 1 mL of acetone. This solution was then diluted to 100 mL total volume using an aqueous 500 ppm solution of Ortho X77™ surfactant. Serial dilutions were made to obtain 50 mL of 10 ppm concentration.

The diluted solutions of the test compounds were sprayed to run-off on three-week-old potato or tomato plants. The plants were placed on a rotating turntable sprayer (10 rpm). Test solutions were applied using a flat fan air-assisted nozzle (Spraying Systems 122440) at 10 psi (69 kPa). After each treated plant had dried, leaves were excised from the treated plant. The leaves were cut into pieces, which were placed singly into 5.5 cm-by-3.5 cm cells of a sixteen-cell plastic tray. Each cell contained a 2.5-cm square of moistened chromatography paper to prevent desiccation. One second instar larvae was placed in each cell. At three days after infestation the total number of dead Colorado potato beetles was recorded.

Of the compounds tested, the following resulted in at least 90% mortality at 10 ppm: 2, 4, 27, 33, 34, 41, 61, 85.

Test L

For evaluating control of boll weevil (*Anthonomus g. grandis*), samples of the test compounds were dissolved in 1 mL of acetone. This solution was then diluted to 100 mL total volume using an aqueous 500 ppm solution of Ortho X77™ surfactant. Serial dilutions were made to obtain 50 mL of 50 ppm concentration.

The diluted solutions of the test compounds were sprayed to run-off on three-week-old cotton plants. The plants were placed on a rotating turntable sprayer (10 rpm). Test solutions were applied using a flat fan air-assisted nozzle (Spraying Systems 122440) at 10 psi (69 kPa). Sprayed and dried plants were incased in a plastic cylinder. Twenty weevils were placed in each cylinder containing a whole cotton plant. At three days after infestation a feeding damage rating was taken.

Of the compounds tested, the following provided excellent levels of plant protection at 50 ppm (10% or less feeding damage): 20, 27.

Test M

For evaluating control of thrips (*Frankliniella* sp.), samples of the test compounds were dissolved in 1 mL of acetone. This solution was then diluted to 100 mL total volume using an aqueous 500 ppm solution of Ortho X77™ surfactant. Serial dilutions were made to obtain 50 mL of 10 ppm concentration.

The diluted solutions of the test compounds were sprayed to run-off on three-week-old cotton or soybean plants infested with thrips. The plants were placed on a rotating turntable sprayer (10 rpm). Test solutions were applied using a flat fan air-assisted nozzle (Spraying Systems 122440) at 10 psi (69 kPa). Sprayed and dried plants were incased in a plastic cylinder. At four days after application the total number of dead thrips was recorded.

Of the compounds tested, the following resulted in at least 90% mortality at 10 ppm: 32.

What is claimed is:

1. A composition, comprising: a compound selected from Formula 1, an N-oxide thereof, and an agriculturally suitable salt thereof; and pymetrozine,
   wherein Formula 1 is

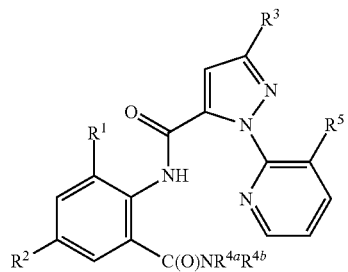

$R^1$ is $CH_3$, F, Cl or Br;
$R^2$ is F, Cl, Br, I or $CF_3$;
$R^3$ is $CF_3$, Cl, Br or $OCH_2CF_3$;
$R^{4a}$ is $C_1$-$C_4$ alkyl;
$R^{4b}$ is H or $CH_3$; and
$R^5$ is Cl or Br.

2. The composition of claim 1 further comprising at least one of a surfactant, a solid diluent or a liquid diluent.

3. The composition of claim 1 wherein the first compound is

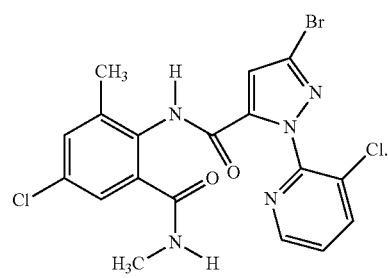

4. A method for controlling an invertebrate pest, comprising: contacting the invertebrate pest or its environment with the composition of claim 1 or claim 3.

5. The method of claim 4 wherein the application rate for the compound of Formula 1 in an agronomic ecosystem ranges from about 0.0001 to 8 kg/ha and in a nonagronomic application ranges from about 0.1 to 150 mg/square meter.

6. The method of claim 5 wherein the application rate for the compound of Formula 1 in an agronomic ecosystem ranges from about 0.01 to 2 kg/ha.

7. The method of claim 5 wherein the application rate for the compound of Formula 1 in a nonagronomic application ranges from about 1.0 to 50 mg/square meter.

8. A process for preparing pesticides, comprising: mixing a compound of Formula 1, an N-oxide thereof, or an agriculturally suitable salt thereof, as set forth in claim 1, and pymetrozine with diluents, surfactants, or combinations thereof.

* * * * *